US007070976B2

(12) United States Patent
Wood et al.

(10) Patent No.: US 7,070,976 B2
(45) Date of Patent: Jul. 4, 2006

(54) MATRIX METALLOPROTEINASE POLYPEPTIDE

(75) Inventors: Timothy Wood, Nacka (SE); Jonas Ekblom, Uppsala (SE); Erik Holmgren, Lidingo (SE); Mats Kihlén, Uppsala (SE)

(73) Assignee: Pfizer Inc., New York, NY (US)

( * ) Notice: Subject to any disclaimer, the term of this patent is extended or adjusted under 35 U.S.C. 154(b) by 209 days.

(21) Appl. No.: 10/791,980

(22) Filed: Mar. 3, 2004

(65) Prior Publication Data

US 2004/0146499 A1    Jul. 29, 2004

Related U.S. Application Data

(62) Division of application No. 09/862,631, filed on May 22, 2001, now Pat. No. 6,734,005.

(60) Provisional application No. 60/206,119, filed on May 22, 2000.

(51) Int. Cl.
    *C12N 9/64*    (2006.01)
(52) U.S. Cl. .......................... 435/226; 424/656; 514/2
(58) Field of Classification Search .................... None
    See application file for complete search history.

(56) References Cited

U.S. PATENT DOCUMENTS

| 4,399,216 | A |   | 8/1983  | Axel et al. ............... 435/6 |
| 4,683,195 | A |   | 7/1987  | Mullis et al. ............ 435/6 |
| 4,683,202 | A |   | 7/1987  | Mullis ................... 435/91 |
| 4,879,236 | A |   | 11/1989 | Smith et al. ........... 435/235 |
| 5,202,231 | A |   | 4/1993  | Drmanac et al. ......... 435/6 |
| 5,521,065 | A |   | 5/1996  | Whiteley et al. ........ 435/6 |
| 5,585,277 | A |   | 12/1996 | Bowie et al. .......... 436/518 |
| 5,837,832 | A |   | 11/1998 | Chee et al. ........... 536/22.1 |
| 6,399,371 | B1| * | 6/2002  | Falduto et al. |

FOREIGN PATENT DOCUMENTS

| EP | 0 367 566      | 5/1990  |
| WO | 91/09955       | 7/1991  |
| WO | 91/18982       | 12/1991 |
| WO | 92/20808       | 11/1992 |
| WO | 93/11236       | 6/1993  |
| WO | 94/12650       | 6/1994  |
| WO | 95/20652       | 8/1995  |
| WO | 96/22976       | 8/1996  |
| WO | 97/09433       | 3/1997  |
| WO | 98/37177       | 8/1998  |
| WO | WO 00/18900    | 6/2000  |
| WO | WO 01/16335 A2 | 3/2001  |

OTHER PUBLICATIONS

Lohi et al., Epilysin, a novel human matrix metalloproteinase (MMP-28) expressed in testis and keratinocytes and in response to injury. J Biol Chem. 2001 Mar. 30;276(13): 10134-44.*
UniProt Database Accession No. MM28_Human Oct. 10, 2003 from Lohi et al., Epilysin, a novel human matrix metalloproteinase (MMP-28) expressed in testis and keratinocytes . . . J Biol Chem. Mar. 30, 2001;276(13): 10134-44. Alignment with SEQ ID NO.: 6.*
McDonagh et al., Production of caseinophosphopeptides (CPPs) from sodium caseinate using a range of commercial protease preparations. International Dairy Journal (1988), 8(1), 39-45.*
Ausubel, 1988 Current Protocols in Molecular Biology Chapters 1, 9, 13, and 16 and Appendix 5. John Wiley & Sons, Inc. New York, NY.*
Birren et al, 1998 Homo sapiens chromosome 17, clone hRPC. 161_P_9. EMBL Acc# AC006237 alignment with SEQ ID No.: 3.*
Akane et al., "Direct Dideoxy Sequencing of Genomic DNA by Ligation-Mediated PCR", *Biotechniques*, 1994, vol. 16, pp. 238-241.
Altschul et al., "Basic Local Alignment Search Tool," *J. Mol. Biol.*, 1990, 215, 403-410.
American Veterinary Medical Association, *Report of the American Veterinary Medical Assoc.*, Panel on Euthanasia, *Journal of American Veterinary Medical Assoc.*, 1993, 202, 229-249.
Anderson, "Human Gene Therapy", *Nature*, 1998, Suppl. To vol. 392, No. 3379, pp. 25-30.
Anderson, W. F., "Human gene therapy," *Science*, 1992, 256, 808-813.
Aujame et al., "High Affinity Human Antibodies by Phage Display", *Human Antibodies*, 1997, vol. 8, No. 4, pp. 155-168.
Ausubel, et al. (Eds.), "Chapter 6, Screening of recombinant DNA libraries," *Current Protocols in Molecular Biology*, 1994, John Wiley & Sons, 6.0.1.-6.4.10.
Baindur et al., "Selective fluorescent ligands for pharmacological receptors," *Drug Dev. Res.*, 1994, 33, 373-398.
Baker et al., "Induction of Acetylcholine Receptor Clustering by Native Polystyrene Beads. Implication of an Endogenous Muscle-derived Signalling System", *J. Cell Sci.*, 1992, vol. 102, pp. 543-555.
Benoist et al., "*In vivo* sequence requirements of the SV40 early promoter region," *Nature*, 1981, 290, 304-310.

(Continued)

*Primary Examiner*—Sheridan Lee Swope
(74) *Attorney, Agent, or Firm*—Steve Zelson; Victor Donahue

(57) ABSTRACT

The present invention provides genes encoding novel matrix metalloproteinases termed MMP; constructs and recombinant host cells incorporating the genes; the MMP polypeptides encoded by the genes; antibodies to the MMP polypeptides; and methods of making and using all of the foregoing.

2 Claims, No Drawings

OTHER PUBLICATIONS

Bertilsson, G. et al., "Identification of a human nuclear receptor defines a new signaling pathway for CYP3A induction", *Proc. Natl. Acad. Sci. USA*, 1998, 95, 12208-12213.

Bosseé, R., et al., "Development of nonseparation binding and functional assays for G protein-coupled receptors for high throughput screening: Pharmacological characterization of the immobilized CCR5 receptor on FlashPlate®," *J. Biomolecular Screening*, 1998, 3(4), 285-292.

Bruggemann, M., et al., "Production of human antibody repertoires in transgenic mice," *Curr. Opin. Biotechnol.*, 1997, 8, 455-458.

Bruggemann, M., et al., "Strategies for expressing human antibody repertoires in transgenic mice," *Immunol. Today*, 1996, 17(8), 391-397.

Can, D.E., et al., "Harnessing the Biosynthetic Code: Combinations, Permutations, and Mutations," *Science*, Oct. 1998, 282, 63-68.

Capecchi, M. R., "Altering the genome by homologous recombination," *Science*, 1989, 244, 1288-1292.

Cheng, L. et al., "Adenovirus-mediated gene transfer of the human tissue inhibitor of metalloproteinase-2 blocks vascular smooth muscle cell invasiveness in vitro and modulates neointimal development in vivo", *Circulation*, 1998, 98, 2195-2201.

Choo, Y., et al., "Promoter-specific activation of gene expression directed by bacteriophage-selected zinc fingers," *J. Mol. Biol.*, 1997, 273, 525-532.

Cosman, D., et al., "High Level Stable Expression of Human Interleukin-2 receptors in Mouse Cells Generates only Low Affinity Interleukin-2 Binding Sites," *Mol. Immunol.*, 1986, 23(9), 935-941.

Cosman, D., et al., "Cloning, sequence and expression of human interleukin-2 receptor," *Nature*, 1984, 312, 768-771

Dayoff, in *Atlas of Protein Sequence and Structure*, 1972, National Biochemical Research Foundation, Washington, D.C., 5, 124.

Deckert, T. et al., "Implications for micro-and macrovascular disease", *Diabetes Care*, 1992, 15(9), 1181-1191.

Douglas, A. M., et al., "Direct sequencing of double-stranded PCR products incorporating a chemiluminescent detection procedure," *Biotechniques*, 1993, 14, 824-828.

Drmanac, R., et al., "DNA Sequence Determination by Hybridization A Strategy for Efficient Large-Scale Sequencing," *Science*, Jun. 1993, 260, 1649-1652.

Drmanac, S., et al., "Accurate sequencing by hybridization for DNA diagnostics and individual genomics," *Nature Biotechnology*, 1998, 16, 54-58.

Ebihara, I., et al., "Increased plasma metalloproteinase-9 concentrations precede development of microalbuminuria in non-insulin-dependent diabetes mellitus", *Am. J. Kidney Dis.*, 1998, 32(4), 544-550.

Falk, E. et al., "Coronary plaque disruption", *Circulation*, 1995, 92, 657-671.

Fields, S., et al., "A novel genetic system to detect protein-protein interactions," *Nature*, 1989, 340, 245-246.

Fields, S., et al., "The two-hybrid system: an assay for protein-protein interactions," *Trends in Genetics*, 1994, 10, 286-292.

Fischer, S. G., et al., "DNA fragments differing by single base-pair substitutions are separated in denaturing gradient gels: Correspondence with melting theory," *Proc. Natl. Acad. Sci. USA*, 1983, 80, 1579-1583.

Foote, J., et al., Antibody framework residues affecting the conformation of the hypervariable loops, *J. Mol. Biol.*, 1992, 224, 487-499.

Forough, R. et al., "Overexpression of tissue inhibitor of matrix metalloproteinase-1 inhibits vascular smooth muscle cell functions in vitro and in vivo", *Cir. Res.*, 1996, 79(4), 812-820.

Frank, K. et al., "Diabetic eye disease: A primary care perspective", *South. Med. J.*, 1996, 89(5), 463-470.

Friedmann, T., "Progress toward human gene therapy," *Science*, 1989, 244, 1275-1281.

Fuster, V. et al., "Acute coronary syndromes; biology", *Lancet*, 1999, 353(suppl. II), 5-9.

Gerhardt, C. C., et al., "Functional characteristics of heterologously expressed 5-HT receptors," *Eur. J. Pharmacology*, 1997, 334, 1-23.

Gomez, D. et al., "Tissue inhibitors of metalloproteinases: structure, regulation and biological functions", *Eur. J. Cell. Biol.*, 1997, 74, 111-122.

Greisman, H. A., et al., "A general strategy for selecting high-affinity zinc finger proteins for diverse DNA target sites," *Science*, 1997, 275, 657-661.

Harendza, S. et al., "In vitro characterization of the mesangial phenotype in a proliferative glomerulonephritis of the rat", *Nephrol. Dial. Transplant*, 1997, 12, 2537-2541.

Henikoff, S., et al., "Amino acid substitution matrices from protein blocks," *Proc. Natl. Acad. Sci. USA*, 1992, 89, 10915-10919.

Hill, D. C., "Trends in development of high-throughput screening technologies for rapid discovery of novel drugs," *Cur. Opinion Drug Disc. Dev.*, 1998, I(I), 92-97.

Hoogenboom H. R., "Designing and optimizing library selection strategies for generating high-affinity antibodies," *TIBTECH*, 1997, 15, 62-70.

Jampol, L. et al., "Peripheral proliferative Retinopathies", *Surv. Ophthalmol.*, 1980, 25(I), 1-14.

Jayawickreme, C. K., et al., Gene expression system in the development of high-throughput screens, *Current Opinion in Biotechnology*, 1997, 8, 629-634.

Jones, P. T., et al., "Replacing the compementarity-determining regions in a human antibody with those from a mouse," *Nature*, 1986, 321, 522-525.

Karlin, S., et al., "Applications and statistics for multiple high-scoring segments in molecular sequences," *Proc. Natl. Acad. Sci. USA*, 1993, 90, 5873-5787.

Kettleborough, C. A., et al., "Humanization of a mouse monoclonal antibody by CDR-grafting: the importance of framework residues on loop conformation," *Protein Engin.*, 1991, 4(7), 773-783.

Kieleczawa, J., et al., "DNA sequencing by primer walking with strings of contiguous hexamers," *Science*, 1992, 258, 1787-1791.

Kim, J., et al., "Design of TATA box-binding protein/zinc finger fusions for targeted regulation of gene expression," *Proc. Natl. Acad. Sci. USA*, 1997, 94, 3616-3620.

Kosano, H. et al., "ProMMP-9 (92 kDa gelatinase) in vitreous fluid of patients with proliferative diabetic retinopathy", *Life Sciences*, 1999, 64(25), 2307-2315.

Lehninger, "Chapter 4, The amino acid building blocks of proteins," *Biochemistry*, $2^2$Ed., 1975, Worth Publishers, Inc., New York, New York, 71-77.

Lin, A. H., et al., "The oxazolidinone eperezolid binds to the 50S ribosomal subunit and competes with binding of chloramphenicol and lincomycin," *Antimicrobial Agents and Chemotherapy*, 1997, 41(10), 2127-2131.

Lindstedt, L. et al., "Matrix metalloproteinases-3, -7 and -12, but not -9, reduce high intensity lipoprotein-induced cholesterol efflux from human macrophage foam cells by truncation of the carboxyl terminus of apolipoprotein A-I", *J. Biol. Chem.*, 1999, 274(32), 22627-22634.

Liu, Q., et al., "Design of polydactyl zinc-finger proteins for unique addressing within complex genomes," *Proc. Natl. Acad. Sci. USA*, 1997, 94, 5525-5530.

Luckow, V. A., et al., "High Level Expression of Nonfused Foreign Genes with Autographa californica Nuclear Polyhedrosis Virus Expression Vectors," *Virology*, 1989, 170, 31-39.

Luckow, V. A., et al., "Trends in the development of baculovirus expression vectors," *Bio/Technology*, 1988, 6, 47-55.

Makishima, M. et al., "Identification of a nuclear receptor for bile acids", *Science*, 1999, 284, 1362-1365.

Maxam, A. M., et al., "Sequencing end-labeled DNA with bse-secific chemical cleavages", *Meth. Enzymol.*, 1977, vol. 65, 499-560.

McColl, D. J., et al., "Structure-based design of an RNA-binding zinc finger", *Proc. Natl. Acad. Sci. (USA )*, 1997, vol. 96, 9521-9526.

Miller, A. D., "Human gene therapy comes of age", *Nature*, 1992, vol. 357, pp. 455-460.

Mirzabekov, A. D., "DNA sequencing by hybridization—A megasequencing method and a diagnostic tool?", *TIBTECH*, 1994, vol. 12, 27-32.

Morrison, et al., "Genetically engineered antibody molecules," Dixon, F.J., et al. (Eds.), *Adv. Immunol.*, 1989, 44, 65-92.

Myers, R. M., et al., "Detection of single base substitutions by ribonuclease cleavage at mismatches in RNA: DNA duplexes", *Science*, 1985, vol. 230, 1242-1246.

Myers, P., "Will combinatorial chemistry deliver real medicines," *Curr. Opin. Biotechnology*, 1997, 8, 701-707.

Nagase, H. et al., "Matrix metalloproteinases", *J. Biol. Chem.*, 1999, 274(31), 21491-21494.

Nakayama, G. R., "Microplate assays for high-throughput screening," *Cur. Opinion Drug Disc. Dev.*, 1998, I, 85-91.

Newby, A.C. et al., "Extracellular matrix degrading metalloproteinases in the pathogenesis of arteriosclerosis", *Basic Res. Cardiol.*, 1994, 89(suppl. 1), 59-70.

Okayama, H., et al., "A cDNA cloning vector that permits expression of cDNA inserts in mammalian cells," *Mol. Cell. Biol.*, 1983, 3(2), 280-289.

Orita, M., et al., "Detection of polymorphisms of human DNA by gel electrophoresis as single-strand conformation polymorphisms," *Proc. Natl. Acad. Sci. USA*, 1989, 86, 2766-2770.

Padlan, E. A., "A possible procedure for reducing the immunogenicity of antibody variable domains while preserving their ligand-binding properties," *Molecular Immunol.*, 1991, 28(4/5), 489-498.

Parks, D. et al., "Bile acids: Natural ligands for an orphan nuclear receptor", *Science*, 1999, 284, 1365-1368.

Pastinen, T., et al., "Minisequencing: A specific tool for DNA analysis and diagnostics on oligonucleotide arrays," *Genome Res.*, 1997, 7, 606-614.

Pausch, M. H., "G-protein-coupled receptors in saccharomyces cerevisiae: high-throughput screening assays for drug discovery," *Trends in Biotechnology*, 1997, 15, 487-494.

Pease, A. C., et al., "Light-generated oligonucleotide arrays for rapid DNA sequence analysis," *Proc. Natl. Acad. Sci. USA*, 1994, 91, 5022-5026.

Philips, S. D., et al., "Quino[1,2-c]quinazolines. I. Synthesis of quino[1,2-c]quinazolinium derivatives and the related indazolo[2,3-a]quinoline derivatives as analogs of the antitumor benzol[c]phenanthridine alkaloids," *J. Heterocyclic Chem.*, 1980, 17(19), 1489-1596.

Pillemer, G., et al., "Insulin dependence of murine lymphoid T-cell leukemia," *Int. J. Cancer*, 1992, 50, 80-85.

Pindon, A., et al., "Thrombin-induced reversal if astricyte stellation is mediated by activation of protein kinase C β-1," *Eur. J. Biochem.*, 1998, 255, 766-774.

Posner, I., et al., "Kinetics of inhibition by tyrphostins of the tyrosine kinase activity of the epidermal growth factor receptor and analysis," *Molecular Pharmacology*, 1993, 45, 673-683.

Pulver, A. E., et al., "The Johns Hopkins University Collaborative Schizophrenia Study: An Epidemiologic-Genetic Approach to Test the Heterogeneity Hypothesis and Identify Schizophrenia Susceptibility Gene," *Cold Spring Harbor Symposia on Quantitative Biology*, ©1996, 61, 797-814.

Qu et al., "A Role for melanin-concentrating hormone in the central regulation of feeding behaviour", *Nature*, 1996, 380, 243-247.

Rader, C., et al., "Phage display of combinationial antibody libraries," *Curr. Opin. Biotechnol.*, 1997, 8, 503-508.

Ramsay, G., "DNA chips: state-of-the-art," *Nature Biotechnology*, 1999, 16, 40-48.

Reece, P. A., et al., "Pharmacokinetics of trimetrexate administered by five-day continuous infusion to patients with advanced cancer," *Cancer Research*, 1987, 47(11), 2996-2999.

Reinsheid, R. K., et al., "Orphanin FQ: A neuropeptide that activates an opioidlike G protein-coupled receptor," *Science*, 1995, 270, 792-794.

Rendu, F., et al., "Inhibition of platelet activation by tyrosine kinase inhibitors," *Biol. Pharmacology*, 1992, 44(5), 881-888.

Riechmann, L., et al., "Reshaping human antibodies for therapy," *Nature*, 1988, 332, 323-327.

Riesner, D., et al., "Temperature-gradient gel electrophoresis of nucleic acids: Analysis of conformational transitions, sequence variations, and protein-nucleic acid interactions," *Electrophoresis*, 1989, 10, 377-389.

Roberts, E., et al., "Potassium permanganate and tetraethylammonium chloride are a safe and effective substitute for osmium tetroxide in solid-phase fluorescent chemical cleavage of mismatch," *Nucl. Acids Res.*, 1997, 25(16), 3377-3378.

Rogers, M. V., "Light on high-throughput screening: fluorescence-based assay technologies," *Drug Discovery Today*, 1997, 2(4), 156-160.

Rossi, M. et al., "Melanin-Concentrating Hormone Acutely Stimulates Feeding, But Chronic Administration Has No Effect on Body Weight", *Edocrinology*, 1997, 138 (I), 351-355.

Rowley, G., et al., "Ultrarapid mutation detection by multiplex solid-phase chemical cleavage," *Genomics*, 1995, 30, 574-582.

Saito, Y., et al., "Molecular characterization of the melanin-concentrating-hormone receptor," *Nature*, 1999, 400, 265-269.

Sakurai, T., et al., "Orexins and orexin receptors: A family of hypothalamic neuropeptides and G protein-coupled receptors that regulate feeding behavior," *Cell*, 1998, 92, 573-585.

Sanger, F., et al., "DNA sequencing with chain-terminating inhibitors," *Proc. Natl. Acad. Sci. USA*, 1977, 74(12), 5463-5467.

Sauro, M. D., et al., "Tyrphostin attenuates platelet-derived growth factor-induced contraction in aortic smooth muscle through inhibition of protein tyrosine kinase(s)," *J. Pharm. And Experimental Therapeutics*, 1993, 267(3), 1119-1125.

Schafer, A. J., et al., "DNA variation and the future of human genetics," *Nature Biotechnology*, 1998, 16, 33-39.

Schroeder, K. S., et al., "FLIPR: A new instrument for accurate, high throughput optical screening," *J. Biomolecular Screening*, 1996, 1, 75-80.

Sculier, J. P., et al., "Role of an intensive care unit (ICU) in a medical oncology department," No. 257, *Cancer Immunol. And Immunotheter.*, 1986, 23, A65.

Segal, D. J., et al., "Toward controlling gene expression at will: Selection and design of zinc finger domains recognizing each of the 5'-GNN-3' DNA target sequences," *Proc. Natl. Acad. Sci. USA*, 1999, 96, 2758-2763.

Shaw, S. H., et al., "A Genome—Wide Search for Schizophrenia Susceptibility Genes," *Amer. J. of Med. Genet. (Neuropsych. Genet.* ), 1998, 81, 364-376.

Shimada et al., "Mice lacking melanin-concentrating hormone are hypophagic and lean", *Nature*, 1998, 396, 670-673.

Shumaker, J. M., et al., "*Mutation detection by solid phase primer extension*," Hum. Mutat., 1996, 7, 346-354.

Sikora, E., et al., "Quinazoline CB 3717 and CB 3703 inhibition of folate retention and metabolism in ehrlich ascites carcinoma cells and some organs of the host-mouse," *Cancer Letters*, 1984, 23, 289-295.

Sikora, E., et al., "Development of an assay for the estimation of $N^{10}$-propargyl-5,8-dideazafolic acid polyglutamates in tumor cells," *Analytical Biochemistry*, 1988, 172, 344-355.

Sim, L. J., et al., "Identification of opioid receptor-like (ORL1) peptide-stimulated [$^{35}$S]GTPγS binding in rat brain," *Neuroreport*, 1996, 7, 729-733.

Smith, T. F., et al., "Comparison of biosequences," *Adv. Appl. Math.*, 1981, 2, 482-489.

Smith-Swintosky, V. L., et al., "protease-activated receptor-2(PAR-2_is present in the rat hippocampus and is associated with neurodegeneration," *J. Neurocham*, 1997, 69, 1890-1896.

Sonnhammer, E., et al., "A hidden markov model for predicting transmembrane helics in protein sequences," Glasgow, J., et al. (Eds.), *ISMB*, 1998, 6, 175-182.

Stables, J., et al., "A bioluminescent assay for agonist activity at potentially any G-protein-coupled receptor," *Analytical Biochemistry*, 1997, 252, 115-126.

Steen, B. et al., "Matrix metalloproteinases and metalloproteinase inhibitors in choroidal neovascular membranes", *Invest. Ophthalmol. Vis. Sci.*, 1998, 39(11), 2194-2200.

Stratowa, C., et al., "Use of a luciferase reporter system for characterizing G-protein-linked receptors," *Current Opinion in Biotechnology*, 1995, 6, 574-581.

SteinmannNiggli, K. et al., "Rat mesangial cells and matrix metalloproteinase inhibitor: Inhibition of 72-kD type IV collagenase (MMP-2) and of cell proliferation", *J. Am Soc. Nephrol.*, 1997, 8, 395-405.

Strosberg, et al., "Functional expression of receptors in microorganisms," *Trends in Pharmacological Sciences*, 1992, 13, 95-98.

Strosberg, A. D., et al., "Structure/function relationship of proteins belonging to the family of receptors coupled to GTP-binding proteins,," *Eur. J. Biochem.*, 1991, 196, 1-10.

Suidan, H. A., et al., "The thrombin receptor in the nervous system," *Semin Thromb Hemost*, 1996, 22(2), 125-133.

Summers, et al., *A Manual of Methods for Baculovirus Vectors and Insect Cell Culture Procedures*,Texas Agricultural Experimental Station Bulletin No. 1555, 1987, 2-46.

Sutherland, E. W., et al., "Some aspects of the biological role of adenosine 3',5'-monophosphate (cyclic AMP)," *Circulation*, 1968, 37, 279-306.

Sweetnam, P. M., et al., "The role of receptor binding in drug discovery," *J. Natural Products*, 1993, 56(4), 441-455.

Tempest, P. R., et al., "Reshaping a human monoclonal antibody to inhibit human respiratory syncytial virus infection *in vivo*," *Bio/Technology*, 1991, 9, 266-271.

Trejo, J., et al., "The cloned thrombin receptor is necessary and sufficient for activation of mitogen-activated protein kinase and mitogenesis in mouse lung fibroblasts," *J. Biol. Chem.*, 1996, 271, 21536-21541.

Turgeon, V. L., et al., "Thrombin perturbs neurite outgrowth and induces apoptotic cell death in enriched chick spinal motoneuron cultures through caspase activation," *J. Neurosci*, 1998, 18(17), 6882-6891.

Ubl, J. J., et al., "Characteristics of thrombin-induced calcium signals in rat astrocytes," *Glia*, 1997, 21, 361-369.

Vanden Broeck, "G-protein-coupled receptors in insect cells", *Int. Rev. Cytology*, 1996, 164, 189-268.

Verhoeyen, M., et al., "reshaping human antibodies: Grafting an antilysozyme activity," *Science*, 1988, 239, 1534-1536.

Verma, I. M., "Gene therapy," *Scientific American*, 1990, 68-84 (pp. 73-80 and 83 are advertisements).

Walder, R. Y., et al., "Oligodeoxynucleotide-directed mutagenesis using the yeast transformation system," *Gene*, 1986, 42, 133-139.

White, M. B., et al., "Detecting single base substitutions as heteroduplex polymorphisms," *Genomics*, 1992, 12, 301-306.

Whiteford, H. A., et al., "Mianserin-Induced Up-Regulation of Serotonin Receptors on Normal Human Platelets *in Vivo*," *Life Sciences*, 1993, 53(4), 371-376.

Wieboldt, R., et al., "Immunoaffinity ultrafiltration with ion spray HPLC/MS for screening small-molecule libraries," *Anal. Chem.*, 1997, 69(9), 1683-1691.

Williams, M., "Receptor binding in the drug discovery process," *Medicinal Research Reviews*, 1991, 11(2), 147-184.

Wolbring, G., et al., "Inhibition of GTP-utilizing enzymes by tyrphostins," *J. Biol. Chem.*, 1994, 269(36), 22470-22472.

Wu, H., et al., "Building zinc fingers by selection: toward a therapeutic applications," *Proc. Natl. Acad. Sci. USA*, 1995, 92, 344-348.

Yoneda, T., et al., "The antiproliferative effects of tyrosine kinase inhibitors tyrphostins on a human squamous cell carcinoma in vitro and in nude mice," *Cancer Research*, 1991, 51, 4430-4435.

Young, D., et al., "Isolation and Characterization of a New Cellular Oncogene Encoding a Protein with Multiple Potential Transmembrane Domains," *Cell*, 1986, 45, 711-719.

Zempo, N. et al., "Regulation of vascular smooth muscle cell migration and proliferation in vitro and in injured rat arteries by a synthetic matrix metallproteinase inhibitor", *Artherioscler. Thromb. Vasc. Biol.*, 1996, 16(1), 28-33.

Zeng, Z., et al., "Cloning of a Putative Human Neurotransmitter Receptor Expression in Skeletal Muscle and Brain," *Biochem. & Biophys. Resear. Commun.*, 1998, 242, 575-578 (Article No. RC977591).

Ausbel, et al. (Eds.), *Current Protocols in Molecular Biology*, New York, 1987-1999, John Wiley & Sons, Inc.

Berger et al., "Guide to Molecular Cloning Techniques," in *Methods in Enzymology*, Academic Press, Inc., San Diego, CA, 1987.

Eisenthal, R. et al., in *Enzyme Assays: A Practical Approach*, Oxford University Press, 1992.

Harlow, E. et al., in *ANTIBODIES: A Laboratory Manual*, Cold Spring Harbor Laboratory, Cold Spring Harbor, NY, 1988, Chapter 6.

Henrdix, R. W. (ed.), *Lambda II*, Cold Spring Harbor Press, Cold Spring Harbor, NY, 1980.

Hershey, A. D. (ed.), *The Bacteriophage Lambda*, Cold Spring Harbor Press, Cold Spring Harbor, NY, 1973.

Kruse et al. (eds.), in *Tissue Culture*, Academic Press, 1973.

O'Rielly et al. (ed.), in *Baculovirus Expression Vectors: A Laboratory Manual*, W.H. Freeman and Company, New York, 1992.

Osol, A (ed.), in *Remington's Pharmaceutical Sciences*, 16th edition, 1980.

Sambrook et al., in *Molecular Cloning: A Laboratory Manual*, second edition, Cold Spring Harbor Press, Cold Spring Harbor, NY, 1989.

Summers et al., A Manual of Methods for Baculovirus Vectors and Insect Cell Culture Procedures, Texas Agricultural Experimental Station Bulletin No. 1555, 1987.

Yang, M., et al., "Cloning and characterization of a novel matrix metalloproteinase, (MMP), CMMP, from chicken embryo fibroblasts," *J. Biological Chemistry*, 1998, 273(28), 17893-17900.

Yoshiyama, Y., et al., "Selective distribution of matrix metalloproteinase-3 (MMP-3) in alzheimer's disease brain," *Acta Meirp[atjp;*, 2000, 99, 91-95.

Invitation to Pay Additional Fees with Partial Search Report dated Apr. 2, 2002 (PCT/US01/16563).

Shapiro, S.D., et al., "Cloning and characterization of a unique elastolytic metalloproteinase produced by human alveolar macrophages," *J. Biol. Chem.*, 1993, 268(32), 23824-23829 (XP00056434 and XP-002203714).

Strausberg, R., "Matrix mallopteinase-14," *Database EMBL Online*, Mar. 7, 2000, Accession No. AW519125, 1 page (XP-002203713).

PCT International Search Report dated Jul. 16, 2002 (PCT/US01/16563).

Ausubel, F.M., (ed.) Current Protocols in Molecular Biology, Wiley and Sons, New York, vol. 3, 1988.

Berger, S.B. and A.R. Kimmel, (eds.) Guide to Molecular Cloning Techniques, Methods in Enzymology, Academic Press, San Diego, 1987, pp. 49-54, 215-219 and 227-234.

Eisenthal, R. and M.J. Danson, (eds.), Enzyme Assays: A Practical Approach, Oxford University Press, 1992, pp. 1-376.

* cited by examiner

SEQUENCE LISTING

```
<160> NUMBER OF SEQ ID NOS: 8

<210> SEQ ID NO 1
<211> LENGTH: 1845
<212> TYPE: DNA
<213> ORGANISM: Homo sapiens

<400> SEQUENCE: 1
gcttcagctg aagaaagaga ggaatgaagc gccttctgct tctgtgtttg ttctttataa        60
cattttcttc tgcatttccc ttagtccgga tgacggaaaa tgaagaaaat atgcaactgg       120
ctcaggcata tctcaaccag ttctactctc ttgaaataga agggaatcat cttgttcaaa       180
gcaagaatag gagtctcata gatgacaaaa ttcgggaaat gcaagcattt tttggattga       240
cagtgactgg aaaactggac tcaaacaccc ttgagatcat gaagacaccc aggtgtgggg       300
tgcctgatgt gggccagtat ggctacaccc tccctgggtg gagaaaatac aacctcacct       360
acagaataat aaactatact ccggatatgg cacgagctgc tgtggatgag gctatccaag       420
aaggtttaga agtgtggagc aaagtcactc cactaaaatt caccaagatt tcaaagggga       480
ttgcagacat catgattgcc tttaggactc gagtccatgg tcggtgtcct cgctattttg       540
atggtcccct gggagtgctt ggccatgcct ttcctcctgg tccgggtctg ggtggtgaca       600
ctcattttga tgaggatgaa aactggacca aggatgagc aggattcaac ttgtttcttg       660
tggctgctca tgaatttggt catgcactgg ggctctctca ctccaatgat caaacagcct       720
tgatgttccc aaattatgtc tccctggatc cagaaaaata cccactttct caggatgata       780
tcaatggaat ccagtccatc tatggaggtc tgcctaaggt acctgctaag ccaaaggaac       840
ccactatacc ccatgcctgt gaccctgact tgactttga cgctatcaca actttccgca       900
gagaagtaat gttctttaaa ggcaggcacc tatggaggat ctattatgat atcacggatg       960
ttgagtttga attaattgct tcattctggc catctctgcc agctgatctg caagctgcat      1020
```

| | | | | | |
|---|---|---|---|---|---|
| acgagaaccc | cagagataag | attctggttt | ttaaagatga | aaacttctgg | atgatcagag | 1080 |
| gatatgctgt | cttgccagat | tatcccaaat | ccatccatac | attaggtttt | ccaggacgtg | 1140 |
| tgaagaaaat | agatgcagcc | gtctgtgata | agaccacaag | aaaaacctac | ttctttgtgg | 1200 |
| gcatttggtg | ctggaggttt | gatgaaatga | cccaaaccat | ggacaaagga | ttcccgcaga | 1260 |
| gagtggtaaa | acactttcct | ggaatcagta | tccgtgttga | tgctgctttc | cagtacaaag | 1320 |
| gattcttctt | tttcagccgt | ggatcaaagc | aatttgaata | caacattaag | acaaagaata | 1380 |
| ttacccgaat | catgagaact | aatacttggt | ttcaatgcaa | agaaccaaag | aactcctcat | 1440 |
| ttggttttga | tatcaacaag | gaaaagcac | attcaggagg | cataaagata | ttgtatcata | 1500 |
| agagtttaag | cttgtttatt | tttggtattg | ttcatttgct | gaaaaacact | tctatttatc | 1560 |
| aataaattca | tagacctaaa | ataaacctca | acaggtcttt | taatataaat | tctgcttcaa | 1620 |
| aatagaataa | aaccattctt | taacaacaag | ttgctggtcc | tagttctaaa | tatccaaatt | 1680 |
| caatggccat | tttgagctgc | ctgattcttt | taataggaag | ttattatgta | gaaacaaaaa | 1740 |
| tctctgactg | tactttaagc | ctatttcatg | ctttgtggac | ttggagaaga | catgtcttat | 1800 |
| aactgaatac | tgaaacattt | attaaaccaa | tctttagcat | tctaa | | 1845 |

<210> SEQ ID NO 2
<211> LENGTH: 989
<212> TYPE: DNA
<213> ORGANISM: Homo sapiens

<400> SEQUENCE: 2

| | | | | | |
|---|---|---|---|---|---|
| gacaaatgag | ggtttggcat | gcagctcgtc | atcttaagag | ttactatctt | cttgccctgg | 60 |
| tgtttcgccg | ttccagtgcc | ccctgctgca | gaccataaag | gatgggactt | tgttgagggc | 120 |
| tatttccatc | aattttcct | gaccaagaag | gagtcgccac | tccttaccca | ggagacacaa | 180 |
| acacagctcc | tgcaacaatt | ccatcggaat | gggacagacc | tacttgacat | gcagatgcat | 240 |
| gctctgctac | accagcccca | ctgtggggtg | cctgatgggt | ccgacacctc | catctcgcca | 300 |
| ggaagatgca | agtggaataa | gcacactcta | acttacagga | ttatcaatta | cccacatgat | 360 |
| atgaagccat | ccgcagtgaa | agacagtata | tataatgcag | tttccatctg | gagcaatgtg | 420 |
| acccctttga | tattccagca | agtgcagaat | ggagatgcag | acatcaaggt | ttctttctgg | 480 |
| cagtgggccc | atgaagatgg | ttggcccttt | gatgggccag | gtggtatctt | aggccatgcc | 540 |
| ttttaccaa | attctggaaa | tcctggagtt | gtccattttg | acaagaatga | acactggtca | 600 |
| gcttcagaca | ctggatataa | tctgttcctg | gttgcaactc | atgagattgg | gcattctttg | 660 |
| ggcctgcagc | actctgggaa | tcagagctcc | ataatgtacc | ccacttactg | gtatcacgac | 720 |
| cctagaacct | tccagctcag | tgccgatgat | atccaaagga | tccagcattt | gtatggagaa | 780 |
| aaatgttcat | ctgacatacc | ttaatgttag | cacagaggca | ttattcaacc | tgtcctttca | 840 |
| gggagtttat | tggaggatca | agaactgaa | agcactagag | cagccttggg | gactgctagg | 900 |
| atgaagccct | aaagaatgca | acctagtcag | gttagctgaa | ccgacactca | aaacgctact | 960 |
| gagtcacaat | aaagattgtt | ttaaagagt | | | | 989 |

<210> SEQ ID NO 3
<211> LENGTH: 1597
<212> TYPE: DNA
<213> ORGANISM: Homo sapiens

<400> SEQUENCE: 3

```
gctccccgag ccgggctgca ccggaggcgg cgagatggtc gcgcgcgtcg gcctcctgct   60
gcgcgccctg cagctgctac tgtggggcca cctggacgcc cagcccgcgg agcgcggagg  120
ccaggagctg cgcaaggagg cggaggcatt cctagagaag tacgatacct caatgaaca  180
ggtccccaaa gctcccacct ccactcgatt cagcgatgcc atcagagcgt ttcagtgggt  240
gtcccagcta cctgtcagcg gcgtgttgga ccgcgccacc ctgcgccaga tgactcgtcc  300
ccgctgcggg gttacagata ccaacagtta tgcggcctgg gctgagagga tcagtgactt  360
gtttgctaga caccggacca aaatgaggcg taagaaacgc tttgcaaagc aaggtaacaa  420
atggtacaag cagcacctct cctaccgcct ggtgaactgg cctgagcatc tccggagccg  480
gcagttcggg gcgccgtgcg cgccgccttc cagttgtgga gcaacgtctc agcgctggag  540
ttctgggagg ccccagccac aggccccgct gacatccggc tcaccttctt ccaaggggac  600
cacaacgatg ggctgggcaa tgcctttgat ggcccagggg gcgccctggc cacgcctttt  660
cctgccccgc cgcggcgaag cgcacttcga ccaagatgag cgctggtccc tgagccgccg  720
ccgcgggcgc aacctgttcg tggtgctggc gcacgagatc ggtcacacgc ttggcctcac  780
ccactcgccc gcgccgcgcg cgctcatggc gccctactac aagaggctgg ccgcgacgc  840
gctgctcagc tgggacgacg tgctggccgt gcagagcctg tatgggaagc cctaggggg  900
ctcagtggcc gtccagctcc caggaaagct gttcactgac tttgagacct gggactccta  960
cagcccccaa ggaaggcgcc ctgaaacgca gggccctaaa tactgccact cttccttcga 1020
tgccatcact gtagacaggc aacagcaact gtacattttt aaagggagcc atttctggga 1080
ggtggcagct gatggcaacg tctcagagcc ccgtccactg caggaaagat gggtcgggct 1140
gccccccaac attgaggctg cggcagtgtc attgaatgat ggagatttct acttcttcaa 1200
aggggtcga tgctggaggt tccggggccc caagccagtg tgggtctcc cacagctgtg 1260
ccgggcaggg ggcctgcccc gccatcctga cgccgccctc ttcttccctc ctctgcgccg 1320
cctcatcctc ttcaagggtg cccgctacta cgtgctggcc cgagggggac tgcaagtgga 1380
gccctactac ccccgaagtc tgcaggactg ggaggcatc cctgaggagg tcagcggcgc 1440
cctgccgagg cccgatggct ccatcatctt cttccgagat accgctact ggcgcctcga 1500
ccaggccaaa ctgcaggcaa ccacctcggg ccgctgggcc accgagctgc ctggatggg 1560
ctgctggcat gccaactcgg ggagcgccct gttctga                         1597
```

<210> SEQ ID NO 4
<211> LENGTH: 513
<212> TYPE: PRT
<213> ORGANISM: Homo sapiens

<400> SEQUENCE: 4

```
Met Lys Arg Leu Leu Leu Cys Leu Phe Phe Ile Thr Phe Ser Ser
1               5                   10                  15

Ala Phe Pro Leu Val Arg Met Thr Glu Asn Glu Asn Met Gln Leu
                20                  25                  30

Ala Gln Ala Tyr Leu Asn Gln Phe Tyr Ser Leu Glu Ile Glu Gly Asn
            35                  40                  45

His Leu Val Gln Ser Lys Asn Arg Ser Leu Ile Asp Asp Lys Ile Arg
        50                  55                  60

Glu Met Gln Ala Phe Phe Gly Leu Thr Val Thr Gly Lys Leu Asp Ser
65                  70                  75                  80

Asn Thr Leu Glu Ile Met Lys Thr Pro Arg Cys Gly Val Pro Asp Val
                85                  90                  95
```

-continued

Gly Gln Tyr Gly Tyr Thr Leu Pro Gly Trp Arg Lys Tyr Asn Leu Thr
            100                 105                 110

Tyr Arg Ile Ile Asn Tyr Thr Pro Asp Met Ala Arg Ala Ala Val Asp
            115                 120                 125

Glu Ala Ile Gln Glu Gly Leu Glu Val Trp Ser Lys Val Thr Pro Leu
            130                 135                 140

Lys Phe Thr Lys Ile Ser Lys Gly Ile Ala Asp Ile Met Ile Ala Phe
145                 150                 155                 160

Arg Thr Arg Val His Gly Arg Cys Pro Arg Tyr Phe Asp Gly Pro Leu
                165                 170                 175

Gly Val Leu Gly His Ala Phe Pro Gly Pro Gly Leu Gly Gly Asp
            180                 185                 190

Thr His Phe Asp Glu Asp Glu Asn Trp Thr Lys Asp Gly Ala Gly Phe
            195                 200                 205

Asn Leu Phe Leu Val Ala Ala His Glu Phe Gly His Ala Leu Gly Leu
            210                 215                 220

Ser His Ser Asn Asp Gln Thr Ala Leu Met Phe Pro Asn Tyr Val Ser
225                 230                 235                 240

Leu Asp Pro Arg Lys Tyr Pro Leu Ser Gln Asp Asp Ile Asn Gly Ile
                245                 250                 255

Gln Ser Ile Tyr Gly Gly Leu Pro Lys Val Pro Ala Lys Pro Lys Glu
            260                 265                 270

Pro Thr Ile Pro His Ala Cys Asp Pro Asp Leu Thr Phe Asp Ala Ile
            275                 280                 285

Thr Thr Phe Arg Arg Glu Val Met Phe Phe Lys Gly Arg His Leu Trp
            290                 295                 300

Arg Ile Tyr Tyr Asp Ile Thr Asp Val Glu Phe Glu Leu Ile Ala Ser
305                 310                 315                 320

Phe Trp Pro Ser Leu Pro Ala Asp Leu Gln Ala Ala Tyr Glu Asn Pro
                325                 330                 335

Arg Asp Lys Ile Leu Val Phe Lys Asp Glu Asn Phe Trp Met Ile Arg
            340                 345                 350

Gly Tyr Ala Val Leu Pro Asp Tyr Pro Lys Ser Ile His Thr Leu Gly
            355                 360                 365

Phe Pro Gly Arg Val Lys Lys Ile Asp Ala Ala Val Cys Asp Lys Thr
            370                 375                 380

Thr Arg Lys Thr Tyr Phe Phe Val Gly Ile Trp Cys Trp Arg Phe Asp
385                 390                 395                 400

Glu Met Thr Gln Thr Met Asp Lys Gly Phe Pro Gln Arg Val Val Lys
                405                 410                 415

His Phe Pro Gly Ile Ser Ile Arg Val Asp Ala Ala Phe Gln Tyr Lys
            420                 425                 430

Gly Phe Phe Phe Ser Arg Gly Ser Lys Gln Phe Glu Tyr Asn Ile
            435                 440                 445

Lys Thr Lys Asn Ile Thr Arg Ile Met Arg Thr Asn Thr Trp Phe Gln
450                 455                 460

Cys Lys Glu Pro Lys Asn Ser Ser Phe Gly Phe Asp Ile Asn Lys Glu
465                 470                 475                 480

Lys Ala His Ser Gly Gly Ile Lys Ile Leu Tyr His Lys Ser Leu Ser
                485                 490                 495

Leu Phe Ile Phe Gly Ile Val His Leu Leu Lys Asn Thr Ser Ile Tyr
            500                 505                 510

-continued

Gln

<210> SEQ ID NO 5
<211> LENGTH: 259
<212> TYPE: PRT
<213> ORGANISM: Homo sapiens

<400> SEQUENCE: 5

Met Gln Leu Val Ile Leu Arg Val Thr Ile Phe Leu Pro Trp Cys Phe
1               5                   10                  15

Ala Val Pro Val Pro Pro Ala Ala Asp His Lys Gly Trp Asp Phe Val
            20                  25                  30

Glu Gly Tyr Phe His Gln Phe Phe Leu Thr Lys Lys Glu Ser Pro Leu
        35                  40                  45

Leu Thr Gln Glu Thr Gln Thr Gln Leu Leu Gln Gln Phe His Arg Asn
    50                  55                  60

Gly Thr Asp Leu Leu Asp Met Gln Met His Ala Leu Leu His Gln Pro
65                  70                  75                  80

His Cys Gly Val Pro Asp Gly Ser Asp Thr Ser Ile Ser Pro Gly Arg
                85                  90                  95

Cys Lys Trp Asn Lys His Thr Leu Thr Tyr Arg Ile Ile Asn Tyr Pro
            100                 105                 110

His Asp Met Lys Pro Ser Ala Val Lys Asp Ser Ile Tyr Asn Ala Val
        115                 120                 125

Ser Ile Trp Ser Asn Val Thr Pro Leu Ile Phe Gln Gln Val Gln Asn
    130                 135                 140

Gly Asp Ala Asp Ile Lys Val Ser Phe Trp Gln Trp Ala His Glu Asp
145                 150                 155                 160

Gly Trp Pro Phe Asp Gly Pro Gly Gly Ile Leu Gly His Ala Phe Leu
                165                 170                 175

Pro Asn Ser Gly Asn Pro Gly Val Val His Phe Asp Lys Asn Glu His
            180                 185                 190

Trp Ser Ala Ser Asp Thr Gly Tyr Asn Leu Phe Leu Val Ala Thr His
        195                 200                 205

Glu Ile Gly His Ser Leu Gly Leu Gln His Ser Gly Asn Gln Ser Ser
    210                 215                 220

Ile Met Tyr Pro Thr Tyr Trp Tyr His Asp Pro Arg Thr Phe Gln Leu
225                 230                 235                 240

Ser Ala Asp Asp Ile Gln Arg Ile Gln His Leu Tyr Gly Glu Lys Cys
                245                 250                 255

Ser Ser Asp

<210> SEQ ID NO 6
<211> LENGTH: 520
<212> TYPE: PRT
<213> ORGANISM: Homo sapiens

<400> SEQUENCE: 6

Met Val Ala Arg Val Gly Leu Leu Leu Arg Ala Leu Gln Leu Leu Leu
1               5                   10                  15

Trp Gly His Leu Asp Ala Gln Pro Ala Glu Arg Gly Gly Gln Glu Leu
            20                  25                  30

Arg Lys Glu Ala Glu Ala Phe Leu Glu Lys Tyr Gly Tyr Leu Asn Glu
        35                  40                  45

Gln Val Pro Lys Ala Pro Thr Ser Thr Arg Phe Ser Asp Ala Ile Arg
    50                  55                  60

```
Ala Phe Gln Trp Val Ser Gln Leu Pro Val Ser Gly Val Leu Asp Arg
 65                  70                  75                  80

Ala Thr Leu Arg Gln Met Thr Arg Pro Arg Cys Gly Val Thr Asp Thr
                 85                  90                  95

Asn Ser Tyr Ala Ala Trp Ala Glu Arg Ile Ser Asp Leu Phe Ala Arg
                100                 105                 110

His Arg Thr Lys Met Arg Arg Lys Lys Arg Phe Ala Lys Gln Gly Asn
                115                 120                 125

Lys Trp Tyr Lys Gln His Leu Ser Tyr Arg Leu Val Asn Trp Pro Glu
            130                 135                 140

His Leu Arg Ser Arg Gln Phe Gly Ala Pro Cys Ala Pro Pro Ser Ser
145                 150                 155                 160

Cys Gly Ala Thr Ser Gln Arg Trp Ser Ser Gly Arg Pro Gln Pro Gln
                165                 170                 175

Ala Pro Leu Thr Ser Gly Ser Pro Ser Ser Lys Gly Thr Thr Thr Met
                180                 185                 190

Gly Trp Ala Met Pro Leu Met Ala Gln Gly Ala Pro Trp Arg Thr Pro
            195                 200                 205

Phe Leu Pro Arg Arg Gly Glu Ala His Phe Asp Gln Asp Glu Arg Trp
    210                 215                 220

Ser Leu Ser Arg Arg Arg Gly Arg Asn Leu Phe Val Leu Ala His
225                 230                 235                 240

Glu Ile Gly His Thr Leu Gly Leu Thr His Ser Pro Ala Pro Arg Ala
                245                 250                 255

Leu Met Ala Pro Tyr Tyr Lys Arg Leu Gly Arg Asp Ala Leu Leu Ser
            260                 265                 270

Trp Asp Asp Val Leu Ala Val Gln Ser Leu Tyr Gly Lys Pro Leu Gly
            275                 280                 285

Gly Ser Val Ala Val Gln Leu Pro Gly Lys Leu Phe Thr Asp Phe Glu
290                 295                 300

Thr Trp Asp Ser Tyr Ser Pro Gln Gly Arg Arg Pro Glu Thr Gln Gly
305                 310                 315                 320

Pro Lys Tyr Cys His Ser Ser Phe Asp Ala Ile Thr Val Asp Arg Gln
                325                 330                 335

Gln Gln Leu Tyr Ile Phe Lys Gly Ser His Phe Trp Glu Val Ala Ala
            340                 345                 350

Asp Gly Asn Val Ser Glu Pro Arg Pro Leu Gln Glu Arg Trp Val Gly
            355                 360                 365

Leu Pro Pro Asn Ile Glu Ala Ala Val Ser Leu Asn Asp Gly Asp
    370                 375                 380

Phe Tyr Phe Phe Lys Gly Gly Arg Cys Trp Arg Phe Arg Gly Pro Lys
385                 390                 395                 400

Pro Val Trp Gly Leu Pro Gln Leu Cys Arg Ala Gly Gly Leu Pro Arg
                405                 410                 415

His Pro Asp Ala Ala Leu Phe Phe Pro Pro Leu Arg Arg Leu Ile Leu
                420                 425                 430

Phe Lys Gly Ala Arg Tyr Tyr Val Leu Ala Arg Gly Gly Leu Gln Val
            435                 440                 445

Glu Pro Tyr Tyr Pro Arg Ser Leu Gln Asp Trp Gly Gly Ile Pro Glu
            450                 455                 460

Glu Val Ser Gly Ala Leu Pro Arg Pro Asp Gly Ser Ile Ile Phe Phe
465                 470                 475                 480
```

```
Arg Asp Asp Arg Tyr Trp Arg Leu Asp Gln Ala Lys Leu Gln Ala Thr
                485                 490                 495

Thr Ser Gly Arg Trp Ala Thr Glu Leu Pro Trp Met Gly Cys Trp His
            500                 505                 510

Ala Asn Ser Gly Ser Ala Leu Phe
            515                 520

<210> SEQ ID NO 7
<211> LENGTH: 999
<212> TYPE: DNA
<213> ORGANISM: Homo sapiens
<300> PUBLICATION INFORMATION:
<301> AUTHORS: Park, H.I., Ni, J., Gerkema, F.E., Liu, D., Belozero
              Sang, Q.X.
<302> TITLE: Identification and characterization of human
             endometalloproteinase-26) from endometrial tumor
<303> JOURNAL: J. Biol. Chem.
<304> VOLUME: 275
<305> ISSUE: 27
<306> PAGES: 20540-20544
<307> DATE: 2000-03-23
<308> DATABASE ACCESSION NUMBER: GenBankAF248646
<309> DATABASE ENTRY DATE: 2000-03-23
<300> PUBLICATION INFORMATION:
<308> DATABASE ACCESSION NUMBER: GenbankAF248646
<309> DATABASE ENTRY DATE: 2000-03-23

<400> SEQUENCE: 7
ggcacgagca tgcagctcgt catcttaaga gttactatct tcttgccctg gtgtttcgcc      60
gttccagtgc cccctgctgc agaccataaa ggatgggact tgttgagggg ctatttccat     120
caatttttcc tgaccgagaa ggagtcgcca ctccttaccc aggagacaca aacacagctc     180
ctgcaacaat tccatcggaa tgggacagac tacttgaca tgcagatgca tgctctgcta      240
caccagcccc actgtggggt gcctgatggg tccgacacct ccatctcgcc aggaagatgc     300
aagtggaata agcacactct aacttacagg attatcaatt acccacatga tatgaagcca     360
tccgcagtga agacagtat atataatgca gtttccatct ggagcaatgt gacccctttg      420
atattccagc aagtgcagaa tggagatgca gacatcaagg tttctttctg gcagtgggcc     480
catgaagatg gttggccctt tgatgggcca ggtggtatct taggccatgc ctttttacca     540
aattctggaa atcctggagt tgtccatttt gacaagaatg aacactggtc agcttcagac     600
actggatata atctgttcct ggttgcaact catgagattg gcattctttt gggcctgcag     660
cactctggga atcagagctc cataatgtac cccacttact ggtatcacga ccctagaacc     720
ttccagctca gtgccgatga tatccaaagg atccagcatt tgtatggaga aaaatgttca     780
tctgacatac cttaatgtta gcacagagga cttattcaac ctgtctttca gggagtttat     840
tggaggatca aagaactgaa agcactagag cagccttggg gactgctagg atgaagccct    900
aaagaatgca acctagtcag gttagctgaa ccgacactca aaacgctact gagtcacaat    960
aaagattgtt ttaaagagta aaaaaaaaaa aaaaaaaa                             999

<210> SEQ ID NO 8
<211> LENGTH: 261
<212> TYPE: PRT
<213> ORGANISM: Homo sapiens
<300> PUBLICATION INFORMATION:
<301> AUTHORS: Park, H.I., Ni, J., Gerkema, F.E., Liu, D., Belozero
              Sang, Q.X.
<302> TITLE: Identification and characterization of human
             endometalloproteinase-26) from endometrial tumor
<303> JOURNAL: J. Biol. Cehm.
<304> VOLUME: 275
<305> ISSUE: 27
```

```
-continued

<306> PAGES: 20540-205444
<307> DATE: 2000-03-23
<308> DATABASE ACCESSION NUMBER: GenBankAF248626
<309> DATABASE ENTRY DATE: 2001-03-23
<300> PUBLICATION INFORMATION:
<308> DATABASE ACCESSION NUMBER: GenbankAF248646
<309> DATABASE ENTRY DATE: 2000-03-23

<400> SEQUENCE: 8

Met Gln Leu Val Ile Leu Arg Val Thr Ile Phe Leu Pro Trp Cys Phe
1               5                   10                  15

Ala Val Pro Val Pro Pro Ala Ala Asp His Lys Gly Trp Asp Phe Val
            20                  25                  30

Glu Gly Tyr Phe His Gln Phe Phe Leu Thr Glu Lys Glu Ser Pro Leu
        35                  40                  45

Leu Thr Gln Glu Thr Gln Thr Gln Leu Leu Gln Gln Phe His Arg Asn
    50                  55                  60

Gly Thr Asp Leu Leu Asp Met Gln Met His Ala Leu Leu His Gln Pro
65                  70                  75                  80

His Cys Gly Val Pro Asp Gly Ser Asp Thr Ser Ile Ser Pro Gly Arg
                85                  90                  95

Cys Lys Trp Asn Lys His Thr Leu Thr Tyr Arg Ile Ile Asn Tyr Pro
            100                 105                 110

His Asp Met Lys Pro Ser Ala Val Lys Asp Ser Ile Tyr Asn Ala Val
        115                 120                 125

Ser Ile Trp Ser Asn Val Thr Pro Leu Ile Phe Gln Gln Val Gln Asn
    130                 135                 140

Gly Asp Ala Asp Ile Lys Val Ser Phe Trp Gln Trp Ala His Glu Asp
145                 150                 155                 160

Gly Trp Pro Phe Asp Gly Pro Gly Gly Ile Leu Gly His Ala Phe Leu
                165                 170                 175

Pro Asn Ser Gly Asn Pro Gly Val Val His Phe Asp Lys Asn Glu His
            180                 185                 190

Trp Ser Ala Ser Asp Thr Gly Tyr Asn Leu Phe Leu Val Ala Thr His
        195                 200                 205

Glu Ile Gly His Ser Leu Gly Leu Gln His Ser Gly Asn Gln Ser Ser
    210                 215                 220

Ile Met Tyr Pro Thr Tyr Trp Tyr His Asp Pro Arg Thr Phe Gln Leu
225                 230                 235                 240

Ser Ala Asp Asp Ile Gln Arg Ile Gln His Leu Tyr Gly Glu Lys Cys
                245                 250                 255

Ser Ser Asp Ile Pro
                260
```

MATRIX METALLOPROTEINASE POLYPEPTIDE

CROSS-REFERENCE TO RELATED APPLICATIONS

The present application is a divisional of application Ser. No. 09/862,631, filed May 22, 2001, which issued as U.S. Pat. No. 6,734,005 on May 11, 2004 and, which claims priority of application Ser. No. 60/206,119, filed May 22, 2000, each of which is hereby incorporated by reference in its entirety.

FIELD OF THE INVENTION

The present invention relates generally to the fields of genetics and cellular and molecular biology. More particularly, the invention relates to novel matrix metalloproteinases.

BACKGROUND OF THE INVENTION

Matrix metalloproteinases (MMPs; matrixins) comprise a family of structurally related Zn-containing proteases that degrade all macromolecules present in the extracellular matrix (ECM). Each of the known MMPs can be divided up into a variable number of well-conserved domains. All contain a pro-peptide which is involved in suppressing the activity of the pro-enzyme form of the molecule, and a HEXXH sequence motif that has been shown by X-ray crystallography to form part of the metal-binding site (Nagase et al. (1999) J. Biol. Chem., 274, 31, 21491–21494). In addition, fibronectin-, hemopexin-, or vitronectin-like domains and/or a membrane "anchor" domain may also be present.

Today, the MMP family includes more than 15 members (Table 1).

TABLE 1

Characteristics of known human MMPs

| MMP | Type | Substrate |
|---|---|---|
| MMP-1 | Collagenase | collagen I, II, III, VII, X gelatins |
| MMP-2 | Gelatinase B | collagens IV, V, VII, XI, fibronectin, elastin |
| MMP-3 | Stromelysin 1 | proteoglycans, gelatins, fibronectin, collagens II, IV, IX |
| MMP-7 | Matrilysin | Proteoglycans, gelatins, collagen IV, elastin |
| MMP-8 | Neutrophil collagenase | collagens I, II, III |
| MMP-9 | Gelatinase B | gelatins, collagen IV, V, proteoglycan, elastin |
| MMP-10 | Stromelysin 2 | proteoglycan, fibronectin, laminin |
| MMP-12 | Macrophage elastase | proteoglycans, elastase |
| MMP-13 | Collagenase 3 | collagens I, II, III, IV |

MMPs are believed to play a critical role in many physiological and pathological processes. The breakdown of ECM by MMPs is essential for processes including embryonic development, morphogenesis, reproduction, and tissue repair and remodeling. Other physiological processes which involve MMPs include tumor growth, tumor invasion, Sjögren's syndrome, periodontal diseases, arthritis, cardiomyopathy, renal failure, atherosclerosis, insulin resistance, adipogenesis, retinal neovascularization, wound healing, and neurodegenerative diseases including, for example, Alzheimer's disease, multiple sclerosis, Parkinson's disease, and motoneuron disease. Identification of the functions of additional genes of the MMP family would be invaluable to those of skill in the art seeking to understand the genetic basis for these processes, as well as identifying compounds that modulate the activity of such genes useful in methods for treating the pathologies.

Tissue inhibitors of metalloproteinases (TIMPs) are a group of closely related secreted proteins that limit MMP activity. To date, four TIMPs have been characterized; TIMP1, TIMP2, TIMP3, and TIMP4, respectively (Gomez et al. (1997) Eur. J. Cell. Biol., 74, 111–122). Several investigators have studied effects of MMP inhibition by using cells over-expressing TIMPs. The balance between MMPs and TIMPs seems to play an important role in matrix turnover in several organ systems.

The past few years have witnessed several advances in the understanding of the pathophysiology of coronary atherosclerosis. The earliest atherosclerotic lesion, named the fatty streak, represents a dynamic balance of the entry and exit of lipoprotein as well as the development of extracellular matrix. A decrease in lipoprotein entry will probably result in a predominance of lipoprotein exit and final scarring. However, an increase of lipoprotein entry can predominate over the efflux and scarring, resulting in vulnerable lipid-rich plaques that are prone to disruption (Falk et al., (1995), Circulation, 92:657–671; Fuster et al., (1999), Lancet, 353: SII: 5–9).

It is evident from many studies that MMPs, as a family, are important regulators of atherosclerotic plaque growth (Newby et al., (1994), Basic Res. Cardiol. 89 [Suppl. 1] 59–70). However, the roles of the individual MMPs are so far largely unknown. Several MMPs are expressed in the diseased blood vessel, i.e. in smooth muscle cells and in macrophages. MMPs likely regulate both the degradation of extracellular matrix and influence the proliferation rate of smooth muscle cells. Several inflammatory cytokines and growth factors increase the expression of MMPs in cell cultures, e.g. interleukin-1, platelet-derived growth factor (PDGF) and tumor necrosis factor-α (TNF-α).

It has been demonstrated in several animal models that inhibition of MMPs (type 1 and 2 among others) decreases smooth muscle proliferation in response to vascular damage. Moreover, MMPs seem to enhance smooth muscle cell migration. These two physiological processes are hallmarks of the neointimal thickening that characterizes atherosclerosis. Accordingly, MMP inhibitors may delay or prevent spontaneous atherogenesis as well as restenosis. MMPs and/or TIMPs may be especially useful for patients at risk for atherosclerosis, dyslipidemia, end-stage renal failure, or patients who have undergone Percutaneous Transluminal Coronary Angioplasty Procedure (PTCA).

A large number of studies support a role of MMPs in intima media function. For example, over-expression of TIMP2 inhibits vascular smooth muscle cell proliferation and chemotaxis in vitro (Baker et al., (1998), J. Clin. Invest., 101: 1478–1487; Cheng et al., (1998), Circulation, 98:2195–2201). In addition, it has been shown that MMPs are linked to the proliferation and outgrowth of vascular smooth muscle cells from explants of rabbit aorta in vitro. The proliferation and outgrowth of vascular smooth muscle cells from rabbit aorta was blocked by experimental inhibitors (Ro 31-4724 and Ro 31-7467) (Newby et al., (1994). Batimastat (BB94), a synthetic MMP inhibitor, can reduce smooth muscle cell proliferation in vitro as well as inhibit neointimal formation after balloon injury to the rat carotid artery (Zempo et al., (1996), Artherioscler. Thromb. Vasc. Biol., 16:28–33). Local overexpression of TIMP1 has been shown to inhibit intimal hyperplasia in rats (Forough et al., (1996), Circ. Res., 79:812–820). After in vitro incubation with MMP-3, -7, or -12, the ability of HDL(3) to induce the high affinity component of cholesterol efflux from the macrophage foam cells was strongly reduced (Lindstedt et al., (1999), J. Biol. Chem., 274:22627–22634).

Angiogenesis, also known as neovascularization or new vessel growth, is part of the normal wound healing machinery and can occur as a reaction to tissue hypoxia. Various tumors are also known to trigger angiogenesis, leading to tumor growth. In normal adult tissue, there is a balance between angiogenic and anti-angiogenic factors and, as a result, few new vessels are formed. However, if the balance between angiogenic and anti-angiogenic factors is disturbed, a complex cascade of events can be triggered that eventually leads to the formation of new blood vessels.

Diabetic retinopathy is the leading cause of blindness for the majority of Americans. Microvascular damage from diabetes leads to microaneurysms, hemorrhage, exudates, and cotton-wool spots. Further progression of disease leads to neovascularization. Growth of new blood vessels can cause severe hemorrhage, scarring, and permanent visual loss (for a review, see Frank et al, (1996), South. Med. J., 89:463–470; Jampol & Goldbaum, (1980), Surv. Ophthalmol. 25:1–14). Various randomized, prospective studies have clearly shown benefit from laser therapy at specific stages of progression of retinopathy.

AMD with rapid progression (wet AMD) is another common cause of blindness in the developed world. Presently the underlying etiology of AMD is unknown but a slow deterioration of the retinal pigment epithelium, leading to the death of macular photoreceptors, is believed to be an important factor. The wet form of AMD often leads to a complete loss of central vision within a few years. AMD usually debuts in the dry form and may subsequently change into the wet form. AMD with rapid progression is characterized by choroidal new vessel formation (CNV). The new vessels tend to leak and may rupture. The resulting macular edema, bleeding, fibrinous deposits, and scar formation are reasons for the rapid deterioration of vision in this form of AMD.

Sprouting is a key step in CNV formation. If sprouting can be inhibited, no new leaky vessels will form. MMPs are essential to create space for the new sprouts. Because this step is downstream in the angiogenesis process, an MMP inhibitor can work to limit sprouting even if the earlier events are slightly different from those described above. The localization of MMP-2 and MMP-9 to the areas of new vessel formation and to the enveloping Bruch's-like membrane, respectively, suggests that MMP-2 and MMP-9 may be cooperatively involved in the progressive growth of choroidal neovascular membranes (Steen et al. (1998), Invest. Ophthalmol. Vis. Sci., 39:2194–2200). In normal individuals MMP-9 activity is not detected in the eye; however, it has been demonstrated that MMP-9 activity is detected in more than 80% of patients with "active" proliferative retinopathy (Kosano et al., (1999), Life Sci., 64:2307–2315).

MMP inhibitors present an attractive opening for prophylactic pharmacotherapy of ocular blood vessel proliferation in diabetes and AMD. Moreover, it may be possible to combine MMP inhibitors with photodynamic therapy. It is possible that inhibitors of MMPs could prevent recurrence of CNV and, thus, improve long-term efficacy. Patients are likely to accept certain side effects in order to preserve their vision, as most are aware that the disease will rapidly lead to blindness. Topical treatment is advantageous from a pharmacovigilance point-of-view.

MMPs are also involved in the bioacticvation of cytokines, including tumor necrosis factor-alpha (TNF-$\alpha$). Evidence suggests that TNF-$\alpha$ is a key mediator of insulin resistance in adipocytes and skeletal muscle. Inhibition of MMPs may decrease the formation rate of TNF-$\alpha$ and, accordingly, be of therapeutic significance in type-II diabetes. MMPs and/or TIMPS may be useful for patients with Type II diabetes or for obese patients with insulin resistance.

It has been suggested that TNF-$\alpha$ is an inducer of insulin resistance in type II diabetes. TNF-$\alpha$ is synthesized as a membrane-bound precursor that is proteolytically processed to an active form by a matrix metalloproteinase (MMP)-like enzyme. It has been shown that subcutaneous administration of KB-R7785 (a non-specific MMP inhibitor) to KKAy mice, which show insulin resistance and hyperglycemia for 4 weeks, resulted in a significant decrease in plasma glucose levels after 3 weeks of administration. In the same study it was also demonstrated that administration of pioglitazone significantly decreased plasma glucose levels. Interestingly, KB-R7785, but not pioglitazone, also significantly decreased plasma insulin levels in the animals. It has also been shown that the lipopolysaccharide-induction of TNF-$\alpha$ in plasma can be inhibited in KKAy mice by KB-R7785. These results suggest that MMP inhibitors may exert an anti-diabetic effect by ameliorating insulin sensitivity through the inhibition of TNF-$\alpha$ production.

Nephropathy in patients with type I and II diabetes mellitus is a rapidly increasing problem worldwide. Diabetic patients account for nearly half of all patients on hemodialysis. Microalbuminuria is diagnosed when the urinary albumin excretion rate is greater than 20 but less than 200 micrograms/min and the prevalence of microalbuminuria among diabetic patients is 15–20% (Deckert et al., (1992), Diabetes Care, 15:1181–1191).

MMP inhibitors (non-selective) have been found to decrease the proliferation rate of cultured rat mesangial cells without affecting cell viability. Therefore, MMP inhibitors may offer a new therapeutic approach for treatment of mesangial cell-derived forms of glomerulonephritis and prevent basal membrane thickening in diabetes. MMPs and/or TIMPS may be useful for diabetic patients with early signs of glomerulopathy, or for patients with microalbuminuria.

Progressive expansion of the mesangial matrix, and thickening of the glomerular and tubular basement membranes are hallmarks of human and experimental diabetic nephropathy (Philips et al. (1999), Kidney Blood Press. Res. 22:81–97; Young et al., (1995) Kidney Int., 47:935–944). These lesions eventually lead to glomerular fibrosis, a central pathological feature in many human acute and chronic kidney diseases, which progressively destroys the renal filtration unit, and may finally cause renal failure. It has been demonstrated that mesangial matrix expansion is strongly related to the clinical manifestation of diabetic nephropathy. Diabetic nephropathy is effected both directly and indirectly by the alteration of cytokine generation. Data from studies on several animal species suggest that proliferation of mesangial cells is an important feature of diabetic glomerulopathy. Harendza et al., (Nephrol. Dial. Transplant 12:2537–2541, (1997)) have demonstrated that the expression of MMP2 is enhanced in experimental proliferative glomerulopathy in the rat. Inhibition of MMP2 by Ro 31-9790 inhibited the proliferation rate of cultured rat mesangial cells in a concentration-dependent and at least partially reversible manner without affecting cell viability (Steinmann-Niggli K, et al., (1997), J. Am. Soc. Nephrol. 8:395–405). Moreover, Ebihara et al., ((1998) Am. J. Kidney Dis. 32:544–550) have reported that increased MMP9 concentrations in plasma preceded the occurrence of microalbuminuria in diabetic patients.

Thus, a need exists for new members of the MMP family of proteases.

SUMMARY OF THE INVENTION

The present invention addresses the need identified above by providing DNA sequences of genes encoding heretofore unknown members of the MMP family of proteases, bearing sequence homology and functional homology to MMPs; constructs and recombinant host cells incorporating the genes; the MMP polypeptides encoded by the genes; antibodies to the polypeptides; kits employing the polynucleotides and polypeptides, and methods of making and using all of the foregoing. Exemplary diseases and conditions amenable to treatment based on the present invention include, but are not limited to metabolic diseases and disorders (e.g., type 2 diabetes, obesity, cardiovascular, dyslipidemias, adipogenesis, retinopathies, neuropathies, nephropathies etc.), proliferative diseases and cancers (e.g., different cancers such as breast, colon, lung, etc., tumor growth, tumor invasion, and hyperproliferative disorders such as psoriasis, prostate hyperplasia, etc.), hormonal disorders (e.g., male/female hormonal replacement, polycystic ovarian syndrome, alopecia, etc.), CNS disorders (e.g., degenerative disorders such as Parkinson's, Alzheimer's, etc.), inflammatory conditions (e.g., Chron's disease, arthritis), diseases related to cell differentiation and homeostasis, cardiomyopathy, atherosclerosis, thromboembolic diseases, Sjögren's syndrome, renal failure, periodontal diseases, retinal neovascularization, wound healing, and neurodegenerative diseases including, for example, Alzheimer's disease, multiple sclerosis, Parkinson's disease, and motoneuron disease, among others.

In one embodiment, the invention provides purified and isolated MMP polypeptides comprising the amino acid sequence set forth in SEQ ID NOS: 4–6, or a fragment thereof comprising an epitope specific to the MMP polypeptide. Preferred embodiments comprise purified and isolated polypeptides comprising the complete amino acid sequences set forth in any of SEQ ID NOS: 4–6, found in Table 5 below. These amino acid sequences were deduced from the polynucleotide sequences encoding MMP—(SEQ ID NOS: 1–3 found in Table 5 below).

In another preferred embodiment, the invention provides a purified and isolated polypeptide comprising at least one conserved MMP domain.

In another embodiment, the invention provides purified and isolated polynucleotides (e.g., cDNA, genomic DNA, synthetic DNA, RNA, or combinations thereof, whether single- or double-stranded) that comprise a nucleotide sequence encoding the amino acid sequence of the polypeptides of the invention. Such polynucleotides are useful for recombinantly expressing the protease and also for detecting expression of the protease in cells (e.g., using Northern hybridization and in situ hybridization assays. Such polynucleotides also are useful in the design of antisense and other molecules for the suppression of the expression of MMPs in a cultured cell, a tissue, or an animal; for therapeutic purposes; or to provide a model for diseases or conditions characterized by aberrant MMP expression. Specifically excluded from the definition of polynucleotides of the invention are entire isolated, non-recombinant native chromosomes of host cells. Preferred polynucleotides have the sequences set forth in SEQ ID NOS: 1–3, which correspond to a naturally occurring MMP-sequences.

The invention also provides a purified and isolated polynucleotide comprising a nucleotide sequence that encodes a mammalian gene product, wherein the polynucleotide hybridizes to a polynucleotide having the sequences set forth in SEQ ID NOS: 1–3 or the non-coding strand complementary thereto, under the following hybridization conditions:

(a) hybridization for 16 hours at 42° C. in a hybridization solution comprising 50% formamide, 1% SDS, 1 M NaCl, 10% dextran sulfate; and (b) washing 2 times for 30 minutes each at 60° C. in a wash solution comprising 0.1% SSC, 1% SDS. Polynucleotides that encode a human allelic variant are highly preferred.

In a related embodiment, the invention provides vectors comprising a polynucleotide of the invention. Such vectors are useful, e.g., for amplifying the polynucleotides in host cells to create useful quantities thereof. In preferred embodiments, the vector is an expression vector wherein the polynucleotide of the invention is operatively linked to a polynucleotide comprising an expression control sequence. Such vectors are useful for recombinant production of polypeptides of the invention.

In another related embodiment, the invention provides host cells that are transformed or transfected (stably or transiently) with polynucleotides of the invention or vectors of the invention. Such host cells are useful for amplifying the polynucleotides and also for expressing the MMP polypeptides or fragments thereof encoded by the polynucleotides.

In still another related embodiment, the invention provides a method for producing MMP polypeptides (or fragments thereof) comprising the steps of growing a host cell of the invention in a nutrient medium and isolating the polypeptide or variant thereof from the cell or the medium.

In still another embodiment, the invention provides an antibody that is specific for the MMP of the invention. Antibody specificity is described in greater detail below. However, it should be emphasized that antibodies that can be generated from polypeptides that have previously been described in the literature and that are capable of fortuitously cross-reacting with MMP (e.g., due to the fortuitous existence of a similar epitope in both polypeptides) are considered "cross-reactive" antibodies. Such cross-reactive antibodies are not antibodies that are "specific" for MMP.

In one preferred variation, the invention provides monoclonal antibodies. Hybridomas that produce such antibodies also are intended as aspects of the invention. In yet another variation, the invention provides a humanized antibody. Humanized antibodies are useful for in vivo therapeutic indications.

In another variation, the invention provides a cell-free composition comprising polyclonal antibodies, wherein at least one of the antibodies is an antibody of the invention specific for MMP. Antisera isolated from an animal is an exemplary composition, as is a composition comprising an antibody fraction of an antisera that has been resuspended in water or in another diluent, excipient, or carrier.

In still another related embodiment, the invention provides an anti-idiotypic antibody specific for an antibody that is specific for MMP.

In still another embodiment, the invention provides a polypeptide comprising a fragment of an MMP-specific antibody, wherein the fragment and the polypeptide bind to the MMP. By way of non-limiting example, the invention provides polypeptides that are single chain antibodies and CDR-grafted antibodies.

Also within the scope of the invention are compositions comprising polypeptides, polynucleotides, or antibodies of the invention that have been formulated with, e.g., a pharmaceutically acceptable carrier.

The invention also provides methods of using antibodies of the invention. For example, the invention provides a method for modulating substrate binding of a MMP comprising the step of contacting the MMP with an antibody specific for the MMP, under conditions wherein the antibody binds the MMP.

MMPs may be expressed in various tissues, and an expression profile of such tissues provides additional uses for the invention. For example, if MMP is expressed in the brain, it would provide an indication that aberrant MMP activity may correlate with one or more neurological disorders. The invention thus also provides a method for treating a neurological disorder comprising the step of administering to a mammal in need of such treatment an amount of an antibody-like polypeptide of the invention that is sufficient to modulate substrate binding to a MMP in neurons of the mammal. MMP may also be expressed in other tissues, including but not limited to pancreas (and particularly pancreatic islet tissue), pituitary, skeletal muscle, adipose tissue, liver, and thyroid.

The invention also provides assays to identify compounds that bind a MMP. One such assay comprises the steps of: (a) contacting a composition comprising a MMP with a compound suspected of binding MMP; and (b) measuring binding between the compound and MMP. In one variation, the composition comprises a cell expressing MMP.

The invention also provides a method for identifying a modulator of binding between a MMP and a MMP binding partner, comprising the steps of: (a) contacting a MMP binding partner and a composition comprising a MMP in the presence and in the absence of a putative modulator compound; (b) detecting binding between the binding partner and the MMP; and (c) identifying a putative modulator compound or a modulator compound in view of decreased or increased binding between the binding partner and the MMP in the presence of the putative modulator, as compared to binding in the absence of the putative modulator.

MMP binding partners that stimulate MMP activity are useful as activators in disease states or conditions characterized by insufficient MMP activity. MMP binding partners that block MMP-mediated proteolysis are useful as MMP repressors to treat disease states or conditions characterized by excessive MMP-mediated proteolysis. In addition MMP proteolysis modulators in general, as well as MMP polynucleotides and polypeptides, are useful in diagnostic assays for such diseases or conditions.

In another aspect, the invention provides methods for treating a disease or abnormal condition by administering to a patient in need of such treatment a substance that modulates the activity or expression of MMP. Preferably, the disease is selected from the group consisting of tumor growth, tumor invasion, Sjögren's syndrome, periodontal diseases, arthritis, cardiomyopathy, renal failure, atherosclerosis, insulin resistance, adipogenesis, retinal neovascularization, wound healing, and neurodegenerative diseases including, for example, Alzheimer's disease, multiple sclerosis, Parkinson's disease, and motoneuron disease.

In another aspect, the invention features methods for detection of a polypeptide in a sample as a diagnostic tool for diseases or disorders, wherein the method comprises the steps of: (a) contacting the sample with a nucleic acid probe which hybridizes under hybridization assay conditions to a nucleic acid target region of a MMP polypeptide, said probe comprising the nucleic acid sequence encoding the polypeptide, fragments thereof, and the complements of the sequences and fragments; and (b) detecting the presence or amount of the probe:target region hybrid as an indication of the disease.

The diseases for which detection of genes in a sample could be diagnostic include diseases in which nucleic acid (DNA and/or RNA) is amplified in comparison to normal cells. The diseases that could be diagnosed by detection of nucleic acid in a sample preferably include cancers. The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample that is compatible with the method utilized.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations that are described herein as critical to the invention should be viewed as such; variations of the invention lacking limitations that have not been described herein as critical are intended as aspects of the invention.

DETAILED DESCRIPTION OF PREFERRED EMBODIMENTS

The present invention provides purified and isolated polynucleotides (e.g., DNA sequences and RNA transcripts, both sense and complementary antisense strands, both single- and double-stranded, including splice variants thereof) encoding a matrix metalloproteinase referred to herein as MMP. DNA polynucleotides of the invention include genomic DNA, cDNA, and DNA that has been chemically synthesized in whole or in part.

Definitions

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

"Synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means.

By the term "region" is meant a physically contiguous portion of the primary structure of a biomolecule. In the case of proteins, a region is defined by a contiguous portion of the amino acid sequence of that protein.

The term "domain" is herein defined as referring to a structural part of a biomolecule that contributes to a known or suspected function of the biomolecule. Domains may be co-extensive with regions or portions thereof; domains may also incorporate a portion of a biomolecule that is distinct from a particular region, in addition to all or part of that region.

As used herein, the terms "ligand" and "binding partner" are used interchangeably and refer to compounds that bind to proteases such as MMP or portions of such proteases.

Unless indicated otherwise, as used herein the abbreviation in lower case (mmp) refers to a gene, cDNA, RNA or nucleic acid sequence while the upper case version (MMP) refers to a protein, polypeptide, peptide, oligopeptide, or amino acid sequence.

As used herein, the term "activity" refers to a variety of measurable indicia suggesting or revealing binding, either direct or indirect; affecting a response, i.e. having a measurable affect in response to some exposure or stimulus, including, for example, the affinity of a compound for directly binding a polypeptide or polynucleotide of the invention, or, for example, measurement of amounts of upstream or downstream proteins or other similar functions after some stimulus or event.

As used herein, the term "antibody" is meant to refer to complete, intact antibodies, and Fab, Fab', F(ab)2, and other fragments thereof. Complete, intact antibodies include monoclonal antibodies such as murine monoclonal antibodies, chimeric antibodies and humanized antibodies.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates. Binding may be detected in many different manners. As a non-limiting example, the physical binding interaction between a MMP of the invention and a compound can be detected using a labeled compound. Alternatively, functional evidence of binding can be detected using, for example, a cell transfected with and expressing an MMP of the invention. Binding of the transfected cell to a ligand of the MMP that was transfected into the cell provides functional evidence of binding. Other methods of detecting binding are well known to those of skill in the art.

As used herein, the term "compound" means any identifiable chemical or molecule, including, but not limited to, small molecule, peptide, protein, sugar, nucleotide, or nucleic acid, and such compound can be natural or synthetic.

As used herein, the term "complementary" refers to Watson-Crick basepairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains the nucleic acid molecule, or polypeptide encoding the MMP or fragment thereof.

As used herein, the phrase "homologous nucleotide sequence," or "homologous amino acid sequence," or variations thereof, refers to sequences characterized by a homology, at the nucleotide level or amino acid level, of at least the specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding other known MMPs. Homologous amino acid sequences include those amino acid sequences which contain conservative amino acid substitutions and which polypeptides have the same binding and/or activity. A homologous amino acid sequence does not, however, include the amino acid sequence encoding other known MMPs. Percent homology can be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Adv. Appl. Math., 1981, 2, 482–489, which is incorporated herein by reference in its entirety).

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "modulates" or "modifies" means an increase or decrease in the amount, quality, or effect of a particular activity or protein.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

The term "preventing" refers to decreasing the probability that an organism contracts or develops an abnormal condition.

The term "treating" refers to having a therapeutic effect and at least partially alleviating or abrogating an abnormal condition in the organism.

The term "therapeutic effect" refers to the inhibition or activation factors causing or contributing to the abnormal condition. A therapeutic effect relieves to some extent one or more of the symptoms of the abnormal condition. In reference to the treatment of abnormal conditions, a therapeutic effect can refer to one or more of the following: (a) an increase in the proliferation, growth, and/or differentiation of cells; (b) inhibition (i.e., slowing or stopping) of cell death; (c) inhibition of degeneration; (d) relieving to some extent one or more of the symptoms associated with the abnormal condition; and (e) enhancing the function of the affected population of cells. Compounds demonstrating efficacy against abnormal conditions can be identified as described herein.

The term "abnormal condition" refers to a function in the cells or tissues of an organism that deviates from their normal functions in that organism. An abnormal condition can relate to cell proliferation, cell differentiation, cell signaling, or cell survival. An abnormal condition may also include obesity, diabetic complications such as retinal degeneration, and irregularities in glucose uptake and metabolism, and fatty acid uptake and metabolism.

Abnormal cell proliferative conditions include cancers such as fibrotic and mesangial disorders, abnormal angiogenesis and vasculogenesis, wound healing, psoriasis, diabetes mellitus, and inflammation.

Abnormal differentiation conditions include, but are not limited to, neurodegenerative disorders, slow wound healing rates, and slow tissue grafting healing rates. Abnormal cell signaling conditions include, but are not limited to, psychiatric disorders involving excess neurotransmitter activity.

Abnormal cell survival conditions may also relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

The term "aberration," in conjunction with the function of an MMP, refers to an MMP that is over- or under-expressed in an organism, mutated such that its catalytic activity is lower or higher than wild-type protease activity, mutated such that it can no longer interact with a natural binding partner, or is no longer modified by another protease.

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques and carrier techniques.

The abnormal condition can also be prevented or treated by administering a compound to a group of cells having an aberration in a signal transduction pathway to an organism. The effect of administering a compound on organism function can then be monitored. The organism is preferably a mouse, rat, rabbit, guinea pig or goat, more preferably a monkey or ape, and most preferably a human.

By "amplification" it is meant increased numbers of DNA or RNA in a cell compared with normal cells. "Amplification" as it refers to RNA can be the detectable presence of RNA in cells, since in some normal cells there is no basal expression of RNA. In other normal cells, a basal level of expression exists, therefore in these cases amplification is the detection of at least 1 to 2-fold, and preferably more, compared to the basal level.

As used herein, the phrase "stringent hybridization conditions" or "stringent conditions" refers to conditions under which a probe, primer, or oligonucleotide will hybridize to its target sequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at $T_m$, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

The amino acid sequences are presented in the amino to carboxy direction, from left to right. The amino and carboxy groups are not presented in the sequence. The nucleotide sequences are presented by single strand only, in the 5' to 3' direction, from left to right. Nucleotides and amino acids are represented in the manner recommended by the IUPAC-IUB Biochemical Nomenclature Commission or (for amino acids) by three letters code.

Polynucleotides

The present invention provides purified and isolated polynucleotides (e.g., DNA sequences and RNA transcripts, both sense and complementary antisense strands, both single- and double-stranded, including splice variants thereof) that encode unknown MMPs heretofore termed novel MMPs, or MMPs.

It is well known that MMPs are expressed in many different tissues, including the brain. Accordingly, the MMPs of the present invention may be useful, inter alia, for treating and/or diagnosing mental disorders. Following the techniques described in Example 4, below, those skilled in the art could readily ascertain if MMP is expressed in a particular tissue or region.

The invention provides purified and isolated polynucleotides (e.g., cDNA, genomic DNA, synthetic DNA, RNA, or combinations thereof, whether single- or double-stranded) that comprise a nucleotide sequence encoding the amino acid sequence of the polypeptides of the invention. Such polynucleotides are useful for recombinantly expressing the MMP and also for detecting expression of the MMP in cells (e.g., using Northern hybridization and in situ hybridization assays). Such polynucleotides also are useful in the design of antisense and other molecules for the suppression of the expression of MMP in a cultured cell, a tissue, or an animal; for therapeutic purposes; or to provide a model for diseases or conditions characterized by aberrant MMP expression. Specifically excluded from the definition of polynucleotides of the invention are entire isolated, non-recombinant native chromosomes of host cells. A preferred polynucleotide has a sequence selected from the group consisting of SEQ ID NO:1 to SEQ ID NO:3, which correspond to naturally occurring MMP sequences. It will be appreciated that numerous other polynucleotide sequences exist that also encode MMP having the sequence selected from the group consisting of SEQ ID NO:4 to SEQ ID NO:6, due to the well-known degeneracy of the universal genetic code.

The invention also provides a purified and isolated polynucleotide comprising a nucleotide sequence that encodes a mammalian polypeptide, wherein the polynucleotide hybridizes to a polynucleotide having the sequence set forth in sequences selected from the group consisting of SEQ ID NO:1 to SEQ ID NO:3, or the non-coding strand complementary thereto, under the following hybridization conditions:
  (a) hybridization for 16 hours at 42° C. in a hybridization solution comprising 50% formamide, 1% SDS, 1 M NaCl, 10% dextran sulfate; and
  (b) washing 2 times for 30 minutes each at 60° C. in a wash solution comprising 0.1% SSC, 1% SDS. Polynucleotides that encode a human allelic variant are highly preferred.

The present invention relates to molecules which comprise the gene sequences that encode the MMPs; constructs and recombinant host cells incorporating the gene sequences; the novel MMP polypeptides encoded by the gene sequences; antibodies to the polypeptides and homologs; kits employing the polynucleotides and polypeptides, and methods of making and using all of the foregoing. In addition, the present invention relates to homologs of the gene sequences and of the polypeptides and methods of making and using the same.

Genomic DNA of the invention comprises the protein-coding region for a polypeptide of the invention and is also intended to include allelic variants thereof. It is widely understood that, for many genes, genomic DNA is transcribed into RNA transcripts that undergo one or more splicing events wherein intron (i.e., non-coding regions) of the transcripts are removed, or "spliced out." RNA transcripts that can be spliced by alternative mechanisms, and therefore be subject to removal of different RNA sequences but still encode an MMP polypeptide, are referred to in the art as splice variants which are embraced by the invention. Splice variants comprehended by the invention therefore are encoded by the same original genomic DNA sequences but arise from distinct mRNA transcripts. Allelic variants are modified forms of a wild-type gene sequence, the modification resulting from recombination during chromosomal segregation or exposure to conditions which give rise to genetic mutation. Allelic variants, like wild type genes, are naturally occurring sequences (as opposed to non-naturally occurring variants that arise from in vitro manipulation).

The invention also comprehends cDNA that is obtained through reverse transcription of an RNA polynucleotide encoding MMP (conventionally followed by second strand synthesis of a complementary strand to provide a double-stranded DNA).

Preferred DNA sequences encoding human MMP polypeptides are selected from the group consisting of SEQ ID NO:1 to SEQ ID NO:3. A preferred DNA of the invention comprises a double stranded molecule along with the complementary molecule (the "non-coding strand" or "complement") having a sequence unambiguously deducible from the coding strand according to Watson-Crick base-pairing rules for DNA. Also preferred are other polynucleotides encoding the MMP polypeptide selected from the group consisting of SEQ ID NO:4 to SEQ ID NO:6, which differ in sequence from the polynucleotides selected from the group consisting of SEQ ID NO:1 to SEQ ID NO:3, by virtue of the well-known degeneracy of the universal nuclear genetic code.

The invention further embraces other species, preferably mammalian, homologs of the human MMP DNA. Species homologs, sometimes referred to as "orthologs," in general, share at least 35%, at least 40%, at least 45%, at least 50%, at least 60%, at least 65%, at least 70%, at least 75%, at least 80%, at least 85%, at least 90%, at least 95%, at least 98%, or at least 99% homology with human DNA of the invention. Generally, percent sequence "homology" with respect to polynucleotides of the invention may be calculated as the percentage of nucleotide bases in the candidate sequence that are identical to nucleotides in the MMP sequences set forth in sequences selected from the group consisting of SEQ ID NO:1 to SEQ ID NO:3, after aligning the sequences and introducing gaps, if necessary, to achieve the maximum percent sequence identity.

Polynucleotides of the invention permit identification and isolation of polynucleotides encoding related MMP polypeptides, such as human allelic variants and species homologs, by well-known techniques including Southern and/or Northern hybridization, and polymerase chain reaction (PCR). Examples of related polynucleotides include human and non-human genomic sequences, including allelic variants, as well as polynucleotides encoding polypeptides homologous to MMP and structurally related polypeptides sharing one or more biological, immunological, and/or physical properties of MMP. Non-human species genes encoding proteins homologous to MMP can also be identified by Southern and/or PCR analysis and are useful in animal models for MMP disorders. Knowledge of the sequence of a human MMP DNA also makes possible through use of Southern hybridization or polymerase chain reaction (PCR) the identification of genomic DNA sequences encoding MMP expression control regulatory sequences such as promoters, operators, enhancers, repressors, and the like. Polynucleotides of the invention are also useful in hybridization assays to detect the capacity of cells to express MMP. Polynucleotides of the invention may also provide a basis for diagnostic methods useful for identifying a genetic alteration(s) in an MMP locus that underlies a disease state or states, which information is useful both for diagnosis and for selection of therapeutic strategies.

According to the present invention, the MMP nucleotide sequences disclosed herein may be used to identify homologs of the MMP, in other animals, including but not limited to humans and other mammals, and invertebrates. Any of the nucleotide sequences disclosed herein, or any portion thereof, can be used, for example, as probes to screen databases or nucleic acid libraries, such as, for example, genomic or cDNA libraries, to identify homologs, using screening procedures well known to those skilled in the art. Accordingly, homologs having at least 50%, more preferably at least 60%, more preferably at least 70%, more preferably at least 80%, more preferably at least 90%, more preferably at least 95%, and most preferably at least 100% homology with MMP sequences can be identified.

The disclosure herein of full-length polynucleotides encoding MMP polypeptides makes readily available to the worker of ordinary skill in the art every possible fragment of the full-length polynucleotide.

In a preferred embodiment, the isolated nucleic acid comprises a nucleotide sequence of SEQ ID NO: 2, and fragments thereof, that encode a polypeptide having a sequence of SEQ ID NO: 5, or fragments thereof. In a more preferred embodiment, the nucleotide is not SEQ ID NO:7 and does not encode a polypeptide with a sequence of SEQ ID NO:8.

As used in the present invention, fragments of MMP-encoding polynucleotides comprise at least 10, and preferably at least 12, 14, 16, 18, 20, 25, 50, or 75 consecutive nucleotides of a polynucleotide encoding MMP. Preferably, fragment polynucleotides of the invention comprise sequences unique to the MMP-encoding polynucleotide sequence, and therefore hybridize under highly stringent or moderately stringent conditions only (i.e., "specifically") to polynucleotides encoding MMP (or fragments thereof). Polynucleotide fragments of genomic sequences of the invention comprise not only sequences unique to the coding region, but also include fragments of the full-length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases. Such sequences also are recognizable from Southern hybridization-analyses to determine the number of fragments of genomic DNA to which a polynucleotide will hybridize. Polynucleotides of the invention can be labeled in a manner that permits their detection, including radioactive, fluorescent, and enzymatic labeling.

Fragment polynucleotides are particularly useful as probes for detection of full-length or fragments of MMP polynucleotides. One or more polynucleotides can be included in kits that are used to detect the presence of a polynucleotide encoding MMP, or used to detect variations in a polynucleotide sequence encoding MMP.

The invention also embraces DNAs encoding MMP polypeptides that hybridize under moderately stringent or high stringency conditions to the non-coding strand, or complement, of the polynucleotides set forth in sequences selected from the group consisting of SEQ ID NO:1 to SEQ ID NO:3.

Exemplary highly stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS. It is understood in the art that conditions of equivalent stringency can be achieved through variation of temperature and buffer, or salt concentration as described Ausubel et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

With the knowledge of the nucleotide sequence information disclosed in the present invention, one skilled in the art can identify and obtain nucleotide sequences which encode MMP from different sources (i.e., different tissues or different organisms) through a variety of means well known to the skilled artisan and as disclosed by, for example, Sambrook et al., "Molecular cloning: a laboratory manual", Second Edition, Cold Spring Harbor Press, Cold Spring Harbor, N.Y. (1989), which is incorporated herein by reference in its entirety.

For example, DNA that encodes MMP may be obtained by screening of mRNA, cDNA, or genomic DNA with oligonucleotide probes generated from the MMP gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising any of the MMP nucleotide sequences described above can alternatively be synthesized by use of the polymerase chain reaction (PCR) procedure, with the PCR oligonucleotide primers produced from the nucleotide sequences provided herein. See U.S. Pat. No. 4,683,195 to Mullis et al. and U.S. Pat. No. 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, Methods in Enzymology 152, Academic Press, Inc., San Diego, Calif. (Berger), which is incorporated herein by reference in its entirety.

Automated sequencing methods can be used to obtain or verify the nucleotide sequence of MMP. The MMP nucleotide sequences of the present invention are believed to be 100% accurate. However, as is known in the art, nucleotide sequence obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in a sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

The nucleic acid molecules of the present invention, and fragments derived therefrom, are useful for screening for restriction fragment length polymorphism (RFLP) associated with certain disorders, as well as for genetic mapping.

The polynucleotide sequence information provided by the invention makes possible large-scale expression of the encoded polypeptide by techniques well known and routinely practiced in the art.

Vectors

Another aspect of the present invention is directed to vectors, or recombinant expression vectors, comprising any of the nucleic acid molecules described above. Vectors are used herein either to amplify DNA or RNA encoding MMP and/or to express DNA which encodes MMP. Preferred vectors include, but are not limited to, plasmids, phages, cosmids, episomes, viral particles or viruses, and integratable DNA fragments (i.e., fragments integratable into the host genome by homologous recombination). Preferred viral particles include, but are not limited to, adenoviruses, baculoviruses, parvoviruses, herpesviruses, poxviruses, adeno-associated viruses, Semliki Forest viruses, vaccinia viruses, and retroviruses. Preferred expression vectors include, but are not limited to, pcDNA3 (Invitrogen) and pSVL (Pharmacia Biotech). Other expression vectors include, but are not limited to, pSPORT™ vectors, pGEM™ vectors (Promega), pPROEXvectors™ (LTI, Bethesda, Md.), Bluescript™ vectors (Stratagene), pQE™ vectors (Qiagen), pSE420™ (Invitrogen), and pYES2™(Invitrogen).

Expression constructs preferably comprise MMP-encoding polynucleotides operatively linked to an endogenous or exogenous expression control DNA sequence and a transcription terminator. Expression control DNA sequences include promoters, enhancers, operators, and regulatory element binding sites generally, and are typically selected based on the expression systems in which the expression construct is to be utilized. Preferred promoter and enhancer sequences are generally selected for the ability to increase gene expression, while operator sequences are generally selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell.

Expression constructs are preferably utilized for production of an encoded protein, but may also be utilized simply to amplify an MMP-encoding polynucleotide sequence. In preferred embodiments, the vector is an expression vector wherein the polynucleotide of the invention is operatively linked to a polynucleotide comprising an expression control sequence. Autonomously replicating recombinant expression constructs such as plasmid and viral DNA vectors incorporating polynucleotides of the invention are also provided. Preferred expression vectors are replicable DNA constructs in which a DNA sequence encoding MMP is operably linked or connected to suitable control sequences capable of effecting the expression of the MMP in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include a transcriptional promoter, an optional operator sequence to control transcription, a sequence encoding suitable mRNA ribosomal binding and sequences which control the termination of transcription and translation.

Preferred vectors preferably contain a promoter that is recognized by the host organism. The promoter sequences of the present invention may be prokaryotic, eukaryotic or viral. Examples of suitable prokaryotic sequences include the $P_R$ and $P_L$ promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacZ promoters of *E. coli* and the SV40 early promoter (Benoist et al. *Nature*, 1981, 290, 304–310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, Rous sarcoma virus, human actin, human myosin, human hemoglobin, human muscle creatine, and human metalothionein.

Additional regulatory sequences can also be included in preferred vectors. Preferred examples of suitable regulatory sequences are represented by the Shine-Dalgarno of the replicase gene of the phage MS-2 and of the gene cII of bacteriophage lambda. The Shine-Dalgarno sequence may be directly followed by DNA encoding MMP and result in the expression of the mature MMP protein.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and MMP DNA. An example of a suitable marker is dihydrofolate reductase (DHFR) or thymidine kinase (see, U.S. Pat. No. 4,399,216).

Nucleotide sequences encoding MMP may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.*, 1983, 3, 280, Cosman et al., *Mol. Immunol.*, 1986, 23, 935, Cosman et al., *Nature*, 1984, 312, 768, EP-A-0367566, and WO 91/18982, each of which is incorporated herein by reference in its entirety.

Host cells

According to another aspect of the invention, host cells are provided, including prokaryotic and eukaryotic cells, comprising a polynucleotide of the invention (or vector of the invention) in a manner that permits expression of the encoded MMP polypeptide. Polynucleotides of the invention may be introduced into the host cell as part of a circular plasmid, or as linear DNA comprising an isolated protein coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cells systems.

The invention provides host cells that are transformed or transfected (stably or transiently) with polynucleotides of the invention or vectors of the invention. As stated above, such host cells are useful for amplifying the polynucleotides and also for expressing the MMP polypeptide or fragment thereof encoded by the polynucleotide.

In still another related embodiment, the invention provides a method for producing a MMP polypeptide (or fragment thereof) comprising the steps of growing a host cell of the invention in a nutrient medium and isolating the polypeptide or variant thereof from the cell or the medium.

According to some aspects of the present invention, transformed host cells having an expression vector comprising any of the nucleic acid molecules described above are provided. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces*, and *Staphylococcus*.

If an eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human HEK-293 cells, and murine 3T3 fibroblasts. Propagation of such cells in cell culture has become a routine procedure (see, Tissue Culture, Academic Press, Kruse and Patterson, eds. (1973), which is incorporated herein by reference in its entirety).

In addition, a yeast host may be employed as a host cell. Preferred yeast cells include, but are not limited to, the genera *Saccharomyces, Pichia*, and *Kluveromyces*. Preferred yeast hosts are *S. cerevisiae* and *P. pastoris*. Preferred yeast vectors can contain an origin of replication sequence from a 2T yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology*, 1988, 6, 47, Baculovirus Expression Vectors: A Laboratory Manual, O'Rielly et al. (Eds.), W. H. Freeman and Company, New York, 1992, and U.S. Pat. No. 4,879,236, each of which is incorporated herein by reference in its entirety). In addition, the MAX-BAC™ complete baculovirus expression system (Invitrogen) can, for example, be used for production in insect cells.

Host cells of the invention are a valuable source of immunogen for development of antibodies specifically immunoreactive with MMP. Host cells of the invention are also useful in methods for the large-scale production of MMP polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Knowledge of MMP DNA sequences allows for modification of cells to permit, or increase, expression of endogenous MMP. Cells can be modified (e.g., by homologous recombination) to provide increased expression by replacing, in whole or in part, the naturally occurring MMP promoter with all or part of a heterologous promoter so that the cells express MMP at higher levels. The heterologous promoter is inserted in such a manner that it is operatively linked to endogenous MMP encoding sequences. (See, for example, PCT International Publication No. WO 94/12650, PCT International Publication No. WO 92/20808, and PCT International Publication No. WO 91/09955.) It is also contemplated that, in addition to heterologous promoter DNA, amplifiable marker DNA (e.g., ada, dhfr, and the multifunctional CAD gene which encodes carbamoyl phosphate synthase, aspartate transcarbamylase, and dihydroorotase) and/or intron DNA may be inserted along with the heterologous promoter DNA. If linked to the MMP coding sequence, amplification of the marker DNA by standard selection methods results in co-amplification of the MMP coding sequences in the cells.

Knock-outs

The DNA sequence information provided by the present invention also makes possible the development (e.g., by homologous recombination or "knock-out" strategies; see Capecchi, *Science* 244:1288–1292 (1989), which is incorporated herein by reference) of animals that fail to express functional MMP or that express a variant of MMP. Such animals (especially small laboratory animals such as rats, rabbits, and mice) are useful as models for studying the in vivo activities of MMP and modulators of MMP.

Antisense

Also made available by the invention are anti-sense polynucleotides that recognize and hybridize to polynucleotides encoding MMP. Full-length and fragment anti-sense polynucleotides are provided. Fragment antisense molecules of the invention include (i) those that specifically recognize and hybridize to MMP RNA (as determined by sequence comparison of DNA encoding MMP to DNA encoding other known molecules). Identification of sequences unique to MMP encoding polynucleotides can be deduced through use of any publicly available sequence database, and/or through use of commercially available sequence comparison programs. After identification of the desired sequences, isolation through restriction digestion or amplification using any of the various polymerase chain reaction techniques well known in the art can be performed. Anti-sense polynucleotides are particularly relevant to regulating expression of MMP by those cells expressing MMP mRNA.

Antisense nucleic acids (preferably 10 to 30 base-pair oligonucleotides) capable of specifically binding to MMP expression control sequences or MMP RNA are introduced into cells (e.g., by a viral vector or colloidal dispersion system such as a liposome). The antisense nucleic acid binds to the MMP target nucleotide sequence in the cell and prevents transcription and/or translation of the target sequence. Phosphorothioate and methylphosphonate antisense oligonucleotides are specifically contemplated for therapeutic use by the invention. The antisense oligonucleotides may be further modified by adding poly-L-lysine, transferrin polylysine, or cholesterol moieties at their 5' end. Suppression of MMP expression at either the transcriptional or translational level is useful to generate cellular or animal models for diseases/conditions characterized by aberrant MMP expression.

Antisense oligonucleotides, or fragments of sequences selected from the group consisting of SEQ ID NO:1 to SEQ ID NO:3, or sequences complementary or homologous thereto, derived from the nucleotide sequences of the present invention encoding MMP are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides are preferably directed to regulatory regions of sequences selected from the group consisting of SEQ ID NO:1 to SEQ ID NO:3, or mRNA corresponding thereto, including, but not limited to, the initiation codon, TATA box, enhancer sequences, and the like.

Transcription Factors

The MMP sequences taught in the present invention facilitate the design of novel transcription factors for modulating MMP expression in native cells and animals, and cells transformed or transfected with MMP polynucleotides. For example, the $Cys_2$-$His_2$ zinc finger proteins, which bind DNA via their zinc finger domains, have been shown to be amenable to structural changes that lead to the recognition of different target sequences. These artificial zinc finger proteins recognize specific target sites with high affinity and low dissociation constants, and are able to act as gene switches to modulate gene expression. Knowledge of the particular MMP target sequence of the present invention facilitates the engineering of zinc finger proteins specific for the target sequence using known methods such as a combination of structure-based modeling and screening of phage display libraries (Segal et al., Proc. Natl. Acad. Sci. (USA) 96:2758–2763 (1999); Liu et al., Proc. Natl. Acad. Sci. (USA) 94:5525–5530 (1997); Greisman et al., Science 275: 657–661 (1997); Choo et al., J. Mol. Biol. 273:525–532 (1997)). Each zinc finger domain usually recognizes three or more base pairs. Since a recognition sequence of 18 base pairs is generally sufficient in length to render it unique in any known genome, a zinc finger protein consisting of 6 tandem repeats of zinc fingers would be expected to ensure specificity for a particular sequence (Segal et al.) The artificial zinc finger repeats, designed based on MMP sequences, are fused to activation or repression domains to promote or suppress MMP expression (Liu et al.) Alternatively, the zinc finger domains can be fused to the TATA box-binding factor (TBP) with varying lengths of linker region between the zinc finger peptide and the TBP to create either transcriptional activators or repressors (Kim et al., Proc. Natl. Acad. Sci. (USA) 94:3616–3620 (1997). Such proteins and polynucleotides that encode them, have utility for modulating MMP expression in vivo in both native cells, animals and humans; and/or cells transfected with MMP-encoding sequences. The novel transcription factor can be delivered to the target cells by transfecting constructs that express the transcription factor (gene therapy), or by introducing the protein. Engineered zinc finger proteins can also be designed to bind RNA sequences for use in therapeutics as alternatives to antisense or catalytic RNA methods (McColl et al., Proc. Natl. Acad. Sci. (USA) 96:9521–9526 (1997); Wu et al., Proc. Natl. Acad. Sci. (USA) 92:344–348 (1995)). The present invention contemplates methods of designing such transcription factors based on the gene sequence of the invention, as well as customized zinc finger proteins, that are useful to modulate MMP expression in cells (native or transformed) whose genetic complement includes these sequences.

Polypeptides

The invention also provides purified and isolated mammalian MMP polypeptides encoded by a polynucleotide of the invention. Presently preferred is a human MMP polypeptide comprising the amino acid sequence set out in sequences selected from the group consisting of SEQ ID NO:4 to SEQ ID NO:6, or fragments thereof comprising an epitope specific to the polypeptide. By "epitope specific to" is meant a portion of the MMP that is recognizable by an antibody that is specific for the MMP, as defined in detail below.

Although the sequences provided are particular human sequences, the invention is intended to include within its scope other human allelic variants; non-human mammalian forms of MMP, and other vertebrate forms of MMP.

The invention also embraces polypeptides that have at least 99%, at least 95%, at least 90%, at least 85%, at least 80%, at least 75%, at least 70%, at least 65%, at least 60%, at least 55% or at least 50% identity and/or homology to the preferred polypeptide of the invention. Percent amino acid sequence "identity" with respect to the preferred polypeptide of the invention is defined herein as the percentage of amino acid residues in the candidate sequence that are identical with the residues in the MMP sequence after aligning both sequences and introducing gaps, if necessary, to achieve the maximum percent sequence identity, and not considering any conservative substitutions as part of the sequence identity. Percent sequence "homology" with respect to the preferred polypeptide of the invention is defined herein as the percentage of amino acid residues in the candidate sequence that are identical with the residues in the MMP sequence after aligning the sequences and introducing gaps, if necessary, to achieve the maximum percent sequence identity, and also considering any conservative substitutions as part of the sequence identity.

In one aspect, percent homology is calculated as the percentage of amino acid residues in the smaller of two sequences which align with identical amino acid residue in the sequence being compared, when four gaps in a length of 100 amino acids may be introduced to maximize alignment (Dayhoff, in *Atlas of Protein Sequence and Structure*, Vol. 5, p. 124, National Biochemical Research Foundation, Washington, D.C. (1972), incorporated herein by reference).

Polypeptides of the invention may be isolated from natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms of MMP polypeptides are embraced by the invention.

The invention also embraces variant (or analog) MMP polypeptides. In one example, insertion variants are provided wherein one or more amino acid residues supplement a MMP amino acid sequence. Insertions may be located at either or both termini of the protein, or may be positioned within internal regions of the MMP amino acid sequence. Insertional variants with additional residues at either or both termini can include, for example, fusion proteins and proteins including amino acid tags or labels.

Insertion variants include MMP polypeptides wherein one or more amino acid residues are added to a MMP acid sequence or to a biologically active fragment thereof.

Variant products of the invention also include mature MMP products, i.e., MMP products wherein leader or signal sequences are removed, with additional amino terminal residues. The additional amino terminal residues may be derived from another protein, or may include one or more residues that are not identifiable as being derived from specific proteins. MMP products with an additional methionine residue at position −1 (Met$^{-1}$-MMP) are contemplated, as are variants with additional methionine and lysine residues at positions −2 and −1 (Met$^{-2}$-Lys$^{-1}$-MMP). Variants of MMP with additional Met, Met-Lys, Lys residues (or one or more basic residues in general) are particularly useful for enhanced recombinant protein production in bacterial host cells.

The invention also embraces MMP variants having additional amino acid residues that result from use of specific expression systems. For example, use of commercially available vectors that express a desired polypeptide as part of a glutathione-S-transferase (GST) fusion product provides the desired polypeptide having an additional glycine residue at position −1 after cleavage of the GST component from the desired polypeptide. Variants that result from expression in other vector systems are also contemplated.

Insertional variants also include fusion proteins wherein the amino terminus and/or the carboxy terminus of MMP is/are fused to another polypeptide.

In another aspect, the invention provides deletion variants wherein one or more amino acid residues in a MMP polypeptide are removed. Deletions can be effected at one or both termini of the MMP polypeptide, or with removal of one or more non-terminal amino acid residues of MMP. Deletion variants, therefore, include all fragments of a MMP polypeptide.

The invention also embraces polypeptide fragments of sequences selected from the group consisting of SEQ ID NO:4 to SEQ ID NO:6, wherein the fragments maintain biological (e.g., proteinase or collagenase activity) and immunological properties of a MMP polypeptide.

In one preferred embodiment of the invention, an isolated nucleic acid molecule comprises a nucleotide sequence that encodes a polypeptide comprising an amino acid sequence homologous to sequences selected from the group consisting of SEQ ID NO:4 to SEQ ID NO:6, and fragments thereof, wherein the nucleic acid molecule encoding at least a portion of MMP. In a more preferred embodiment, the isolated nucleic acid molecule comprises a sequence that encodes a polypeptide comprising sequences selected from the group consisting of SEQ ID NO:4 to SEQ ID NO:6, and fragments thereof.

One preferred embodiment of the present invention provides an isolated nucleic acid molecule comprising a sequence homologous sequences selected from the group consisting of SEQ ID NO:1 to SEQ ID NO:3, and fragments thereof. Another preferred embodiment provides an isolated nucleic acid molecule comprising a sequence selected from the group consisting of SEQ ID NO:1 to SEQ ID NO:3, and fragments thereof.

In a preferred embodiment, the isolated nucleic acid molecule comprises a nucleotide sequence which encodes a polypeptide comprising a sequence of SEQ ID NO:5, or a fragment thereof. In a more preferred embodiment, the polypeptide encoded by the nucleotide sequence does not have the sequence of SEQ ID NO:8.

As used in the present invention, polypeptide fragments comprise at least 5, 10, 15, 20, 25, 30, 35, or 40 consecutive amino acids of sequences selected from the group consisting of SEQ ID NO:4 to SEQ ID NO:6. Preferred polypeptide fragments display antigenic properties unique to, or specific for, human MMP and its allelic and species homologs. Fragments of the invention having the desired biological and immunological properties can be prepared by any of the methods well known and routinely practiced in the art.

In still another aspect, the invention provides substitution variants of MMP polypeptides. Substitution variants include those polypeptides wherein one or more amino acid residues of a MMP polypeptide are removed and replaced with alternative residues. In one aspect, the substitutions are conservative in nature; however, the invention embraces substitutions that are also non-conservative. Conservative substitutions for this purpose may be defined as set out in Tables 2, 3, or 4 below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 2 (from WO 97/09433, page 10, published Mar. 13, 1997 (PCT/GB96/02197, filed Sep. 6, 1996), immediately below.

TABLE 2

| Conservative Substitutions I | |
|---|---|
| SIDE CHAIN CHARACTERISTIC | AMINO ACID |
| Aliphatic | |
| Non-polar | G A P |
| I L V | |
| Polar - uncharged | C S T M |
| N Q | |
| Polar - charged | D E |
| K R | |
| Aromatic | H F W Y |
| Other | N Q D E |

Alternatively, conservative amino acids can be grouped as described in Lehninger, [*Biochemistry*, Second Edition; Worth Publishers, Inc. New York, N.Y. (1975), pp.71–77] as set out in Table 3, below.

TABLE 3

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 4, below.

TABLE 4

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of polypeptides of the invention is intended to include polypeptides bearing modifications other than insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide, or may be designed to improve the targeting capacity of the polypeptide for desired cells, tissues, or organs. Similarly, the invention further embraces MMP polypeptides that have been covalently modified to include one or more water-soluble polymer attachments such as polyethylene glycol, polyoxyethylene glycol, or polypropylene glycol. Variants that display ligand binding properties of native MMP and are expressed at higher levels are particularly useful in assays of the invention; the variants are also useful in providing cellular, tissue and animal models of diseases/conditions characterized by aberrant MMP activity.

In a related embodiment, the present invention provides compositions comprising purified polypeptides of the invention. Preferred compositions comprise, in addition to the polypeptide of the invention, a pharmaceutically acceptable (i.e., sterile and non-toxic) liquid, semisolid, or solid diluent that serves as a pharmaceutical vehicle, excipient, or medium. Any diluent known in the art may be used. Exemplary diluents include, but are not limited to, water, saline solutions, polyoxyethylene sorbitan monolaurate, magnesium stearate, methyl- and propylhydroxybenzoate, talc, alginates, starches, lactose, sucrose, dextrose, sorbitol, mannitol, glycerol, calcium phosphate, mineral oil, and cocoa butter.

Antibodies

Also comprehended by the present invention are antibodies (e.g., monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR sequences which specifically recognize a polypeptide of the invention) specific for MMP or fragments thereof. Preferred antibodies of the invention are human antibodies that are produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for," when used to describe antibodies of the invention, indicates that the variable regions of the antibodies of the invention recognize and bind MMP polypeptides exclusively (i.e., are able to distinguish MMP polypeptides from other known MMP polypeptides by virtue of measurable differences in binding affinity, despite the possible existence of localized sequence identity, homology, or similarity between MMP and such polypeptides). It will be understood that specific antibodies may also interact with other proteins (for example, *S. aureus* protein A or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), *Antibodies A Laboratory Manual*; Cold Spring Harbor Laboratory; Cold Spring Harbor, N.Y. (1988), Chapter 6. Antibodies that recognize and bind fragments of the MMP polypeptides of the invention are also contemplated, provided that the antibodies are specific for MMP polypeptides. Antibodies of the invention can be produced using any method well known and routinely practiced in the art.

The invention provides an antibody that is specific for the MMP of the invention. Antibody specificity is described in greater detail below. However, it should be emphasized that antibodies that can be generated from polypeptides that have previously been described in the literature and that are capable of fortuitously cross-reacting with MMP (e.g., due to the fortuitous existence of a similar epitope in both polypeptides) are considered "cross-reactive" antibodies. Such cross-reactive antibodies are not antibodies that are "specific" for MMP. The determination of whether an antibody is specific for MMP or is cross-reactive with another known MMP is made using any of several assays, such as Western blotting assays, that are well known in the art.

In one preferred variation, the invention provides monoclonal antibodies. Hybridomas that produce such antibodies also are intended as aspects of the invention. In yet another variation, the invention provides a humanized antibody. Humanized antibodies are useful for in vivo therapeutic indications.

In another variation, the invention provides a cell-free composition comprising polyclonal antibodies, wherein at least one of the antibodies is an antibody of the invention specific for MMP. Antisera isolated from an animal is an exemplary composition, as is a composition comprising an antibody fraction of an antisera that has been resuspended in water or in another diluent, excipient, or carrier.

In still another related embodiment, the invention provides an anti-idiotypic antibody specific for an antibody that is specific for MMP.

It is well known that antibodies contain relatively small antigen binding domains that can be isolated chemically or by recombinant techniques. Such domains are useful MMP binding molecules themselves, and also may be reintroduced into human antibodies, or fused to toxins or other polypeptides. Thus, in still another embodiment, the invention provides a polypeptide comprising a fragment of an MMP-specific antibody, wherein the fragment and the polypeptide bind to the MMP. By way of non-limiting example, the invention provides polypeptides that are single chain antibodies and CDR-grafted antibodies.

Non-human antibodies may be humanized by any of the methods known in the art. In one method, the non-human CDRs are inserted into a human antibody or consensus antibody framework sequence. Further changes can then be introduced into the antibody framework to modulate affinity or immunogenicity.

Antibodies of the invention are useful for, e.g., therapeutic purposes (by modulating activity of MMP), diagnostic purposes to detect or quantitate MMP, and purification of MMP. Kits comprising an antibody of the invention for any of the purposes described herein are also comprehended. In general, a kit of the invention also includes a control antigen for which the antibody is immunospecific.

Compositions

Mutations in the MMP gene that result in loss of normal function of the MMP gene product underlie MMP-related human disease states. The invention comprehends gene therapy to restore MMP activity to treat those disease states. Delivery of a functional MMP gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, *Nature*, supplement to vol. 392, no. 6679, pp.25–20 (1998). For additional reviews of gene therapy technology see Friedmann, *Science*, 244: 1275–1281 (1989); Verma, *Scientific American*: 68–84 (1990); and Miller, *Nature*, 357: 455–460 (1992). Alternatively, it is contemplated that in other human disease states, preventing the expression of, or inhibiting the activity of, MMP will be useful in treating disease states. It is contemplated that antisense therapy or gene therapy could be applied to negatively regulate the expression of MMP.

Another aspect of the present invention is directed to compositions, including pharmaceutical compositions, comprising any of the nucleic acid molecules or recombinant expression vectors described above and an acceptable carrier or diluent. Preferably, the carrier or diluent is pharmaceutically acceptable. Suitable carriers are described in the most recent edition of *Remington's Pharmaceutical Sciences*, A. Osol, a standard reference text in this field, which is incorporated herein by reference in its entirety. Preferred examples of such carriers or diluents include, but are not limited to, water, saline, Ringer's solution, dextrose solution, and 5% human serum albumin. Liposomes and non-aqueous vehicles such as fixed oils may also be used. The formulations are sterilized by commonly used techniques.

Also within the scope of the invention are compositions comprising polypeptides, polynucleotides, or antibodies of the invention that have been formulated with, e.g., a pharmaceutically acceptable carrier.

The invention also provides methods of using antibodies of the invention. For example, the invention provides a method for modulating ligand binding of a MMP comprising the step of contacting the MMP with an antibody specific for the MMP, under conditions wherein the antibody binds the MMP.

As discussed above, it is well known that MMPs are expressed in many different tissues and regions, including in the brain. MMPs that may be expressed in the brain provide an indication that aberrant MMP activity may correlate with one or more neurological or psychological disorders. The invention also provides a method for treating a neurological or psychiatric disorder comprising the step of administering to a mammal in need of such treatment an amount of an antibody-like polypeptide of the invention that is sufficient to modulate ligand binding to a MMP in neurons of the mammal. MMP may also be expressed in other tissues, including but not limited to, including but not limited to pancreas (and particularly pancreatic islet tissue), pituitary, skeletal muscle, adipose tissue, liver, and thyroid, and may be found in many other tissues.

Kits

The present invention is also directed to kits, including pharmaceutical kits. The kits can comprise any of the nucleic acid molecules described above, any of the polypeptides described above, or any antibody which binds to a polypeptide of the invention as described above, as well as a negative control. The kit preferably comprises additional components, such as, for example, instructions, solid support, reagents helpful for quantification, and the like.

In another aspect, the invention features methods for detection of a polypeptide in a sample as a diagnostic tool for diseases or disorders, wherein the method comprises the steps of: (a) contacting the sample with a nucleic acid probe which hybridizes under hybridization assay conditions to a nucleic acid target region of a polypeptide having sequences selected from the group consisting of SEQ ID NO:4 to SEQ ID NO:6, said probe comprising the nucleic acid sequence encoding the polypeptide, fragments thereof, and the complements of the sequences and fragments; and (b) detecting the presence or amount of the probe:target region hybrid as an indication of the disease.

In preferred embodiments of the invention, the disease is selected from the group consisting of metabolic diseases and disorders (e.g., type 2 diabetes, obesity, cardiovascular, dyslipidemias, adipogenesis, retinopathies, neuropathies, nephropathies etc.), proliferative diseases and cancers (e.g., different cancers such as breast, colon, lung, etc., tumor growth, tumor invasion, and hyperproliferative disorders such as psoriasis, prostate hyperplasia, etc.), hormonal disorders (e.g., male/female hormonal replacement, polycystic ovarian syndrome, alopecia, etc.), CNS disorders (e.g., degenerative disorders such as Parkinson's, Alzheimer's, etc.), inflammatory conditions (e.g., Chron's disease, arthritis), diseases related to cell differentiation and homeostasis, cardiomyopathy, atherosclerosis, thromboembolic diseases, Sjögren's syndrome, renal failure, periodontal diseases, retinal neovascularization, wound healing, and neurodegenerative diseases including, for example, Alzheimer's disease, multiple sclerosis, Parkinson's disease, and motoneuron disease, among others.

Kits may be designed to detect either expression of polynucleotides encoding MMP expressed in the brain or the MMP proteins themselves in order to identify tissue as being neurological. For example, oligonucleotide hybridization kits can be provided which include a container having an oligonucleotide probe specific for the MMP-specific DNA and optionally, containers with positive and negative controls and/or instructions. Similarly, PCR kits can be provided which include a container having primers specific for the MMP-specific sequences, DNA and optionally, containers with size markers, positive and negative controls and/or instructions.

Hybridization conditions should be such that hybridization occurs only with the genes in the presence of other nucleic acid molecules. Under stringent hybridization conditions only highly complementary nucleic acid sequences hybridize. Preferably, such conditions prevent hybridization of nucleic acids having 1 or 2 mismatches out of 20 contiguous nucleotides. Such conditions are defined supra.

The diseases for which detection of genes in a sample could be diagnostic include diseases in which nucleic acid (DNA and/or RNA) is amplified in comparison to normal cells. By "amplification" is meant increased numbers of DNA or RNA in a cell compared with normal cells.

The diseases that could be diagnosed by detection of nucleic acid in a sample preferably include central nervous system and metabolic diseases. The test samples suitable for nucleic acid probing methods of the present invention include, for example, cells or nucleic acid extracts of cells, or biological fluids. The samples used in the above-described methods will vary based on the assay format, the detection method and the nature of the tissues, cells or extracts to be assayed. Methods for preparing nucleic acid extracts of cells are well known in the art and can be readily adapted in order to obtain a sample that is compatible with the method utilized.

Alternatively, immunoassay kits can be provided which have containers container having antibodies specific for the MMP-protein and optionally, containers with positive and negative controls and/or instructions.

Kits may also be provided useful in the identification of MMP binding partners such as natural ligands or modulators (agonists or antagonists). Substances useful for treatment of disorders or diseases preferably show positive results in one or more in vitro assays for an activity corresponding to treatment of the disease or disorder in question. Substances that modulate the activity of the polypeptides preferably include, but are not limited to, antisense oligonucleotides, agonists and antagonists, and inhibitors of protein kinases.

Methods of Inducing Immune Response

Another aspect of the present invention is directed to methods of inducing an immune response in a mammal against a polypeptide of the invention by administering to the mammal an amount of the polypeptide sufficient to induce an immune response. The amount will be dependent on the animal species, size of the animal, and the like but can be determined by those skilled in the art.

Methods of Identifying Ligands

The invention also provides assays to identify compounds that bind MMP. One such assay comprises the steps of: (a) contacting a composition comprising a MMP with a compound suspected of binding MMP; and (b) measuring binding between the compound and MMP. In one variation, the composition comprises a cell expressing MMP on its surface. In another variation, isolated MMP or cell membranes comprising MMP are employed. The binding may be measured directly, e.g., by using a labeled compound, or may be measured indirectly. Following steps (a) and (b), compounds identified as binding MMP may be tested in other assays including, but not limited to, in vivo models, to confirm or quantitate binding to MMP.

Specific binding molecules, including natural ligands and synthetic compounds, can be identified or developed using isolated or recombinant MMP products, MMP variants, or preferably, cells expressing such products. Binding partners are useful for purifying MMP products and detection or quantification of MMP products in fluid and tissue samples using known immunological procedures. Binding molecules are also manifestly useful in modulating (i.e., blocking, inhibiting or stimulating) biological activities of MMP, especially those activities involved in collagenase or proteinase activity.

The DNA and amino acid sequence information provided by the present invention also makes possible identification of binding partner compounds with which an MMP polypeptide or polynucleotide will interact. Methods to identify binding partner compounds include solution assays, in vitro assays wherein MMP polypeptides are immobilized, and cell-based assays. Identification of binding partner compounds of MMP polypeptides provides candidates for therapeutic or prophylactic intervention in pathologies associated with MMP normal and aberrant biological activity.

The invention includes several assay systems for identifying MMP binding partners. In solution assays, methods of the invention comprise the steps of (a) contacting a MMP polypeptide with one or more candidate binding partner compounds and (b) identifying the compounds that bind to the MMP polypeptide. Identification of the compounds that bind the MMP polypeptide can be achieved by isolating the MMP polypeptide/binding partner complex, and separating the binding partner compound from the MMP polypeptide. An additional step of characterizing the physical, biological, and/or biochemical properties of the binding partner compound is also comprehended in another embodiment of the invention, wherein compounds identified as binding MMP may be tested in other assays including, but not limited to, in vivo models, to confirm or quantitate binding to MMP. In one aspect, the MMP polypeptide/binding partner complex is isolated using an antibody immunospecific for either the MMP polypeptide or the candidate binding partner compound.

In still other embodiments, either the MMP polypeptide or the candidate binding partner compound comprises a label or tag that facilitates its isolation, and methods of the invention to identify binding partner compounds include a step of isolating the MMP polypeptide/binding partner complex through interaction with the label or tag. An exemplary tag of this type is a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

In one variation of an in vitro assay, the invention provides a method comprising the steps of (a) contacting an immobilized MMP polypeptide with a candidate binding partner compound and (b) detecting binding of the candidate compound to the MMP polypeptide. In an alternative embodiment, the candidate binding partner compound is immobilized and binding of MMP is detected. Immobilization is accomplished using any of the methods well known in the art, including covalent bonding to a support, a bead, or a chromatographic resin, as well as non-covalent, high affinity interactions such as antibody binding, or use of streptavidin/biotin binding wherein the immobilized compound includes a biotin moiety. Detection of binding can be accomplished (i) using a radioactive label on the compound that is not immobilized, (ii) using of a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

Another aspect of the present invention is directed to methods of identifying compounds that bind to either MMP or nucleic acid molecules encoding MMP, comprising contacting MMP, or a nucleic acid molecule encoding the same, with a compound, and determining whether the compound binds MMP or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, *Current Protocols in Molecular Biology*, 1999, John Wiley & Sons, NY, which is incorporated herein by reference in its entirety. The compounds to be screened include (which may include compounds which are suspected to bind MMP, or a nucleic acid molecule encoding the same), but are not limited to, extracellular, intracellular, biologic or chemical origin. The methods of the invention also embrace ligands, especially neuropeptides, that are attached to a label, such as a radio-label (e.g., $^{125}I$, $^{35}S$, $^{32}P$, $^{33}P$, $^{3}H$), a fluorescence label, a chemiluminescent label, an enzymic label and an immunogenic label. Modulators falling within the scope of the invention include, but are not limited to, non-peptide molecules such as non-peptide mimetics, non-peptide allosteric effectors, and peptides. The MMP polypeptide or polynucleotide employed in such a test may either be free in solution, attached to a solid support, borne on a cell surface or located intracellularly or associated with a portion of a cell. One skilled in the art can, for example, measure the formation of complexes between MMP and the compound being tested. Alternatively, one skilled in the art can examine the diminution in complex formation between MMP and its substrate caused by the compound being tested.

In another embodiment of the invention, high throughput screening for compounds having suitable binding affinity to MMP is employed. Briefly, large numbers of different test compounds are synthesized on a solid substrate. The peptide test compounds are contacted with MMP and washed. Bound MMP is then detected by methods well known in the art. Purified polypeptides of the invention can also be coated directly onto plates for use in the aforementioned drug screening techniques. In addition, non-neutralizing antibodies can be used to capture the protein and immobilize it on the solid support.

Generally, an expressed MMP can be used for HTS binding assays in conjunction with its defined ligand, in this case the corresponding neuropeptide that activates it. The identified peptide is labeled with a suitable radioisotope, including, but not limited to, $^{125}I$, $^{3}H$, $^{35}S$ or $^{32}P$, by methods that are well known to those skilled in the art. Alternatively, the peptides may be labeled by well-known methods with a suitable fluorescent derivative (Baindur et al., *Drug Dev. Res.*, 1994, 33, 373–398; Rogers, *Drug Discovery Today*, 1997, 2, 156–160). Alternative methods include a scintillation proximity assay (SPA) or a FlashPlate format in which such separation is unnecessary (Nakayama, *Cur. Opinion Drug Disc. Dev.*, 1998, 1, 85–91; Bossé et al., *J. Biomolecular Screening*, 1998, 3, 285–292.). Binding of fluorescent ligands can be detected in various ways, including fluorescence energy transfer (FRET), direct spectrophotofluorometric analysis of bound ligand, or fluorescence polarization (Rogers, *Drug Discovery Today*, 1997, 2, 156–160; Hill, *Cur. Opinion Drug Disc. Dev.*, 1998, 1, 92–97).

Other assays may be used to identify specific ligands of an MMP, including assays that identify ligands of the target protein through measuring direct binding of test ligands to the target protein, as well as assays that identify ligands of target proteins through affinity ultrafiltration with ion spray mass spectroscopy/HPLC methods or other physical and analytical methods. Alternatively, such binding interactions are evaluated indirectly using the yeast two-hybrid system described in Fields et al., Nature, 340:245–246 (1989), and Fields et al., Trends in Genetics, 10:286–292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA binding proteins, to identify peptides that bind to a protein, and to screen for drugs. The two-hybrid system exploits the ability of a pair of interacting proteins to bring a transcription activation domain into close proximity with a DNA binding domain that binds to an upstream activation sequence (UAS) of a reporter gene, and is generally performed in yeast. The assay requires the construction of two hybrid genes encoding (1) a DNA-binding domain that is fused to a first protein and (2) an activation domain fused to a second protein. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of the first and second proteins tethers the activation domain to the UAS, activating transcription of the reporter gene. For example, when the first protein is a MMP gene product, or fragment thereof, that is known to interact with another protein or nucleic acid, this assay can be used to detect agents that interfere with the binding interaction. Expression of the reporter gene is monitored as different test agents are added to the system. The presence of an inhibitory agent results in lack of a reporter signal.

The yeast two-hybrid assay can also be used to identify proteins that bind to the gene product. In an assay to identify proteins that bind to a MMP, or fragment thereof, a fusion polynucleotide encoding both a MMP (or fragment) and a UAS binding domain (i.e., a first protein) may be used. In addition, a large number of hybrid genes each encoding a different second protein fused to an activation domain are produced and screened in the assay. Typically, the second protein is encoded by one or more members of a total cDNA or genomic DNA fusion library, with each second protein-coding region being fused to the activation domain. This system is applicable to a wide variety of proteins, and it is not even necessary to know the identity or function of the second binding protein. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method that distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules.

Another method for identifying ligands of a target protein is described in Wieboldt et al., Anal. Chem., 69:1683–1691 (1997), incorporated herein by reference. This technique screens combinatorial libraries of 20–30 agents at a time in solution phase for binding to the target protein. Agents that bind to the target protein are separated from other library components by simple membrane washing. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide that shares one or more antigenic determinants with MMP. Radiolabeled competitive binding studies are described in A. H. Lin et al. *Antimicrobial Agents and Chemotherapy*, 1997, vol. 41, no. 10. pp. 2127–2131, the disclosure of which is incorporated herein by reference in its entirety.

Identification of Modulating Agents

The invention also provides methods for identifying a modulator of binding between a MMP and a MMP binding partner, comprising the steps of: (a) contacting a MMP binding partner and a composition comprising a MMP in the presence and in the absence of a putative modulator compound; (b) detecting binding between the binding partner and the MMP; and (c) identifying a putative modulator compound or a modulator compound in view of decreased or increased binding between the binding partner and the MMP in the presence of the putative modulator, as compared to binding in the absence of the putative modulator. Following steps (a) and (b), compounds identified as modulating binding between MMP and an MMP binding partner may be tested in other assays including, but not limited to, in vivo models, to confirm or quantitate modulation of binding to MMP.

MMP binding partners that stimulate MMP activity are useful as agonists in disease states or conditions characterized by insufficient MMP activity. e.g., as a result of insufficient activity of a MMP ligand). MMP binding partners that block ligand-mediated MMP signaling are useful as MMP antagonists to treat disease states or conditions characterized by excessive MMP signaling. In addition MMP modulators in general, as well as MMP polynucleotides and polypeptides, are useful in diagnostic assays for such diseases or conditions.

In another aspect, the invention provides methods for treating a disease or abnormal condition by administering to a patient in need of such treatment a substance that modulates the activity or expression of a polypeptide having sequences selected from the group consisting of SEQ ID NO:4 to SEQ ID NO:6.

Agents that modulate (i.e., increase, decrease, or block) MMP activity or expression may be identified by incubating a putative modulator with a cell containing an MMP polypeptide or polynucleotide and determining the effect of the putative modulator on MMP activity or expression. The selectivity of a compound that modulates the activity of MMP can be evaluated by comparing its effects on MMP to its effect on other MMP compounds. Following identification of compounds that modulate MMP activity or expression, such compounds may be further tested in other assays including, but not limited to, in vivo models, in order to confirm or quantitate their activity. Selective modulators may include, for example, antibodies and other proteins, peptides, or organic molecules that specifically bind to an MMP polypeptide or a MMP-encoding nucleic acid. Modulators of MMP activity will be therapeutically useful in treatment of diseases and physiological conditions in which normal or aberrant MMP activity is involved. MMP polynucleotides, polypeptides, and modulators may be used in the treatment of such diseases and conditions as metabolic diseases and disorders (e.g., type 2 diabetes, obesity, cardiovascular, dyslipidemias, adipogenesis, retinopathies, neuropathies, nephropathies etc.), proliferative diseases and cancers (e.g., different cancers such as breast, colon, lung, etc., tumor growth, tumor invasion, and hyperproliferative disorders such as psoriasis, prostate hyperplasia, etc.), hormonal disorders (e.g., male/female hormonal replacement, polycystic ovarian syndrome, alopecia, etc.), CNS disorders (e.g., degenerative disorders such as Parkinson's, Alzheimer's, etc.), inflammatory conditions (e.g., Chron's disease, arthritis), diseases related to cell differentiation and homeostasis, cardiomyopathy, atherosclerosis, thromboembolic diseases, Sjögren's syndrome, renal failure, periodontal diseases, retinal neovascularization, wound healing, and neurodegenerative diseases including, for example, Alzheimer's disease, multiple sclerosis, Parkinson's disease, and motoneuron disease, among others.

Methods of the invention to identify modulators include variations on any of the methods described above to identify binding partner compounds, the variations including techniques wherein a binding partner compound has been identified and the binding assay is carried out in the presence and absence of a candidate modulator. A modulator is identified in those instances where binding between the MMP polypeptide and the binding partner compound changes in the presence of the candidate modulator compared to binding in the absence of the candidate modulator compound. A modulator that increases binding between the MMP polypeptide and the binding partner compound is described as an enhancer or activator, and a modulator that decreases binding between the MMP polypeptide and the binding partner compound is described as an inhibitor. Following identification of modulators, such compounds may be further tested in other assays including, but not limited to, in vivo models, in order to confirm or quantitate their activity as modulators.

The invention also comprehends high-throughput screening (HTS) assays to identify compounds that interact with or inhibit biological activity (i.e., affect enzymatic activity, binding activity, etc.) of a MMP polypeptide. HTS assays permit screening of large numbers of compounds in an efficient manner. Cell-based HTS systems are contemplated to investigate MMP-ligand interaction. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the MMP polypeptide.

Another aspect of the present invention is directed to methods of identifying compounds which modulate (i.e., increase or decrease) an activity of MMP comprising contacting MMP with a compound, and determining whether the compound modifies activity of MMP. The activity in the presence of the test compared is measured to the activity in the absence of the test compound. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity. Following the identification of compounds that modulate an activity of MMP, such compounds can be further tested in other assays including, but not limited to, in vivo models, in order to confirm or quantitate their activity.

The present invention is particularly useful for screening compounds by using MMP in any of a variety of drug screening techniques. The compounds to be screened include (which may include compounds which are suspected to modulate MMP activity), but are not limited to, extracellular, intracellular, biologic or chemical origin. The MMP polypeptide employed in such a test may be in any form, preferably, free in solution, attached to a solid support, borne on a cell surface or located intracellularly. One skilled in the art can, for example, measure the formation of complexes between MMP and the compound being tested. Alternatively, one skilled in the art can examine the diminution in complex formation between MMP and its substrate caused by the compound being tested.

The activity of MMP polypeptides of the invention can be determined by, for example, examining the ability to bind or be activated by appropriate ligands, such as low molecular weight steroids and fatty acids. The activity of the MMPs can be assayed by, for example, competition-binding assays and coactivator-interaction assays (see, e.g., Makishima et al, 1999, Science, 284, 1362–1365; Parks et al., Science, 284, 1365–1367). Alternatively, the activity of MMP polypeptides can be assayed by examining their ability to cleave a known MMP substrate.

The modulators of the invention exhibit a variety of chemical structures, which can be generally grouped into non-peptide mimetics of natural MMP ligands, peptide and non-peptide allosteric effectors of MMPs, and peptides that may function as activators or inhibitors (competitive, uncompetitive and non-competitive) (e.g., antibody products) of MMPs. The invention does not restrict the sources for suitable modulators, which may be obtained from natural sources such as plant, animal or mineral extracts, or non-natural sources such as small molecule libraries, including the products of combinatorial chemical approaches to library construction, and peptide libraries.

Other assays can be used to examine enzymatic activity including, but not limited to, photometric, radiometric, HPLC, electrochemical, and the like, which are described in, for example, *Enzyme Assays: A Practical Approach*, eds. R. Eisenthal and M. J. Danson, 1992, Oxford University Press, which is incorporated herein by reference in its entirety.

The use of cDNAs encoding MMPs in drug discovery programs is well-known; assays capable of testing thousands of unknown compounds per day in high-throughput screens (HTSs) are thoroughly documented. The literature is replete with examples of the use of radiolabeled ligands in HTS binding assays for drug discovery (see Williams, *Medicinal Research Reviews*, 1991, 11, 147–184; Sweetnam, et al., *J. Natural Products*, 1993, 56, 441–455 for review).

A variety of heterologous systems is available for functional expression of recombinant polypeptides that are well known to those skilled in the art. Such systems include bacteria (Strosberg, et al., *Trends in Pharmacological Sciences*, 1992, 13, 95–98), yeast (Pausch, *Trends in Biotechnology*, 1997, 15, 487–494), several kinds of insect cells (Vanden Broeck, *Int. Rev. Cytology*, 1996, 164, 189–268), amphibian cells (Jayawickreme et al., *Current Opinion in Biotechnology*, 1997, 8, 629–634) and several mammalian cell lines (CHO, HEK-293, COS, etc.; see Gerhardt, et al., *Eur. J. Pharmacology*, 1997, 334, 1–23). These examples do not preclude the use of other possible cell expression systems, including cell lines obtained from nematodes (PCT application WO 98/37177).

In preferred embodiments of the invention, methods of screening for compounds that modulate MMP activity comprise contacting test compounds with MMP and assaying for the presence of a complex between the compound and MMP. In such assays, the ligand is typically labeled. After suitable incubation, free ligand is separated from that present in bound form, and the amount of free or uncomplexed label is a measure of the ability of the particular compound to bind to MMP.

The invention contemplates a multitude of assays to screen and identify inhibitors of ligand binding to MMPs. In one example, the MMP is immobilized and interaction with a binding partner is assessed in the presence and absence of a candidate modulator such as an inhibitor compound. In another example, interaction between the MMP and its binding partner is assessed in a solution assay, both in the presence and absence of a candidate inhibitor compound. In either assay, an inhibitor is identified as a compound that decreases binding between the MMP and its binding partner. Following the identification of compounds which inhibit ligand binding to MMP, such compounds may be further tested in other assays including, but not limited to, in vivo models, in order to confirm or quantitate their activity. Another contemplated assay involves a variation of the dihybrid assay wherein an inhibitor of protein/protein interactions is identified by detection of a positive signal in a transformed or transfected host cell, as described in PCT publication number WO 95/20652, published Aug. 3, 1995.

Candidate modulators contemplated by the invention include compounds selected from libraries of either potential activators or potential inhibitors. There are a number of different libraries used for the identification of small molecule modulators, including: (1) chemical libraries, (2) natural product libraries, and (3) combinatorial libraries comprised of random peptides, oligonucleotides or organic molecules. Chemical libraries consist of random chemical structures, some of which are analogs of known compounds or analogs of compounds that have been identified as "hits" or "leads" in other drug discovery screens, some of which are derived from natural products, and some of which arise from non-directed synthetic organic chemistry. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof For a review, see Science 282:63–68 (1998). Combinatorial libraries are composed of large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701–707 (1997). Identification of modulators through use of the various libraries described herein permits modification of the candidate "hit" (or "lead") to optimize the capacity of the "hit" to modulate activity.

Still other candidate inhibitors contemplated by the invention can be designed and include soluble forms of binding partners, as well as such binding partners as chimeric, or fusion, proteins. A "binding partner" as used herein broadly encompasses non-peptide modulators, as well as such peptide modulators as neuropeptides other than natural ligands, antibodies, antibody fragments, and modified compounds comprising antibody domains that are immunospecific for the expression product of the identified MMP gene.

The polypeptides of the invention are employed as a research tool for identification, characterization and purification of interacting, regulatory proteins. Appropriate labels are incorporated into the polypeptides of the invention by various methods known in the art and the polypeptides are used to capture interacting molecules. For example, molecules are incubated with the labeled polypeptides, washed to remove unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identify the captured molecule or to design degenerate oligonucleotides for cloning the corresponding gene from an appropriate cDNA library.

Alternatively, compounds may be identified which exhibit similar properties to the ligand for the MMP of the invention, but which are smaller and exhibit a longer half time than the endogenous ligand in a human or animal body. When an organic compound is designed, a molecule according to the invention is used as a "lead" compound. The design of mimetics to known pharmaceutically active compounds is a well-known approach in the development of pharmaceuticals based on such "lead" compounds. Mimetic design, synthesis and testing are generally used to avoid randomly screening a large number of molecules for a target property. Furthermore, structural data deriving from the analysis of the deduced amino acid sequences encoded by the DNAs of the present invention are useful to design new drugs, more specific and therefore with a higher pharmacological potency.

Comparison of the protein sequences of the present invention with the sequences present in all the available databases showed homology with the known MMPs. Accordingly, computer modeling can be used to develop a putative tertiary structure of the proteins of the invention based on the available information of the conserved domains of the polypeptides of the present invention. Thus, novel ligands based on the predicted structure of MMP can be designed.

In a particular embodiment, the novel molecules identified by the screening methods according to the invention are low molecular weight organic molecules, in which case a composition or pharmaceutical composition can be prepared thereof for oral intake, such as in tablets. The compositions, or pharmaceutical compositions, comprising the nucleic acid molecules, vectors, polypeptides, antibodies and compounds identified by the screening methods described herein, can be prepared for any route of administration including, but not limited to, oral, intravenous, cutaneous, subcutaneous, nasal, intramuscular or intraperitoneal. The nature of the carrier or other ingredients will depend on the specific route of administration and particular embodiment of the invention to be administered. Examples of techniques and protocols that are useful in this context are, inter alia, found in Remington's Pharmaceutical Sciences, 16$^{th}$ edition, Osol, A (ed.), 1980, which is incorporated herein by reference in its entirety.

The dosage of these low molecular weight compounds will depend on the disease state or condition to be treated and other clinical factors such as weight and condition of the human or animal and the route of administration of the compound. For treating human or animals, between approximately 0.5 mg/kg of body weight to 500 mg/kg of body weight of the compound can be administered. Therapy is typically administered at lower dosages and is continued until the desired therapeutic outcome is observed.

The present compounds and methods, including nucleic acid molecules, polypeptides, antibodies, compounds identified by the screening methods described herein, have a variety of pharmaceutical applications and may be used, for example, to treat or prevent unregulated cellular growth, such as cancer cell and tumor growth. In a particular embodiment, the present molecules are used in gene therapy. For a review of gene therapy procedures, see e.g. Anderson, *Science*, 1992, 256, 808–813, which is incorporated herein by reference in its entirety.

The present invention also encompasses a method of agonizing (stimulating) or antagonizing a MMP natural binding partner associated activity in a mammal comprising administering to said mammal an agonist or antagonist to one of the above disclosed polypeptides in an amount sufficient to effect said agonism or antagonism. One embodiment of the present invention, then, is a method of treating diseases in a mammal with an agonist or antagonist of the protein of the present invention comprises administering the agonist or antagonist to a mammal in an amount sufficient to agonize or antagonize MMP-associated functions.

Exemplary diseases and conditions amenable to treatment based on the present invention include, but are not limited to, metabolic diseases and disorders (e.g., type 2 diabetes, obesity, cardiovascular, dyslipidemias, adipogenesis, retinopathies, neuropathies, nephropathies etc.), proliferative diseases and cancers (e.g., different cancers such as breast, colon, lung, etc., tumor growth, tumor invasion, and hyperproliferative disorders such as psoriasis, prostate hyperplasia, etc.), hormonal disorders (e.g., male/female hormonal replacement, polycystic ovarian syndrome, alopecia, etc.), CNS disorders (e.g., degenerative disorders such as Parkinson's, Alzheimer's, etc.), inflammatory conditions (e.g., Chron's disease, arthritis), diseases related to cell differentiation and homeostasis, cardiomyopathy, atherosclerosis, thromboembolic diseases, Sjögren's syndrome, renal failure, periodontal diseases, retinal neovascularization, wound healing, and neurodegenerative diseases including, for example, Alzheimer's disease, multiple sclerosis, Parkinson's disease, and motoneuron disease, among others.

Methods of determining the dosages of compounds to be administered to a patient and modes of administering compounds to an organism are disclosed in U.S. application Ser. No. 08/702,282, filed Aug. 23, 1996 and International patent publication number WO 96/22976, published Aug. 1 1996, both of which are incorporated herein by reference in their entirety, including any drawings, figures or tables. Those skilled in the art will appreciate that such descriptions are applicable to the present invention and can be easily adapted to it.

The proper dosage depends on various factors such as the type of disease being treated, the particular composition being used and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and bio-distribution of the drug and metabolites in the plasma, tumors and major organs can also be determined to facilitate the selection of drugs most appropriate to inhibit a disorder. Such measurements can be carried out. For example, HPLC analysis can be performed on the plasma of animals treated with the drug and the location of radiolabeled compounds can be determined using detection methods such as X-ray, CAT scan and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal model as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, Journal of American Veterinary Medical Assoc., 202:229–249, 1993). Representative animals from each treatment group can then be examined by gross necropsy for immediate evidence of metastasis, unusual illness or toxicity. Gross abnormalities in tissue are noted and tissues are examined histologically. Compounds causing a reduction in body weight or blood components are less preferred, as are compounds having an adverse effect on major organs. In general, the greater the adverse effect the less preferred the compound.

For the treatment of many diseases, the expected daily dose of a hydrophobic pharmaceutical agent is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness. Plasma levels should reflect the potency of the drug. Generally, the more potent the compound the lower the plasma levels necessary to achieve efficacy.

As discussed above, it is well known that MMPs are expressed in many different tissues and regions, including in the brain. MMP mRNA transcripts may found in many other tissues, including, but not limited to pancreas (and particularly pancreatic islet tissue), pituitary, skeletal muscle, adipose tissue, liver, and thyroid, and may be found in many other tissues.

Sequences selected from the group consisting of SEQ ID NO:1 to SEQ ID NO:3 will, as detailed above, enable screening the endogenous hormones/ligands which activate, agonize, or antagonize MMP and for compounds with potential utility in treating disorders including, but not limited to, metabolic diseases and disorders (e.g., type 2 diabetes, obesity, cardiovascular, dyslipidemias, adipogenesis, retinopathies, neuropathies, nephropathies etc.), proliferative diseases and cancers (e.g., different cancers such as breast, colon, lung, etc., tumor growth, tumor invasion, and hyperproliferative disorders such as psoriasis, prostate hyperplasia, etc.), hormonal disorders (e.g., male/female hormonal replacement, polycystic ovarian syndrome, alopecia, etc.), CNS disorders (e.g., degenerative disorders such as Parkinson's, Alzheimer's, etc.), inflammatory conditions (e.g., Chron's disease, arthritis), diseases related to cell differentiation and homeostasis, cardiomyopathy, atherosclerosis, thromboembolic diseases, Sjögren's syndrome, renal failure, periodontal diseases, retinal neovascularization, wound healing, and neurodegenerative diseases including, for example, Alzheimer's disease, multiple sclerosis, Parkinson's disease, and motoneuron disease, among others.

The attached Sequence Listing contains the sequences of the polynucleotides and polypeptides of the invention and is incorporated herein by reference in its entirety.

Methods of Screening Human Subjects

Thus in yet another embodiment, the invention provides genetic screening procedures that entail analyzing a person's genome—in particular their alleles for the MMPs of the invention—to determine whether the individual possesses a genetic characteristic found in other individuals that are considered to be afflicted with, or at risk for, developing a mental disorder or disease of the brain that is suspected of having a hereditary component. For example, in one embodiment, the invention provides a method for determining a potential for developing a disorder affecting the brain in a human subject comprising the steps of analyzing the coding sequence of one or more MMP genes from the human subject; and determining development potential for the disorder in said human subject from the analyzing step.

More particularly, the invention provides a method of screening a human subject to diagnose a disorder affecting the brain or genetic predisposition therefor, comprising the steps of: (a) assaying nucleic acid of a human subject to determine a presence or an absence of a mutation altering the amino acid sequence, expression, or biological activity of at least one MMP that is expressed in the brain, wherein the MMP comprises an amino acid sequence selected from the group consisting of SEQ ID NO:1 to SEQ ID NO:3, or an allelic variant thereof, and wherein the nucleic acid corresponds to the gene encoding the MMP; and (b) diagnosing the disorder or predisposition from the presence or absence of said mutation, wherein the presence of a mutation altering the amino acid sequence, expression, or biological activity of allele in the nucleic acid correlates with an increased risk of developing the disorder.

By "human subject" is meant any human being, human embryo, or human fetus. It will be apparent that methods of the present invention will be of particular interest to individuals that have themselves been diagnosed with a disorder affecting the brain or have relatives that have been diagnosed with a disorder affecting the brain.

By "screening for an increased risk" is meant determination of whether a genetic variation exists in the human subject that correlates with a greater likelihood of developing a disorder affecting the brain than exists for the human population as a whole, or for a relevant racial or ethnic human sub-population to which the individual belongs. Both positive and negative determinations (i.e., determinations that a genetic predisposition marker is present or is absent) are intended to fall within the scope of screening methods of the invention. In preferred embodiments, the presence of a mutation altering the sequence or expression of at least one MMP allele in the nucleic acid is correlated with an increased risk of developing mental disorder, whereas the absence of such a mutation is reported as a negative determination.

The "assaying" step of the invention may involve any techniques available for analyzing nucleic acid to determine its characteristics, including but not limited to well-known techniques such as single-strand conformation polymorphism analysis (SSCP) [Orita et al., *Proc Natl. Acad. Sci. USA*, 86: 2766–2770 (1989)]; heteroduplex analysis [White et al., *Genomics*, 12: 301–306 (1992)]; denaturing gradient gel electrophoresis analysis [Fischer et al., *Proc. Natl. Acad. Sci. USA*, 80: 1579–1583 (1983); and Riesner et al., *Electrophoresis*, 10: 377–389 (1989)]; DNA sequencing; RNase cleavage [Myers et al., *Science*, 230: 1242–1246 (1985)]; chemical cleavage of mismatch techniques [Rowley et al., *Genomics*, 30: 574–582 (1995); and Roberts et al., *Nucl. Acids Res.*, 25: 3377–3378 (1997)]; restriction fragment length polymorphism analysis; single nucleotide primer extension analysis [Shumaker et al., *Hum. Mutat.*, 7: 346–354 (1996); and Pastinen et al., *Genome Res.*, 7: 606–614 (1997)]; 5' nuclease assays [Pease et al., *Proc. Natl. Acad. Sci. USA*, 91:5022–5026 (1994)]; DNA Microchip analysis [Ramsay, G., *Nature Biotechnology*, 16: 40–48 (1999); and Chee et al., U.S. Pat. No. 5,837,832]; and ligase chain reaction [Whiteley et al., U.S. Pat. No. 5,521,065]. [See generally, Schafer and Hawkins, *Nature Biotechnology*, 16: 33–39 (1998).] All of the foregoing documents are hereby incorporated by reference in their entirety.

Thus, in one preferred embodiment involving screening MMP sequences, for example, the assaying step comprises at least one procedure selected from the group consisting of: (a) determining a nucleotide sequence of at least one codon of at least one MMP allele of the human subject; (b) performing a hybridization assay to determine whether nucleic acid from the human subject has a nucleotide sequence identical to or different from one or more reference sequences; (c) performing a polynucleotide migration assay to determine whether nucleic acid from the human subject has a nucleotide sequence identical to or different from one or more reference sequences; and (d) performing a restriction endonuclease digestion to determine whether nucleic acid from the human subject has a nucleotide sequence identical to or different from one or more reference sequences.

In a highly preferred embodiment, the assaying involves sequencing of nucleic acid to determine nucleotide sequence thereof, using any available sequencing technique. [See, e.g., Sanger et al., *Proc. Natl. Acad. Sci. (USA)*, 74: 5463–5467 (1977) (dideoxy chain termination method); Mirzabekov, *TIBTECH*, 12: 27–32 (1994) (sequencing by hybridization); Drmanac et al., *Nature Biotechnology*, 16: 54–58 (1998); U.S. Pat. No. 5,202,231; and *Science*, 260: 1649–1652 (1993) (sequencing by hybridization); Kielec-zawa et al., *Science*, 258: 1787–1791 (1992) (sequencing by primer walking); (Douglas et al., *Biotechniques*, 14: 824–828 (1993) (Direct sequencing of PCR products); and Akane et al., *Biotechniques* 16: 238–241 (1994); Maxam and Gilbert, *Meth. Enzymol.*, 65: 499–560 (1977) (chemical termination sequencing), all incorporated herein by reference.] The analysis may entail sequencing of the entire MMP gene genomic DNA sequence, or portions thereof; or sequencing of the entire MMP coding sequence or portions thereof. In some circumstances, the analysis may involve a determination of whether an individual possesses a particular allelic variant, in which case sequencing of only a small portion of nucleic acid—enough to determine the sequence of a particular codon characterizing the allelic variant—is sufficient. This approach is appropriate, for example, when assaying to determine whether one family member inherited the same allelic variant that has been previously characterized for another family member, or, more generally, whether a person's genome contains an allelic variant that has been previously characterized and correlated with a mental disorder having a heritable component.

In another highly preferred embodiment, the assaying step-comprises performing a hybridization assay to determine whether nucleic acid from the human subject has a nucleotide sequence identical to or different from one or more reference sequences. In a preferred embodiment, the hybridization involves a determination of whether nucleic acid derived from the human subject will hybridize with one or more oligonucleotides, wherein the oligonucleotides have nucleotide sequences that correspond identically to a portion of the MMP gene sequence taught herein, or that correspond identically except for one mismatch. The hybridization conditions are selected to differentiate between perfect sequence complementarity and imperfect matches differing by one or more bases. Such hybridization experiments thereby can provide single nucleotide polymorphism sequence information about the nucleic acid from the human subject, by virtue of knowing the sequences of the oligonucleotides used in the experiments.

Several of the techniques outlined above involve an analysis wherein one performs a polynucleotide migration assay, e.g., on a polyacrylamide electrophoresis gel (or in a capillary electrophoresis system), under denaturing or non-denaturing conditions. Nucleic acid derived from the human subject is subjected to gel electrophoresis, usually adjacent to (or co-loaded with) one or more reference nucleic acids, such as reference MMP encoding sequences having a coding sequence identical to all or a portion of SEQ ID NOS: 1 to 3 (or identical except for one known polymorphism). The nucleic acid from the human subject and the reference sequence(s) are subjected to similar chemical or enzymatic treatments and then electrophoresed under conditions whereby the polynucleotides will show a differential migration pattern, unless they contain identical sequences. [See generally Ausubel et al. (eds.), *Current Protocols in Molecular Biology*, New York: John Wiley & Sons, Inc. (1987–1999); and Sambrook et al., (eds.), Molecular Cloning, *A Laboratory Manual*, Cold Spring Harbor, N.Y.: Cold Spring Harbor Laboratory Press (1989), both incorporated herein by reference in their entirety.]

In the context of assaying, the term "nucleic acid of a human subject" is intended to include nucleic acid obtained directly from the human subject (e.g., DNA or RNA obtained from a biological sample such as a blood, tissue, or other cell or fluid sample); and also nucleic acid derived from nucleic acid obtained directly from the human subject. By way of non-limiting examples, well known procedures exist for creating cDNA that is complementary to RNA derived from a biological sample from a human subject, and for amplifying (e.g., via polymerase chain reaction (PCR)) DNA or RNA derived from a biological sample obtained from a human subject. Any such derived polynucleotide which retains relevant nucleotide sequence information of the human subject's own DNA/RNA is intended to fall within the definition of "nucleic acid of a human subject" for the purposes of the present invention.

In the context of assaying, the term "mutation" includes addition, deletion, and/or substitution of one or more nucleotides in the MMP gene sequence (e.g., as compared to the MMP-encoding sequences set forth of SEQ ID NO:1 to SEQ ID NO:3, and other polymorphisms that occur in introns (where introns exist) and that are identifiable via sequencing, restriction fragment length polymorphism, or other techniques. The various activity examples provided herein permit determination of whether a mutation modulates activity of the relevant MMP in the presence or absence of various test substances.

In a related embodiment, the invention provides methods of screening a person's genotype with respect to the MMP of the invention, and correlating such genotypes with diagnoses for disease or with predisposition for disease (for genetic counseling). For example, the invention provides a method of screening for an MMP hereditary mental disorder genotype in a human patient, comprising the steps of: (a) providing a biological sample comprising nucleic acid from the patient, the nucleic acid including sequences corresponding to said patient's MMP alleles; (b) analyzing the nucleic acid for the presence of a mutation or mutations; (c) determining a MMP genotype from the analyzing step; and (d) correlating the presence of a mutation in an MMP allele with a hereditary mental disorder genotype. In a preferred embodiment, the biological sample is a cell sample containing human cells that contain genomic DNA of the human subject. The analyzing can be performed analogously to the assaying described in preceding paragraphs. For example, the analyzing comprises sequencing a portion of the nucleic acid (e.g., DNA or RNA), the portion comprising at least one codon of the MMP alleles.

Although more time consuming and expensive than methods involving nucleic acid analysis, the invention also may be practiced by assaying one or more proteins of a human subject to determine the presence or absence of an amino acid sequence variation in MMP protein from the human subject. Such protein analyses may be performed, e.g., by fragmenting MMP protein via chemical or enzymatic methods and sequencing the resultant peptides; or by Western analyses using an antibody having specificity for a particular allelic variant of the MMP.

The invention also provides materials that are useful for performing methods of the invention. For example, the present invention provides oligonucleotides useful as probes in the many analyzing techniques described above. In general, such oligonucleotide probes comprise 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides that have a sequence that is identical, or exactly complementary, to a portion of a human MMP gene sequence taught herein (or allelic variant thereof), or that is identical or exactly complementary except for one nucleotide substitution. In a preferred embodiment, the oligonucleotides have a sequence that corresponds in the foregoing manner to a human MMP coding sequence taught herein, and in particular, the coding sequences set forth in SEQ ID NO:1 to SEQ ID NO:3. In one variation, an oligonucleotide probe of the invention is purified and isolated. In another variation, the oligonucleotide probe is labeled, e.g., with a radioisotope, chromophore, or fluorophore. In yet another variation, the probe is covalently attached to a solid support. [See generally Ausubel et al. and Sambrook et al., supra.]

In a related embodiment, the invention provides kits comprising reagents that are useful for practicing methods of the invention. For example, the invention provides a kit for screening a human subject to diagnose a mental disorder or a genetic predisposition therefor, comprising, in association: (a) an oligonucleotide useful as a probe for identifying polymorphisms in a human MMP gene, the oligonucleotide comprising 6-50 nucleotides that have a sequence that is identical or exactly complementary to a portion of a human MMP gene sequence or MMP coding sequence, except for one sequence difference selected from the group consisting of a nucleotide addition, a nucleotide deletion, or nucleotide substitution; and (b) a media packaged with the oligonucleotide containing information identifying polymorphisms identifiable with the probe that correlate with mental disorder or a genetic predisposition therefor. Exemplary information-containing media include printed paper package inserts or packaging labels; and magnetic and optical storage media that are readable by computers or machines used by practitioners who perform genetic screening and counseling services. The practitioner uses the information provided in the media to correlate the results of the analysis with the oligonucleotide with a diagnosis. In a preferred variation, the oligonucleotide is labeled.

In still another embodiment, the invention provides methods of identifying those allelic variants of MMP of the invention that correlate with mental disorders. For example, the invention provides a method of identifying an MMP allelic variant that correlates with a mental disorder, comprising steps of: (a) providing a biological sample comprising nucleic acid from a human patient diagnosed with a mental disorder, or from the patient's genetic progenitors or progeny; (b) analyzing the nucleic acid for the presence of a mutation or mutations in at least one MMP that is expressed in the brain, wherein the at least one MMP comprises an amino acid sequence selected from the group consisting of SEQ ID NO:1 to SEQ ID NO:3 or an allelic variant thereof, and wherein the nucleic acid includes sequence corresponding to the gene or genes encoding the at least one MMP; (c) determining a genotype for the patient for the at least one MMP from said analyzing step; and (d) identifying an allelic variant that correlates with the mental disorder from the determining step. To expedite this process, it may be desirable to perform linkage studies in the patients (and possibly their families) to correlate chromosomal markers with disease states. The chromosomal localization data provided herein facilitates identifying an involved MMP with a chromosomal marker.

The foregoing method can be performed to correlate the MMP of the invention to a number of disorders having hereditary components that are causative or that predispose persons to the disorder. For example, in one preferred variation, the disorder is a mental disorder.

Also contemplated as part of the invention are polynucleotides that comprise the allelic variant sequences identified by such methods, and polypeptides encoded by the allelic variant sequences, and oligonucleotide and oligopeptide fragments thereof that embody the mutations that have been identified. Such materials are useful in in vitro cell-free and cell-based assays for identifying lead compounds and therapeutics for treatment of the disorders. For example, the variants are used in activity assays, binding assays, and assays to screen for activity modulators described herein. In one preferred embodiment, the invention provides a purified and isolated polynucleotide comprising a nucleotide sequence encoding a MMP allelic variant identified according to the methods described above; and an oligonucleotide that comprises the sequences that differentiate the allelic variant from the MMP sequences set forth in SEQ ID NO:1 to SEQ ID NO:3. The invention also provides a vector comprising the polynucleotide (preferably an expression vector); and a host cell transformed or transfected with the polynucleotide or vector. The invention also provides an isolated cell line that is expressing the allelic variant MMP polypeptide; purified cell membranes from such cells; purified polypeptide; and synthetic peptides that embody the allelic variation amino acid sequence. In one particular embodiment, the invention provides a purified polynucleotide comprising a nucleotide sequence encoding an MMP protein of a human that is affected with a mental disorder; wherein said polynucleotide hybridizes to the complement of a sequence selected from the group consisting of SEQ ID NO:1 to SEQ ID NO:3 under the following hybridization conditions: (a) hybridization for 16 hours at 42° C. in a hybridization solution comprising 50% formamide, 1% SDS, 1 M NaCl, 10% dextran sulfate and (b) washing 2 times for 30 minutes at 60EC in a wash solution comprising 0.1×SSC and 1% SDS; and wherein the polynucleotide encodes an MMP amino acid sequence that differs from a sequence selected from the group consisting of SEQ ID NO:4 to SEQ ID NO:6, by at least one residue.

An exemplary assay for using the allelic variants is a method for identifying a modulator of MMP biological activity, comprising the steps of: (a) contacting a cell expressing the allelic variant in the presence and in the absence of a putative modulator compound; (b) measuring MMP biological activity in the cell; and (c) identifying a putative modulator compound in view of decreased or increased MMP biological activity in the presence versus absence of the putative modulator.

Additional features of the invention will be apparent from the following Examples. Examples 1 is actual while the remaining Examples are prophetic. Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

EXAMPLE 1

Identification of MMP

A. Database Search

The Incyte LifeSeq databases LGTemplatesAUG1999, LGTemplatesOCT1999, and LGTemplatesDEC1999, and the Celera database Releases 1.04–1.05 were searched using BLAST and nucleotide/protein sequence from known MMPs. A collection of query amino acid sequences derived from MMPs was used to search the DNA sequence databases using TBLASTN and alignments with an E-value lower than $10^{-5}$ were collected from each BLAST search. The new sequences found were then BLAST searched against proprietary databases in order to eliminate known MMPs and identify novel MMPs.

Briefly, the BLAST algorithm (Basic Local Alignment Search Tool) is suitable for determining sequence similarity (Altschul et al., J. Mol. Biol., 1990, 215, 403–410, which is incorporated herein by reference in its entirety). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The BLAST algorithm parameters W, T and X determine the sensitivity and speed of the alignment. The BLAST program uses as defaults a word length (W) of 11, the BLOSUM62 scoring matrix (see Henikoff et al., Proc. Natl. Acad. Sci. USA, 1992, 89, 10915–10919, which is incorporated herein by reference in its entirety) alignments (B) of 50, expectation (E) of 10, M=5, N=4, and a comparison of both strands.

The BLAST algorithm (Karlin et al., Proc. Natl. Acad. Sci. USA, 1993, 90, 5873–5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a MMP gene or cDNA if the smallest sum probability in comparison of the test nucleic acid to an MMP nucleic acid is less than about 1 to about $10^{-5}$.

The following Table 5 contains the sequences of the polynucleotides and polypeptides of the invention. The coding regions within the polynucleotide sequences are identified by underlining.

TABLE 5

The following DNA sequence MMPU1 <SEQ ID NO. 1> was identified in *H. sapiens*.

GCTTCAGCTGAAGAAAGAGAGGA<u>ATGAAGCGCCTTCTGCTTCTGTGTTTGTTCTTTATAACATTTTCTTCT</u>

<u>GCATTTCCGTTAGTGCGGATGACGGAAAATGAAGAAAATATGCAACTGGCTCAGGCATATCTCAACCAGTT</u>

<u>GTACTCTCTTGAAATAGAAGGGAATCATCTTGTTCAAAGCAAGAATAGGAGTCTCATAGATGACAAAATTC</u>

<u>GGGAAATGCAAGCATTTTTTGGATTGACAGTGACTGGAAAACTGGACTCAAACACCCTTGAGATCATGAAG</u>

<u>ACAGCCAGGTGTGGGGTGCCTGATGTGGGCCAGTATGGCTACACCCTCCGTGGGTGGAGAAAATACAACCT</u>

<u>CACCTAGAGAATAATAAACTATACTCCGGATATGGCACGAGCTGCTGTGGATGAGGCTATCCAAGAAGGTT</u>

<u>TAGAAGTGTGGAGCAAAGTCACTCCACTAAAATTCACCAAGATTTCAAAGGGGATTGCAGACATCATGATT</u>

<u>GCCTTTAGGACTCGAGTCCATGGTCGGTGTCCTCGCTATTTTGATGGTCCGTTGGGAGTGCTTGGCCATGC</u>

<u>CTTTCGTCCTGGTCCGGGTCTGGGTGGTGACACTCATTTTGATGAGGATGAAAACTGGACCAAGGATGGAG</u>

<u>CAGGATTCAACTTGTTTCTTGTGGCTGCTCATGAATTTGGTCATGCACTGGGGCTCTGTCACTCCAATGAT</u>

<u>CAAACAGCCTTGATGTTCCCAAATTATGTCTCCCTGGATCCCAGAAAATACCCACTTTCTCAGGATGATAT</u>

<u>CAATGGAATGGAGTCCATCTATGGAGGTCTGCCTAAGGTACCTGCTAAGCCAAAGGAACCCACTATACCCC</u>

<u>ATGCCTGTGACCCTGACTTGACTTTTGACGCTATCACAACTTTCCGCAGAGAAGTAATGTTCTTTAAAGGC</u>

<u>AGGCACCTATGGAGGATGTATTATGATATCACGGATGTTGAGTTTGAATTAATTGCTTCATTCTGGCCATC</u>

<u>TCTGCCAGCTGATCTGCAAGCTGCATACGAGAACGCCAGAGATAAGATTCTGGTTTTTAAAGATGAAAACT</u>

<u>TCTGGATGATCAGAGGATATGCTGTCTTGCCAGATTATCCCAAATCCATCCATACATTAGGTTTTCCAGGA</u>

<u>CGTGTGAAGAAAATAGATGCAGCCGTCTGTGATAAGACCACAAGAAAAACCTACTTCTTTGTGGGCATTTG</u>

<u>GTGCTGGAGGTTTGATGAAATGACCCAAACCATGGACAAAGGATTCCCGCAGAGAGTGGTAAAACACTTTC</u>

<u>CTGGAATCAGTATCCGTGTTGATGCTGCTTTCCAGTACAAAGGATTCTTCTTTTTCAGCCGTGGATCAAAG</u>

<u>CAATTTGAATAGAACATTAAGACAAAGAATATTACCCGAATCATGAGAACTAATACTTGGTTTCAATGCAA</u>

<u>AGAACCAAAGAACTCCTCATTTGGTTTTGATATCAACAAGGAAAAAGCACATTCAGGAGGCATAAAGATAT</u>

<u>TGTATCATAAGAGTTTAAGCTTGTTTATTTTTGGTATTGTTCATTTGCTGAAAAACACTTCTATTTATCAA</u>

TAAATTCATAGACCTAAAATAAACCTCAACAGGTCTTTTAATATAAATTCTGCTTCAAAATAGAATAAAAC

CATTCTTTAACAACAAGTTGCTGGTCCTAGTTCTAAATATCCAAATTCAATGGCCATTTTGAGCTGCCTGA

TTCTTTTAATAGGAAGTTATTATGTAGAAACAAAAATCTCTGACTGTACTTTAAGCCTATTTCATGCTTTG

TGGACTTGGAGAAGACATGTCTTATAACTGAATACTGAAACATTTATTAAACCAATCTTTAGCATTCTAA

The following amino acid sequence <SEQ ID NO. 4> is the predicted amino acid sequence derived from the DNA sequence of SEQ ID NO. 1:

MKRLLLLCLFFITFSSAFPLVRMTENEENMQLAQAYLNQFYSLEIEGNHLVQSKNRSLIDDKIREMQAFFG

LTVTGKLDSNTLEIMKTPRCGVPDVGQYGYTLPGWRKYNLTYRIINYTPDMARAAVDEAIQEGLEVWSKVT

PLKFTKISKGIADIMIAFRTRVHGRCPRYFDGPLGVLGHAFPPGPGLGGDTHFDEDENWTKDGAGFNLFLV

AAHEFGHALGLSHSNDQTALMFPNYVSLDPRKYPLSQDDINGIQSIYGGLPKVPAKPKEPTIPHACDPDLT

FDAITTFRREVMFFKGRHLWRIYYDITDVEFELIASFWPSLPADLQAAYENPRDKILVFKDENFWMIRGYA

VLPDYPKSIHTLGFPGRVKKIDAAVCDKTTRKTYFFVGIWCWRFDEMTQTMDKGPPQRVVKHFPGISIRVD

TABLE 5-continued

AAFQYKGFFFFSRGSKQFEYNIKTKNITRIMRTNTWFQCKEPKNSSFGFDINKEKAHSGGIKILYHKSLSL

FIFGIVHLLKNTSTYQ

The following DNA sequence MMPU9 <SEQ ID NO. 2> was identified in *H. sapiens*:

GACAAATGAGGGTTTGGCATGCAGCTCGTCATCTTAAGAGTTACTATCTTCTTGCCCTGGTGTTTCGCCGT

TCCAGTGCCCCCTGCTGCAGACCATAAAGGATGGGACTTTGTTGAGGGCTATTTCCATCAATTTTTCCTGA

CCAAGAAGGAGTCGCCACTCCTTACCCAGGAGAGACAAACACAGCTCCTGCAACAATTCCATCGGAATGGG

ACAGACCTACTTGACATGCAGATGCATGCTCTGCTACACCAGCCCCACTGTGGGGTGCCTGATGGGTCCGA

CACCTCCATCTCGCCAGGAAGATGCAAGTGGAATAAGCACACTCTAAGTTACAGGATTATCAATTACCCAC

ATGATATGAAGCCATCCGCAGTGAAAGACAGTATATATAATGCAGTTTCCATCTGGAGCAATGTGACCCCT

TTGATATTCCAGCAAGTGCAGAATGGAGATGCAGACATCAAGGTTTCTTTGTGGCAGTGGGCCCATGAAGA

TGGTTGGCCCTTTGATGGGCCAGGTGGTATCTTAGGCCATGCCTTTTTACCAAATTCTGGAAATCGTGGAG

TTGTCCATTTTGACAAGAATGAACACTGGTCAGCTTCAGACACTGGATATAATCTGTTCCTGGTTGCAACT

CATGAGATTGGGCATTCTTTGGGCCTGCAGCACTCTGGGAATCAGAGCTCCATAATGTACCCCACTTACTG

GTATCACGACCCTAGAACCTTCCAGCTCAGTGCCGATGATATCCAAAGGATCCAGCATTTGTATGGAGAAA

AATGTTCATCTGACATACCTTAATGTTAGCACAGAGGACTTATTCAACCTGTCCTTTCAGGGAGTTTATTG

GAGGATCAAAGAACTGAAAGCACTAGAGCAGCCTTGGGGACTGCTAGGATGAAGCCCTAAAGAATGCAACC

TAGTCAGGTTAGCTGAACCGACACTCAAAACGCTACTGAGTCACAATAAAGATTGTTTTAAAGAGT

The following amino acid sequence <SEQ ID NO. 5> is the predicted amino acid sequence derived from the DNA sequence of SEQ ID NO. 2:

MQLVILRVTIFLPWCFAVPVPPAADHKGWDFVEGYFHQFFLTKKESPLLTQETQTQLLQQFHRNGTDLLDM

QMHALLHQPHCGVPDGSDTSISPGRCKWNKHTLTYRIINYPHDMKPSAVKDSIYNAVSIWSNVTPLIFQQV

QNGDADIKVSFWQWAHEDGWPFDGPGGILGHAFLPNSGNPGVVHFDKNEHWSASDTGYNLFLVATHEIGHS

LGLQHSGNQSSIMYPTYWYHDPRTFQLSADDIQRIQHLYGEKCSSD

The following DNA sequence MMPU10 <SEQ ID NO. 3> was identified in *H. sapiens*:

GCTCCCCGAGCCGGGCTGCACCGGAGGCGGCGAGATGGTCGCGCGTCGGCCTCGTGCTGCGCGCGCTGC

AGCTGCTACTGTGGGGCCACCTGGACGCCCAGCCCGCGGAGCGCGGAGGCCAGGAGCTGCGCAAGGAGGCG

GAGGCATTCCTAGAGAAGTACGGATACCTCAATGAACAGGTCCCCAAAGCTCCCACCTCCACTCGATTCAG

CGATGCCATCAGAGCGTTTCAGTGGGTGTCCCAGCTACCTGTCAGCGGCGTGTTGGAGCGCGCCACCCTGC

GCCAGATGACTCGTCCCCGCTGCGGGGTTACAGATACCAAGAGTTATGCGGCCTGGGCTGAGAGGATCAGT

GACTTGTTTGCTAGACACCGGACCAAAATGAGGCGTAAGAAACGCTTTGCAAAGCAAGGTAACAAATGGTA

CAAGCAGCACCTCTCCTACCGCCTGGTGAACTGGCCTGAGCATCTCCGGAGCCGGCAGTTCGGGGCGCCGT

GCGCGCCGCCTTCGAGTTGTGGAGCAACGTCTCAGCGCTGGAGTTCTGGGAGGCCCCAGCCACAGGCCCCG

CTGACATCCGGCTCACCTTCTTCCAAGGGACCACAACGATGGGCTGGGCAATGCCTTTGATGGCCCAGGG

GGCGCCCTGGCGCACGCCTTTCCTGCCCCGCCGCGGCGAAGCGCACTTCGACCAAGATGAGCGCTGGTCCC

TGAGCCGCCGCGGCGGGCGCAACCTGTTCGTGGTGCTGGCGCACGAGATCGGTCACGCGCTTGGCCTCACC

CACTCGCCCGCGCCGCGCGCGCTCATGGCGCCCTACTACAAGAGGCTGGGCCGCGACGCGCTGCTCAGCTG

GGACGACGTGCTGGCCGTGCAGAGCCTGTATGGGAAGCCCCTAGGGGGCTCAGTGGCCGTCCAGCTCCCAG

GAAAGCTGTTCACTGACTTTGAGACCTGGGACTCCTACAGCCCCAAGGAAGGCGCCCTGAAACGCAGGGC

CCTAAATACTGCCACTCTTCCTTCGATGCCATCACTGTAGACAGGCAACAGCAACTGTACATTTTTAAAGG

GAGCCATTTCTGGGAGGTGGCAGCTGATGGCAACGTCTCAGAGCCCCGTCCACTGCAGGAAAGATGGGTCG

TABLE 5-continued

GGCTGCCCCCAACATTGAGGCTGCGGCAGTGTCATTGAATGATGGAGATTTCTACTTCTTCAAAGGGGGT

CGATGCTGGAGGTTCCGGGGCCCCAAGCCAGTGTGGGGTCTCCCACAGCTGTGCCGGGCAGGGGCCTGCC

CCGCCATCCTGACGCCGCCCTCTTCTTCCCTCCTCTGCGCCGCCTCATCCTCTTCAAGGGTGCCCGCTACT

ACGTGCTGGCCCGAGGGGGAGTGCAAGTGGAGCCCTACTACCCCCGAAGTCTGCAGGACTGGGGAGGCATC

CCTGAGGAGGTCAGCGGCGGCCTGCCGAGGCCCGATGGCTCCATCATCTTCTTCCGAGATGACCGCTACTG

GCGGCTCGACGAGGCCAAAGTGCAGGCAACCACCTCGGGCCGCTGGGCCACCGAGCTGCCCTGGATGGGCT

GCTGGCATGGCAACTCGGGGAGCGCCCTGTTCTGA

The following amino acid sequence <SEQ ID NO. 6> is the predicted amino acid sequence derived from the DNA sequence of SEQ ID NO. 3:

MVARVGLLLRALQLLLWGHLDAQPAERGGQELRKEAEAFLEKYGYLNEQVPKAPTSTRFSDAIRAFQWVSQ

LPVSGVLDRATLRQMTRPRCGVTDTNSYAAWAERISDLFARHRTKMRRKKRFAKQGNKWYKQHLSYRLVNW

PEHLRSRQFGAPCAPPSSCGATSQRWSSGRPQPQAPLTSGSPSSKGTTTMGWAMPLMAQGAPWRTPFLPRR

GEAHFDQDERWSLSRRRGRNLFVVLAHEIGHTLGLTHSPAPRALMAPYYKRLGRDALLSWDDVLAVQSLYG

KPLGGSVAVQLPGKLFTDFETWDSYSPQGRRPETQGPKYCHSSFDAITVDRQQQLYIFKGSHFWEVAADGN

VSEPRPLQERWVGLPPNIEAAAVSLNDGDFYFFKGGRCWRFRGPKPVWGLPQLCRAGGLPRHPDAALFFPP

LRRLILFKGARYYVLARGGLQVEPYYPRSLQDWGGIPEEVSGALPRPDGSIIFFRDDRYWRLDQAKLQATT

SGRWATELPWMGCWHANSGSALF

The following DNA sequence <SEQ ID NO. 7> was identified in *H. sapiens*:

ggcacgagcatgcagctcgtcatcttaagagttactatcttcttgccctggtgtttcgccgttccagtgcc ccctgctgcagaccataaaggatgggactttgttgagggctatttccatcaattttttcctgaccgagaagg agtcgccactccttacccaggagacacaaacacagctcctgcaacaattccatcggaatgggacagaccta cttgacatgcagatgcatgctctgctacaccagccccactgtggggtgcctgatgggtccgacacctccat ctcgccaggaagatgcaagtggaataagcacactctaacttacaggattatcaattacccacatgatatga agccatccgcagtgaaagacagtatatataatgcagtttccatctggagcaatgtgacccctttgatattc cagcaagtgcagaatggagatgcagacatcaaggtttctttctggcagtgggcccatgaagatggttggcc ctttgatgggccaggtggtatcttaggccatgcctttttaccaaattctggaaatcctggagttgtccatt ttgacaagaatgaacactggtcagcttcagacactggatataatctgttcctggttgcaactcatgagatt gggcattctttgggcctgcagcactctgggaatcagagctccataatgtacccacttactggtatcacga ccctagaaccttccagctcagtgccgatgatatccaaaggatccagcatttgtatggagaaaatgttcat ctgacatacctttaatgttagcacagaggacttattcaacctgtctttcagggagtttattggaggatcaaa gaactgaaagcactagagcagccttggggactgctaggatgaagccctaaagaatgcaacctagtcaggtt agctgaaccgacactcaaaacgctactgagtcacaataaagattgttttaaagagtaaaaaaaaaaaaaa aaaaa The following amino acid sequence <SEQ ID NO. 8> is the amino acid sequence derived from the DNA sequence of SEQ ID NO. 7:

MVRVTWCAVVAADHKGWDVGYHTKSTTTHRNGTDDMMHAHHCGVDGSDTSSGRCKWNKHTTYRNYHDMKSA

VKDSYNAVSWSNVTVNGDADKVSWWAHDGWDGGGGHANSGNGVVHDKNHWSASDTGYNVATHGHSGHSGNS

SMYTYWYHDRTSADDRHYGKCSSD

EXAMPLE 2

Cloning of MMP cDNA cDNAs may be sequenced directly using an AB1377 or ABI373A fluorescence-based sequencer (Perkin Elmer/Applied Biosystems Division, PE/ABD, Foster City, Calif.) and the ABI PRISM Ready Dye-Deoxy Terminator kit with Taq FS polymerase. Each ABI cycle sequencing reaction contains about 0.5 µg of plasmid DNA. Cycle-sequencing is performed using an initial denaturation at 98° C. for 1 min, followed by 50 cycles: 98° C. for 30 sec, annealing at 50° C. for 30 sec, and extension at 60° C. for 4 min. Temperature cycles and times are controlled by a Perkin-Elmer 9600 thermocycler. Extension products are purified using Centri-flex gel filtration (Advanced Genetic Technologies Corp., Gaithersburg, Md.). Each reaction product is loaded by pipette onto the column, which is then centrifuged in a swinging bucket centrifuge (Sorvall model RT6000B tabletop centrifuge) at 1500×g for 4 min at room temperature. Column-purified samples are dried under vacuum for about 40 min and then dissolved in 5 µl of a DNA loading solution (83% deionized formamide, 8.3 mM EDTA, and 1.6 mg/ml Blue Dextran). The samples are then heated to 90° C. for three minutes and loaded into the gel sample wells for sequence analysis by the ABI377 sequencer. Sequence analysis is performed by importing ABI373A files into the Sequencher program (Gene Codes, Ann Arbor, Mich.). Generally, sequence reads of 700 bp are obtained. Potential sequencing errors are minimized by obtaining sequence information from both DNA strands and by re-sequencing difficult areas using primers at different locations until all sequencing ambiguities are removed.

To isolate a cDNA clone encoding full length MMP, a DNA fragment corresponding to a nucleotide sequence of SEQ ID NOS:1–3, or a portion thereof, can be used as a probe for hybridization screening of a phage cDNA library. The DNA fragment is amplified by the polymerase chain reaction (PCR) method. The PCR reaction mixture of 50 ml contains polymerase mixture (0.2 mM dNTPs, 1×PCR Buffer and 0.75 ml Expand High Fidelity Polymerase (Roche Biochemicals)), 1 µg of 3206491 plasmid, 50 pmoles of forward primer and 50 pmoles of reverse primer. The primers are preferably 10 to 25 nucleotides in length and are determined by procedures well known to those skilled in the art. Amplification is performed in an Applied Biosystems PE2400 thermocycler, using the following program: 95° C. for 15 seconds, 52° C. for 30 seconds and 72° C. for 90 seconds; repeated for 25 cycles. The amplified product is separated from the plasmid by agarose gel electrophoresis, and purified by Qiaquick™ gel extraction kit (Qiagen).

A lambda phage library containing cDNAs cloned into lambda ZAPII phage-vector is plated with *E. coli* XL-1 blue host, on 15 cm LB-agar plates at a density of 50,000 pfu per plate, and grown overnight at 37° C.; (plated as described by Sambrook et al., supra). Phage plaques are transferred to nylon membranes (Amersham Hybond N.J.), denatured for 2 minutes in denaturation solution (0.5 M NaOH, 1.5 M NaCl), renatured for 5 minutes in renaturation solution (1 M Tris pH 7.5, 1.5 M NaCl), and washed briefly in 2'SSC (20×SSC: 3 M NaCl, 0.3 M Na-citrate). Filter membranes are dried and incubated at 80° C. for 120 minutes to cross-link the phage DNA to the membranes.

The membranes are hybridized with a DNA probe prepared as described above. A DNA fragment (25 ng) is labeled with $\alpha$-$^{32}$P-dCTP (NEN) using Rediprime™ random priming (Amersham Pharmacia Biotech), according to the manufacturer's instructions. Labeled DNA is separated from unincorporated nucleotides by S200 spin columns (Amersham Pharmacia Biotech), denatured at 95° C. for 5 minutes and kept on ice. The DNA-containing membranes (above) are pre-hybridized in 50 ml ExpressHyb™ (Clontech) solution at 68° C. for 90 minutes. Subsequently, the labeled DNA probe is added to the hybridization solution, and the probe is left to hybridize to the membranes at 68° C. for 70 minutes. The membranes are washed five times in 2×SSC, 0.1% SDS at 42° C. for 5 minutes each, and finally washed for 30 minutes in 0.1×SSC, 0.2% SDS. Filters are exposed to Kodak XAR film (Eastman Kodak Company, Rochester, N.Y., USA) with an intensifying screen at −80° C. for 16 hours. One positive colony is isolated from the plates, and replated with about 1000 pfu on a 15 cm LB plate. Plating, plaque lift to filters and hybridization are performed as described above. About four positive phage plaques are isolated from this secondary screening.

cDNA containing plasmids (pBluescript SK-) are rescued from the isolated phages by in vivo excision by culturing XL-1 blue cells co-infected with the isolated phages and with the Excision helper phage, as described by manufacturer (Stratagene). XL-blue cells containing the plasmids are plated on LB plates and grown at 37° C. for 16 hours. Colonies (18) from each plate are replated on LB plates and grown. One colony from each plate is stricken onto a nylon filter in an ordered array, and the filter is placed on a LB plate to raise the colonies. The filter is then hybridized with a labeled probe as described above. About three positive colonies are selected and grown up in LB medium. Plasmid DNA is isolated from the three clones by Qiagen Midi Kit™ (Qiagen) according to the manufacturer's instructions. The size of the insert is determined by digesting the plasmid with the restriction enzymes NotI and SalI, which establishes an insert size. The sequence of the entire insert is determined by automated sequencing on both strands of the plasmids.

EXAMPLE 3

Subcloning of the Coding Region of MMP Via PCR

Additional experiments may be conducted to subclone the coding region of MMP and place the isolated coding region into a useful vector. Two additional PCR primers are designed based on the coding region of MMP, corresponding to either end. To protect against exonucleolytic attack during subsequent exposure to enzymes, e.g., Taq polymerase, primers are routinely synthesized with a protective run of nucleotides at the 5' end that are not necessarily complementary to the desired target.

PCR is performed in a 50 µl reaction containing 34 µl H$_2$O, 5 µl 10×TT buffer (140 mM ammonium sulfate, 0.1% gelatin, 0.6 M Tris-tricine, pH 8.4), 5 µl 15 mM MgSO$_4$, 2 µl dNTP mixture (dGTP, dATP, dTTP, and dCTP, each at 10 mM), 3 µl genomic phage DNA (0.25 µg/µl), 0.3 µl Primer 1 (1 µg/µl), 0.3 µl Primer 2 (1 µg/µl), 0.4 µl High Fidelity Taq polymerase (Boehringer Mannheim). The PCR reaction is started with 1 cycle of 94° C. for 2 minutes; followed by 25 cycles at 94° C. for 30 seconds, 55° C. for 30 seconds, and 72° C. for 1.3 minutes.

The contents from the PCR reaction are loaded onto a 2% agarose gel and fractionated. The DNA band of expected size is excised from the gel, placed in a GenElute Agarose spin column (Supelco), and spun for 10 minutes at maximum speed in a microfuge tube placed in a microcentrifuge.

The eluted DNA is precipitated with ethanol and resuspended in 6 µl H₂O for ligation.

The PCR-amplified DNA fragment containing the coding region is cloned into pCR2.1 using a protocol standard in the art. In particular, the ligation reaction consists of 6 µl of MMP DNA, 1 µl 10× ligation buffer, 2 µl pCR2.1 (25 ng/µl, Invitrogen), and 1 µl T4 DNA ligase (Invitrogen). The reaction mixture is incubated overnight at 14° C., and the reaction is then terminated by heating at 65° C. for 10 minutes. Two microliters of the ligation reaction are transformed into One Shot cells (Invitrogen) and plated onto ampicillin plates. A single colony containing a recombinant pCR2.1 bearing an insert is used to inoculate a 5 ml culture of LB medium. Plasmid DNA is purified using the Concert Rapid Plasmid Miniprep System (GibcoBRL) and sequenced. Following confirmation of the sequence, a 50 ml culture of LB medium is inoculated with the transformed One Shot cells, cultured, and processed using a Qiagen Plasmid Midi Kit to yield purified pCR-MMP.

EXAMPLE 4

Hybridization Analysis to Demonstrate MMP Expression in Various Tissues

The expression of MMP in mammals, such as the rat or mouse, is investigated by in situ hybridization histochemistry as described in Bertilsson et al. (supra). Tissue sections are thaw-mounted onto silanized, nuclease-free slides (CEL Associates, Inc., Houston, Tex.), and stored at −80° C. Sections are processed starting with post-fixation in cold 4% paraformaldehyde, rinsed in cold phosphate-buffered saline (PBS), acetylated using acetic anhydride in triethanolamine buffer, and dehydrated through a series of alcohol washes in 70%, 95%, and 100% alcohol at room temperature. Subsequently, sections are delipidated in chloroform, followed by rehydration through successive exposure to 100% and 95% alcohol at room temperature. Microscope slides containing processed cryosections are allowed to air dry prior to hybridization.

An MMP-specific probe is generated using PCR. Following PCR amplification, the fragment is digested with restriction enzymes and cloned into pBluescript II cleaved with the same enzymes. For production of a probe specific for the sense strand of MMP, the MMP clone in pBluescript II is linearized with a suitable restriction enzyme, which provides a substrate for labeled run-off transcripts (i.e., cRNA riboprobes) using the vector-borne T7 promoter and commercially available T7 RNA polymerase. A probe specific for the antisense strand of MMP is also readily prepared using the MMP clone in pBluescript II by cleaving the recombinant plasmid with a suitable restriction enzyme to generate a linearized substrate for the production of labeled run-off cRNA transcripts using the T3 promoter and cognate polymerase. The riboprobes are labeled with [$^{35}$S]-UTP to yield a specific activity of about $0.40 \times 10^6$ cpm/pmol for antisense riboprobes and about $0.65 \times 10^6$ cpm/pmol for sense-strand riboprobes Each riboprobe is subsequently denatured and added (2 pmol/ml) to hybridization buffer which contained 50% formamide, 10% dextran, 0.3 M NaCl, 10 mM Tris (pH 8.0), 1 mM EDTA, 1× Denhardt's Solution, and 10 mM dithiothreitol. Microscope slides containing sequential brain cryosections are independently exposed to 45 µl of hybridization solution per slide and silanized cover slips are placed over the sections being exposed to hybridization solution. Sections are incubated overnight (15–18 hours) at 52° C. to allow hybridization to occur. Equivalent series of cryosections are exposed to sense or antisense MMP-specific cRNA riboprobes.

Following the hybridization period, coverslips are washed off the slides in 1×SSC, followed by RNase A treatment involving the exposure of slides to 20 µg/ml RNase A in a buffer containing 10 mM Tris-HCl (pH 7.4), 0.5 M EDTA, and 0.5 M NaCl for 45 minutes at 37° C. The cryosections are then subjected to three high-stringency washes in 0.1× SSC at 52° C. for 20 minutes each. Following the series of washes, cryosections are dehydrated by consecutive exposure to 70%, 95%, and 100% ammonium acetate in alcohol, followed by air drying and exposure to Kodak BioMax MR-1 film. After 13 days of exposure, the film is developed. Based on these results, slides containing tissue that hybridized, as shown by film autoradiograms, are coated with Kodak NTB-2 nuclear track emulsion and the slides are stored in the dark for 32 days. The slides are then developed and counterstained with hematoxylin. Emulsion-coated sections are analyzed microscopically to determine the specificity of labeling. The signal is determined to be specific if autoradiographic grains (generated by antisense probe hybridization) are clearly associated with cresyl violate-stained cell bodies. Autoradiographic grains found between cell bodies indicates non-specific binding of the probe.

A PCR-based system (RapidScan™ Gene Expression Panel, OriGene Technologies, Rockville, Md.) may be used to generate a comprehensive expression profile of the putative MMP in human tissue, and in human brain regions. The RapidScan Expression Panel is comprised of first-strand cDNAs from various human tissues and brain regions that were serially diluted over a 4-log range and arrayed into a multi-well PCR plate. Human tissues arrayed may include: brain, heart, kidney, spleen, liver, colon, lung, small intestine, muscle, stomach, testis, placenta, salivary gland, thyroid, adrenal gland, pancreas, ovary, uterus, prostate, skin, PBL, bone marrow, fetal brain, fetal liver. Human brain regions arrayed may include: frontal lobe, temporal lobe, cerebellum, hippocampus, substantia nigra, caudate nucleus, amygdala, thalamus, hypothalamus, pons, medulla and spinal cord.

Expression of the MMP in the various tissues is detected by using PCR primers designed based on the available sequence of the protein that will prime the synthesis of a fragment of pre-determined size in the presence of the appropriate cDNA. The dilution range of cDNA deposited on the plate (e.g., 4-log) is chosen to ensure that the amplification reaction is within the linear range and, hence, will facilitate semi-quantitative determination of relative mRNA accumulation in the various tissues or brain regions examined.

Expression of MMP in different tissues provides an indication that modulators of MMP activity have utility for treating various disorders, including but not limited to metabolic diseases and disorders (e.g., type 2 diabetes, obesity, cardiovascular, dyslipidemias, adipogenesis, retinopathies, neuropathies, nephropathies etc.), proliferative diseases and cancers (e.g., different cancers such as breast, colon, lung, etc., tumor growth, tumor invasion, and hyperproliferative disorders such as psoriasis, prostate hyperplasia, etc.), hormonal disorders (e.g., male/female hormonal replacement, polycystic ovarian syndrome, alopecia, etc.), CNS disorders (e.g., degenerative disorders such as Parkinson's, Alzheimer's, etc.), inflammatory conditions (e.g., Chron's disease, arthritis), diseases related to cell differentiation and homeostasis, cardiomyopathy, atherosclerosis, thromboembolic diseases, Sjögren's syndrome, renal failure, periodontal diseases, retinal neovascularization, wound healing, and neurodegenerative diseases including, for example, Alzheimer's disease, multiple sclerosis, Parkinson's disease, and motoneuron disease, among others. Use of MMP modulators, including MMP ligands (activators and repressors) and anti-MMP antibodies, to treat individuals having such disease states is intended as an aspect of the invention.

EXAMPLE 5

Northern Blot Analysis

Northern blots are performed to examine the expression of mRNA. The sense orientation oligonucleotide and the antisense-orientation oligonucleotide, described above, are used as primers to amplify a portion of the MMP cDNA sequence of a nucleotide sequence of SEQ ID NOS: 1–3.

Multiple human tissue northern blot from Clontech are hybridized with the probe according to the recommendations of the manufacturer, and as described by Bertilsson (supra). The probe is labeled with α-$^{32}$P-dCTP by Rediprime™ DNA labeling system (Amersham Pharmacia), purified on Nick Column™ (Amersham Pharmacia) and added to the hybridization solution. The filters are washed several times at 42° C. in 0.2×SSC, 0.1% SDS. Filters are exposed to Kodak XAR film (Eastman Kodak Company, Rochester, N.Y., USA) with intensifying screen at –80° C.

EXAMPLE 6

Recombinant Expression of MMP in Eukaryotic Host Cells

A. Expression of MMP in Mammalian Cells

To produce MMP protein, a MMP-encoding polynucleotide is expressed in a suitable host cell using a suitable expression vector and standard genetic engineering techniques. For example, the MMP-encoding sequence described in Example 1 is subcloned into the commercial expression vector pzeoSV2 (Invitrogen, San Diego, Calif.) and transfected into Chinese Hamster Ovary (CHO) cells using the transfection reagent FuGENE 6 or Dosper (Boehringer-Mannheim) and the transfection protocol provided in the product insert. Other eukaryotic cell lines, including human embryonic kidney (HEK 293), human colon cancer cells (CaCo-2), and COS cells, are suitable as well. Cells stably expressing MMP are selected by growth in the presence of 100 μg/ml zeocin (Stratagene, LaJolla, Calif.). Optionally, MMP may be purified from the cells using standard chromatographic techniques. To facilitate purification, antisera is raised against one or more synthetic peptide sequences that correspond to portions of the MMP amino acid sequence, and the antisera is used to affinity purify MMP. The MMP also may be expressed in-frame with a tag sequence (e.g., polyhistidine, hemagluttinin, FLAG) to facilitate purification. Moreover, it will be appreciated that many of the uses for MMP polypeptides, such as assays described below, do not require purification of MMP from the host cell.

B. Expression of MMP in HEK-293 Cells

For expression of MMP in mammalian cells 293 (transformed human, primary embryonic kidney cells), a plasmid bearing the relevant MMP coding sequence is prepared, using vector pSecTag2A (Invitrogen). Vector pSecTag2A contains the murine IgK chain leader sequence for secretion, the c-myc epitope for detection of the recombinant protein with the anti-myc antibody, a C-terminal polyhistidine for purification with nickel chelate chromatography, and a Zeocin resistant gene for selection of stable transfectants. The forward primer for amplification of this MMP cDNA is determined by routine procedures and preferably contains a 5' extension of nucleotides to introduce the HindIII cloning site and nucleotides matching the MMP sequence. The reverse primer is also determined by routine procedures and preferably contains a 5' extension of nucleotides to introduce a XhoI restriction site for cloning and nucleotides corresponding to the reverse complement of the MMP sequence. The PCR conditions use 55° C. as the annealing temperature. The PCR product is gel purified and cloned into the HindIII-XhoI sites of the vector.

The DNA is purified using Qiagen chromatography columns and transfected into 293 cells using DOTAP transfection media (Boehringer Mannheim, Indianapolis, Ind.). Transiently transfected cells are tested for expression after 24 hours of transfection, using western blots probed with anti-His and anti-MMP peptide antibodies. Permanently transfected cells are selected with Zeocin and propagated. Production of the recombinant protein is detected from both cells and media by western blots probed with anti-His, anti-Myc or anti-MMP peptide antibodies.

C. Expression of MMP in COS Cells

For expression of the MMP in COS7 cells, a polynucleotide molecule having a nucleotide sequence of SEQ ID NOS: 1–3 can be cloned into vector p3-CI. This vector is a pUC18-derived plasmid that contains the HCMV (human cytomegalovirus) promoter-intron located upstream from the bGH (bovine growth hormone) polyadenylation sequence and a multiple cloning site. In addition, the plasmid contains the dhrf (dihydrofolate reductase) gene which provides selection in the presence of the drug methotrexane (MTX) for selection of stable transformants.

The forward primer is determined by routine procedures and preferably contains a 5' extension which introduces an XbaI restriction site for cloning, followed by nucleotides which correspond to a nucleotide sequence of SEQ ID NOS: 1–3. The reverse primer is also determined by routine procedures and preferably contains 5'-extension of nucleotides which introduces a SalI cloning site followed by nucleotides which correspond to the reverse complement of a nucleotide sequence of SEQ ID NOS: 1–3.

The PCR consists of an initial denaturation step of 5 min at 95° C., 30 cycles of 30 sec denaturation at 95° C., 30 sec annealing at 58° C. and 30 sec extension at 72° C., followed by 5 min extension at 72° C. The PCR product is gel purified and ligated into the XbaI and SalI sites of vector p3-CI. This construct is transformed into E. coli cells for amplification and DNA purification. The DNA is purified with Qiagen chromatography columns and transfected into COS 7 cells using Lipofectamine reagent from BRL, following the manufacturer's protocols. Forty-eight and 72 hours after transfection, the media and the cells are tested for recombinant protein expression.

MMP expressed from a COS cell culture can be purified by concentrating the cell-growth media to about 10 mg of protein/ml, and purifying the protein by, for example, chromatography. Purified MMP is concentrated to 0.5 mg/ml in an Amicon concentrator fitted with a YM-10 membrane and stored at –80° C.

D. Expression of MMP in Insect Cells

For expression of MMP in a baculovirus system, a polynucleotide molecule having a nucleotide sequence of SEQ ID NOS: 1–3 can be amplified by PCR. The forward primer is determined by routine procedures and preferably contains a 5' extension which adds the NdeI cloning site, followed by followed by nucleotides which correspond to a nucleotide sequence of SEQ ID NOS: 1–3. The reverse primer is also determined by routine procedures and preferably contains a 5' extension which introduces the KpnI cloning site, followed by followed by nucleotides which correspond to the reverse complement of a nucleotide sequence of SEQ ID NOS: 1–3.

The PCR product is gel purified, digested with NdeI and KpnI, and cloned into the corresponding sites of vector pACHTL-A (Pharmingen, San Diego, Calif.). The pAcHTL expression vector contains the strong polyhedrin promoter of the Autographa californica nuclear polyhedrosis virus (AcMNPV), and a 6×His tag upstream from the multiple cloning site. A protein kinase site for phosphorylation and a thrombin site for excision of the recombinant protein precede the multiple cloning site is also present. Of course, many other baculovirus vectors could be used in place of pAcHTL-A, such as pAc373, pVL941 and pAcIM1. Other suitable vectors for the expression of MMP polypeptides can be used, provided that the vector construct includes appropriately located signals for transcription, translation, and trafficking, such as an in-frame AUG and a signal peptide, as required. Such vectors are described in Luckow et al., Virology 170:31–39, among others.

The virus is grown and isolated using standard baculovirus expression methods, such as those described in Summers et al. (A Manual of Methods for Baculovirus Vectors and Insect Cell Culture Procedures, Texas Agricultural Experimental Station Bulletin No. 1555 (1987)).

In a preferred embodiment, pAcHLT-A containing MMP gene is introduced into baculovirus using the "BaculoGold" transfection kit (Pharmingen, San Diego, Calif.) using methods established by the manufacturer. Individual virus isolates are analyzed for protein production by radiolabeling infected cells with $^{35}$S-methionine at 24 hours post infection. Infected cells are harvested at 48 hours post infection, and the labeled proteins are visualized by SDS-PAGE. Viruses exhibiting high expression levels can be isolated and used for scaled up expression.

For expression of a MMP polypeptide in Sf9 cells, a polynucleotide molecule having a nucleotide sequence of SEQ ID NOS: 1–3, can be amplified by PCR using the primers and methods described above for baculovirus expression. The MMP cDNA is cloned into vector pAcHLT-A (Pharmingen) for expression in Sf9 insect. The insert is cloned into the NdeI and KpnI sites, after elimination of an internal NdeI site (using the same primers described above for expression in baculovirus). DNA is purified with Qiagen chromatography columns and expressed in Sf9 cells. Preliminary Western blot experiments from non purified plaques are tested for the presence of the recombinant protein of the expected size which reacted with the MMP-specific antibody. These results are confirmed after further purification and expression optimization in HiG5 cells.

EXAMPLE 7

Zymography

MMP protease activity is analyzed by substrate gel electrophoresis (zymography) in polyacrylamide gels containing 2 mg/ml gelatin or 1.5 mg/ml casein. Samples are dissolved in modified Laemmli sample buffer [containing 2.5% (v/v) SDS without 2-mercaptoethanol] and electrophoresed, without prior boiling, at 4° C. After removal of the SDS by washing in 2.5% (v/v) Triton X-100 in 50 mM Tris/HCl, pH 7.5, for 1 h, the gels are incubated overnight at 37° C. in a buffer containing 40 mM Tris/HCl, pH 7.5, and 10 mM $CaCl_2$. Staining with 0.5% (w/v) Coomassie Brilliant Blue (Bio-Rad, Richmond, Calif., U.S.A.) in 30% (v/v) isopropanol/10% (v/v) acetic acid followed by destaining with 30% isopropanol/10% acetic acid allows identification of gelatinolytic or caseinolytic activity as clear zones in a blue background.

EXAMPLE 8

Antibodies to MMP

Standard techniques are employed to generate polyclonal or monoclonal antibodies to the MMP, and to generate useful antigen-binding fragments thereof or variants thereof, including "humanized" variants. Such protocols can be found, for example, in Sambrook et al. (1989) and Harlow et al. (Eds.), *Antibodies A Laboratory Manual*; Cold Spring Harbor Laboratory; Cold Spring Harbor, N.Y. (1988). In one embodiment, recombinant MMP polypeptides (or cells or cell membranes containing such polypeptides) are used as antigen to generate the antibodies. In another embodiment, one or more peptides having amino acid sequences corresponding to an immunogenic portion of MMP (e.g., 6, 7, 8, 9, 10, 11, 12, 13, 14, 15, 16, 17, 18, 19, 20, or more amino acids) are used as antigen. The antigen may be mixed with an adjuvant or linked to a hapten to increase antibody production.

A. Polyclonal or Monoclonal Antibodies

As one exemplary protocol, recombinant MMP or a synthetic fragment thereof is used to immunize a mouse for generation of monoclonal antibodies (or larger mammal, such as a rabbit, for polyclonal antibodies). To increase antigenicity, peptides are conjugated to Keyhole Lympet Hemocyanin (Pierce), according to the manufacturer's recommendations. For an initial injection, the antigen is emulsified with Freund's Complete Adjuvant and injected subcutaneously. At intervals of two to three weeks, additional aliquots of MMP antigen are emulsified with Freund's Incomplete Adjuvant and injected subcutaneously. Prior to the final booster injection, a serum sample is taken from the immunized mice and assayed by western blot to confirm the presence of antibodies that immunoreact with MMP. Serum from the immunized animals may be used as a polyclonal antisera or used to isolate polyclonal antibodies that recognize MMP. Alternatively, the mice are sacrificed and their spleen removed for generation of monoclonal antibodies.

To generate monoclonal antibodies, the spleens are placed in 10 ml serum-free RPMI 1640, and single cell suspensions are formed by grinding the spleens in serum-free RPMI 1640, supplemented with 2 mM L-glutamine, 1 mM sodium pyruvate, 100 units/ml penicillin, and 100 µg/ml streptomycin (RPMI) (Gibco, Canada). The cell suspensions are filtered and washed by centrifugation and resuspended in serum-free RPMI. Thymocytes taken from three naive Balb/c mice are prepared in a similar manner and used as a Feeder Layer. NS-1 myeloma cells, kept in log phase in RPMI with 10% fetal bovine serum (FBS) (Hyclone Laboratories, Inc., Logan, Utah) for three days prior to fusion, are centrifuged and washed as well.

To produce hybridoma fusions, spleen cells from the immunized mice are combined with NS-1 cells and centrifuged, and the supernatant is aspirated. The cell pellet is dislodged by tapping the tube, and 2 ml of 37° C. PEG 1500 (50% in 75 mM HEPES, pH 8.0) (Boehringer-Mannheim) is stirred into the pellet, followed by the addition of serum-free RPMI. Thereafter, the cells are centrifuged, resuspended in RPMI containing 15% FBS, 100 µM sodium hypoxanthine, 0.4 µM aminopterin, 16 µM thymidine (HAT) (Gibco), 25 units/ml IL-6 (Boehringer-Mannheim) and $1.5 \times 10^6$ thymocytes/ml, and plated into 10 Corning flat-bottom 96-well tissue culture plates (Corning, Corning N.Y.).

On days 2, 4, and 6 after the fusion, 100 µl of medium is removed from the wells of the fusion plates and replaced with fresh medium. On day 8, the fusions are screened by ELISA, testing for the presence of mouse IgG that binds to MMP. Selected fusion wells are further cloned by dilution until monoclonal cultures producing anti-MMP antibodies are obtained.

B. Humanization of Anti-MMP Monoclonal Antibodies

The expression pattern of MMP as reported herein suggests therapeutic indications for MMP inhibitors (repressors). MMP-neutralizing antibodies comprise one class of therapeutics useful as MMP repressors. Following are protocols to improve the utility of anti-MMP monoclonal antibodies as therapeutics in humans by "humanizing" the monoclonal antibodies to improve their serum half-life and render them less immunogenic in human hosts (i.e., to prevent human antibody response to non-human anti-MMP antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest with the constant domains of human antibody molecules. (See, e.g., Morrison et al., Adv. Immunol., 44:65–92 (1989)). The variable domains of MMP-neutralizing anti-MMP antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions (CDR) of the non-human monoclonal antibody genes are cloned into human antibody sequences. (See, e.g., Jones et al., Nature 321:522–525 (1986); Riechmann et al., Nature 332:323–327 (1988); Verhoeyen et al., Science 239: 1534–36 (1988); and Tempest et al., Bio/Technology 9:266–71 (1991)). If necessary, the β-sheet framework of the human antibody surrounding the CDR3 regions also is modified to more closely mirror the three dimensional structure of the antigen-binding domain of the original monoclonal antibody. (See Kettleborough et al., Protein Engin., 4:773–783 (1991); and Foote et al., J. Mol. Biol., 224:487–499 (1992)).

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan, Molecular Immunol., 28(4/5):489–98 (1991).

The foregoing approaches are employed using MMP-neutralizing anti-MMP monoclonal antibodies and the hybridomas that produce them to generate humanized MMP-neutralizing antibodies that are useful as therapeutics to treat or palliate conditions wherein MMP expression or ligand-mediated MMP activity is detrimental.

C. Human MMP-Neutralizing Antibodies from Phage Display

Human MMP-neutralizing antibodies are generated by phage display techniques such as those described in Aujame et al., Human Antibodies 8(4): 155–168 (1997); Hoogenboom, TIBTECH 15:62–70 (1997); and Rader et al., Curr. Opin. Biotechnol. 8:503–508 (1997), all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is screened for MMP-specific phage-antibodies using labeled or immobilized MMP as antigen-probe.

D. Human MMP-neutralizing Antibodies from Transgenic Mice

Human MMP-neutralizing antibodies are generated in transgenic mice essentially as described in Bruggemann et al., Immunol. Today 17(8):391–97 (1996) and Bruggemann et al., Curr. Opin. Biotechnol. 8:455–58 (1997). Transgenic mice carrying human V-gene segments in germline configuration and that express these transgenes in their lymphoid tissue are immunized with a MMP composition using conventional immunization protocols. Hybridomas are generated using B cells from the immunized mice using conventional protocols and screened to identify hybridomas secreting anti-MMP human antibodies (e.g., as described above).

EXAMPLE 9

Assays to Assess MMP Activity and to Identify Modulators of MMP Activity

A. Synthetic Fluorogenic Peptide Substrate Cleavage Assays

Fluorogenic peptide substrates may be used to test proteinase activity as well as inhibitors of proteinase activity. Such peptide substrates may be purchased, for example, from BACHEM Bioscience Inc, who offer several MMP substrates and various enzyme substrates, for example a substrate of tumor necrosis factor-α (TNF-α) converting enzyme (TACE). Substrates are prepared as 50–500 µM stock solutions in 1:1 dimethyl sulfoxide (DMSO) and water. Fluorescent assays are performed at $\lambda_{excitation}$=328 nm and $\lambda_{emmission}$=393 nm using a luminescence spectrometer equipped with a constant-temperature water bath. The relationship between fluorescence units and nanomoles of product produced is determined from the fluorescence value obtained when all the substrate is hydrolyzed.

B. Kinetic Parameters

Assays for obtaining kinetic parameters are performed at 25° C. in 10 mM $CaCl_2$ 0.2 M NaCl and 0.05% Brij-35 in 50 mM HEPES, pH 7.5 over the substrate concentration range 1–4 µM range and enzyme concentration range 0.06–50 nM under steady-state conditions. Stock solutions of MMPs are diluted to 1–500 nM by adding 50 mM HEPES buffer containing 10 mM $CaCl_2$ 0.2 M NaCl, and 0.05% Brij-35 or 50 mM Tricine buffer with the same constituents. A typical assay is carried out by incubating 186 µL of buffer solution and 4 µL of substrate solution in an assay cuvette for at least for 15 min. at 25° C., and then adding 10 µL of enzyme solution into the assay cuvette. Initial hydrolysis rates are monitored for 10–30 min.

C. Inhibition Studies

Modulators of MMP activity may be studied using the above assay. The activity of MMPs in the absence of potential modulating compounds is compared to the activity of MMPs in the presence of varying concentrations of potential modulating compounds.

Among the modulators that can be identified by these assays are natural ligand compounds of the MMP; synthetic analogs and derivatives of natural ligands; antibodies, antibody fragments, and/or antibody-like compounds derived from natural antibodies or from antibody-like combinatorial libraries; and/or synthetic compounds identified by high-throughput screening of libraries; and the like. All modulators that bind MMP are useful for identifying MMPs in tissue samples (e.g., for diagnostic purposes, pathological purposes, and the like). Activator and repressor modulators are useful for up-regulating and down-regulating MMP activity, respectively, to treat disease states characterized by abnormal levels of MMP activity. The assays may be performed using single putative modulators, and/or may be performed using a known activator in combination with candidate repressors (or visa versa).

Some of the preferred embodiments of the invention described above are outlined below and include, but are not limited to, the following embodiments. As those skilled in the art will appreciate, numerous changes and modifications may be made to the preferred embodiments of the invention without departing from the spirit of the invention. It is intended that all such variations fall within the scope of the invention.

The entire disclosure of each publication cited herein is hereby incorporated by reference.

What is claimed is:

1. An isolated polypeptide comprising a sequence with at least 99% sequence homology to SEQ ID NO: 6, said polypeptide having matrix metalloproteinase (MMP) activity, wherein sequence homology is determined using the Gap program with default settings.

2. A composition comprising the polypeptide of claim 1 and an acceptable carrier or diluent.

* * * * *